(12) United States Patent
Shenk et al.

(10) Patent No.: US 10,813,934 B2
(45) Date of Patent: Oct. 27, 2020

(54) SIRTUIN MODULATORS AS INHIBITORS OF CYTOMEGALOVIRUS

(71) Applicant: The Trustees of Princeton University, Princeton, NJ (US)

(72) Inventors: Thomas Shenk, Princeton, NJ (US); Emre Koyuncu, Princeton, NJ (US); Ileana M. Cristea, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 15/187,269

(22) Filed: Jun. 20, 2016

(65) Prior Publication Data

US 2016/0296523 A1   Oct. 13, 2016

Related U.S. Application Data

(63) Continuation of application No. 13/982,779, filed as application No. PCT/US2012/023621 on Feb. 2, 2012, now abandoned.

(60) Provisional application No. 61/438,846, filed on Feb. 2, 2011, provisional application No. 61/527,102, filed on Aug. 24, 2011.

(51) Int. Cl.
| | |
|---|---|
| *A61K 31/40* | (2006.01) |
| *A61K 31/35* | (2006.01) |
| *A61K 31/12* | (2006.01) |
| *A61K 31/497* | (2006.01) |
| *A61K 31/47* | (2006.01) |
| *A61K 31/513* | (2006.01) |
| *A61K 31/167* | (2006.01) |
| *A61K 31/17* | (2006.01) |
| *A61K 31/404* | (2006.01) |
| *A61K 45/06* | (2006.01) |
| *A61K 31/366* | (2006.01) |
| *A61K 31/496* | (2006.01) |
| *A61K 31/498* | (2006.01) |

(52) U.S. Cl.
CPC ......... *A61K 31/513* (2013.01); *A61K 31/167* (2013.01); *A61K 31/17* (2013.01); *A61K 31/366* (2013.01); *A61K 31/404* (2013.01); *A61K 31/496* (2013.01); *A61K 31/498* (2013.01); *A61K 45/06* (2013.01)

(58) Field of Classification Search
CPC .................................................... A61K 31/166
USPC ....................................................... 514/619
See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts'o et al. |
| 4,476,301 | A | 10/1984 | Imbach et al. |
| 4,845,205 | A | 7/1989 | Huynh Dinh et al. |
| 4,981,957 | A | 1/1991 | Lebleu et al. |

(Continued)

FOREIGN PATENT DOCUMENTS

| | | |
|---|---|---|
| EP | 1072679 A2 | 1/2001 |
| WO | WO-86/02266 A1 | 4/1986 |

(Continued)

OTHER PUBLICATIONS

Pasco et al. "Characterization of sirtuin inhibitors in nematodes expressing a muscular dystrphy protein reveals muscle cell and behavioral protection by specific sirtinol analogues," J. Medicinal Chemistry, 2010, vol. 53, pp. 1407-1411.*

(Continued)

*Primary Examiner* — Shengjun Wang
(74) *Attorney, Agent, or Firm* — Marshall, Gerstein & Borun LLP

(57) ABSTRACT

Agents and methods of inhibiting or improving the growth of viruses are provided.

8 Claims, 6 Drawing Sheets

Specification includes a Sequence Listing.

Tenovin-6

Salermide

(56) References Cited

U.S. PATENT DOCUMENTS

| | | |
|---|---|---|
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 5,898,031 A | 4/1999 | Crooke |
| 5,985,848 A | 11/1999 | Furneaux et al. |
| 6,005,096 A | 12/1999 | Matteucci et al. |
| 6,066,722 A | 5/2000 | Furneaux et al. |
| 6,107,094 A | 8/2000 | Crooke |
| 6,228,847 B1 | 5/2001 | Furneaux et al. |
| 6,492,347 B2 | 12/2002 | Furneaux et al. |
| 6,803,455 B2 | 10/2004 | Furneaux et al. |
| 7,223,833 B1 | 5/2007 | Nielsen et al. |
| 7,345,178 B2 | 3/2008 | Nunes et al. |
| 7,829,556 B2 | 11/2010 | Bemis et al. |
| 7,855,289 B2 | 12/2010 | Nunes et al. |
| 7,893,086 B2 | 2/2011 | Bemis et al. |
| 8,044,198 B2 | 10/2011 | Nunes et al. |
| 8,088,928 B2 | 1/2012 | Nunes et al. |
| 8,093,401 B2 | 1/2012 | Nunes et al. |
| 2001/0019823 A1 | 9/2001 | Schramm et al. |
| 2002/0061898 A1 | 5/2002 | Furneaux et al. |
| 2002/0132783 A1 | 9/2002 | Sauve et al. |
| 2003/0096830 A1 | 5/2003 | Furneaux et al. |
| 2003/0149261 A1 | 8/2003 | Schramm et al. |
| 2003/0229033 A1 | 12/2003 | Sauve et al. |
| 2004/0053944 A1 | 3/2004 | Furneaux et al. |
| 2004/0110772 A1 | 6/2004 | Furneaux et al. |
| 2004/0181063 A1 | 9/2004 | Furneaux et al. |
| 2004/0219565 A1 | 11/2004 | Kauppinen et al. |
| 2006/0014705 A1 | 1/2006 | Howitz et al. |
| 2010/0113542 A1* | 5/2010 | Eggenweiler ........ C07D 249/12 514/383 |
| 2013/0338178 A1 | 12/2013 | Shenk et al. |

FOREIGN PATENT DOCUMENTS

| | | | |
|---|---|---|---|
| WO | WO-97/12896 A1 | 4/1997 | |
| WO | WO-98/39352 A1 | 9/1998 | |
| WO | WO-99/14226 A2 | 3/1999 | |
| WO | WO-2007084162 A2 * | 7/2007 | .......... C07C 251/24 |
| WO | WO-2008/138943 A2 | 11/2008 | |
| WO | WO-2010/077642 A1 | 7/2010 | |

OTHER PUBLICATIONS

Michaelis et al. "The story of Human Cytomegalovirus and Cancer: Increasing Evidence and Open Questions," NEOPLASIA, 2009, vol. 11, No. 1, pp. 1-9.*

(56) References Cited

OTHER PUBLICATIONS

Lara et al. "Salermide, a sirtuin inhibitor with a strong cancer-specific proapoptotic effect," Oncogene, 2009, vol. 28, pp. 781-791.*
"Polynucleotides", pp. 858-859 IN: Kroschwitz (ed.), Concise Encyclopedia of Polymer Science and Engineering, John Wiley & Sons (1990).
Altschul et al., Basic local alignment search tool. J. Mol. Biol., 215: 403-10 (1990).
Asaba et al.,Inhibition of human sirtuins by in situ generation of an acetylated lysine-ADP-ribose conjugate, J. Am. Chem. Soc., 131(20):6989-96 (2009).
Bodner et al., Pharmacological promotion of inclusion formation: a therapeutic approach for Huntington's and Parkinson's diseases, Proc. Natl. Acad. Sci. USA, 103(11):4246-51 (2006).
Brummelkamp et al., A system for stable expression of short interfering RNAs in mammalian cells, Science, 296:550-3 (2002).
Carmins et al., Sirtuin activators: designing molecules to extend life span, Biochim. Biophys. Acta, 1799(10-12):740-9 (2010).
Cermak et al., Efficient design and assembly of custom TALEN and other TAL effector-based constructs for DNA targeting, Nucleic Acids Res., 39(12):e82 (2011).
Chakrabarty et al., Biochemical characterization of Plasmodium falciparum Sir2, a NAD+-dependent deacetylase, Mol. Biochem. Parasitol., 158(2):139-51 (2008).
Cobbs, Evolving evidence implicates cytomegalovirus as a promoter of malignant glioma pathogenesis, Herpesviridae, 2(1):10 (2011).
Cook, Medicinal chemistry of antisense oligonucleotides—future opportunities, Anti-Cancer Drug Design 6:585-607 (1991).
DeMesmaeker et al., Backbone modifications in oligonucleotides and peptide nucleic acid systems, Curr. Opin. Struct. Biol., 5: 343-55 (1995).
Docherty et al., Resveratrol inhibition of varicella-zoster virus replication in vitro, Antiviral Res., 72(3):171-7 (2006).
Englisch et al., Chemically Modified Oligonucleotides as Probes and Inhibitors. Angewandte Chemie, International Edition 1991; 30: 613-629.
Evers et al., 3,4',5-Trihydroxy-trans-stilbene (resveratrol) inhibits human cytomegalovirus replication and virus-induced cellular signaling, Antiviral Res., 63(2):85-95 (2004).
Freier et al., The ups and downs of nucleic acid duplex stability: structure-stability studies on chemically-modified DNA:RNA duplexes. Nucleic Acids Res. Nov. 15, 1997;25(22):4429-43.
Gambari et al., Targeting microRNAs involved in human diseases: a novel approach for modification of gene expression and drug development, Biochem. Pharmacol., 82(10):1416-29 (2011).
Gutierrez et al., Structural and synthetic investigations of tanikolide dimer, a SIRT2 selective inhibitor, and tanikolide seco-acid from the Madagascar marine cyanobacterium Lyngbya majuscula, J. Org. Chem., 74(15):5267-75 (2009).
Heltweg et al., Antitumor activity of a small-molecule inhibitor of human silent information regulator 2 enzymes, Cancer Res., 66(8):4368-77 (2006).
Howitz et al., Small molecule activators of sirtuins extend *Saccharomyces cerevisiae* lifespan, nature, 425(6954):191-6 (2003).
Huber et al., Novel 3-arylideneindolin-2-ones as inhibitors of NAD+-dependent histone deacetylases (sirtuins), J. Med. Chem., 53(3):1383-6 (2010).
International Preliminary Report on Patentability, International application No. PCT/US12/23621, dated Aug. 6, 2013.
International Search Report and Written Opinion, International application No. PCT/US12/23621, dated Jun. 28, 2012.
Kalle et al., Inhibition of SIRT1 by a small molecule induces apoptosis in breast cancer cells, Biochem. Biophys. Res. Commun., 401(1):13-9 (2010).
Katz, The reversible reaction of sodium thymonucleate and mercuric chloride, J. Am. Chem. Soc., 74:2238-46 (1952).
Kim et al., Tumor necrosis factor blockade and the risk of viral infection, Nat. Rev. Rheumatol., 6(3):165-74 (2010).
Kim et al., Virus-heat shock protein interaction and a novel axis for innate antiviral immunity, Cells, 1:646-66 (2012).
Kiviranta et al., N,N'-Bisbenzylidenebenzene-1,4-diamines and N,N'-Bisbenzylidenenaphthalene-1,4-diamines as Sirtuin Type 2 (SIRT2) Inhibitors, J. Med. Chem., 49(26):7907-11 (2006).
Kosturko et al., The crystal and molecular structure of a 2:1 complex of 1-methylthymine-mercury(II), Biochemistry, 13(19):3949-52 (1974).
Kwon et al., Human immunodeficiency virus type 1 Tat protein inhibits the SIRT1 deacetylase and induces T cell hyperactivation, Cell Host Microbe, 3(3):158-67 (2008).
Lawson et al., Inhibitors to understand molecular mechanisms of NAD(+)-dependent deacetylases (sirtuins), Biochim. Biophys. Acta, 1799(10-12): 726-39 (2010).
Lee et al., Expression of small interfering RNAs targeted against HIV-1 rev transcripts in human cells, Nat. Biotechnol., 20(5):500-5 (2002).
Li et al., p53-induced growth arrest is regulated by the mitochondrial SirT3 deacetylase, PLoS One, 5(5):e10486 (2010).
Mahajan et al., Sirtuin Modulators, IN: Yao et al. (eds.), Histone Deacetylases: the Biology and Clinical Implication, Springer-Verlag (2011).
Mai et al., Study of 1,4-dihydropyridine structural scaffold: discovery of novel sirtuin activators and inhibitors, J. Med. Chem., 52(17):5496-504 (2009).
Medda et al., Novel cambinol analogs as sirtuin inhibitors: synthesis, biological evaluation, and rationalization of activity, J. Med. Chem., 52(9):2673-82 (2009).
Miyagishi et al.,U6 promoter-driven siRNAs with four uridine 3' overhangs efficiently suppress targeted gene expression in mammalian cells, Nat. Biotechnol., 20(5):497-500 (2002).
Napper et al., Discovery of indoles as potent and selective inhibitors of the deacetylase SIRT1, J. Med. Chem., 48(25):8045-54 (2005).
Nayagam et al., SIRT1 modulating compounds from high-throughput screening as anti-inflammatory and insulin-sensitizing agents, J. Biomol. Screen., 11(8):959-67 (2006).
Neugebauer et al., Inhibitors of NAD+ dependent histone deacetylases (sirtuins), Curr. Pharm. Des., 14(6):562-73 (2008).
Nielsen et al., Sequence-selective recognition of DNA by strand displacement with a thymine-substituted polyamide. Science, 254: 1497-500 (1991).
Outeiro et al., Sirtuin 2 inhibitors rescue alpha-synuclein-mediated toxicity in models of Parkinson's disease, Science, 317(5837):516-9 (2007).
Paddison et al., Short hairpin RNAs (shRNAs) induce sequence-specific silencing in mammalian cells, Genes Dev., 16(8):948-58 (2002).
Paul et al., Effective expression of small interfering RNA in human cells, Nat. Biotechnol., 20(5):505-8 (2002).
Picchione et al., Viral genome silencing by neuronal sirtuin 1, J. Neurovirol., 17(2):184-8 (2011).
Sander et al., Selection-free zinc-finger-nuclease engineering by context-dependent assembly (CoDA), Nat. Methods, 8(1):67-9 (2011).
Sanders et al., Identification and characterization of novel sirtuin inhibitor scaffolds, Bioorg. Med. Chem., 17(19):7031-41 (2009).
Sanghvi, Y. S., Chapter 15, Antisense Research and Applications, pp. 274-288, Crooke, S. T. and Lebleu, B., ed., CRC Press, 1993.
Schlicker et al., Structure-based development of novel sirtuin inhibitors, Aging, 3(9):852-72 (2011).
Solomon et al., Inhibition of SIRT1 catalytic activity increases p53 acetylation but does not alter cell survival following DNA damage, Mol. Cell Biol., 26(1):28-38 (2006).
Sui et al., A DNA vector-based RNAi technology to suppress gene expression in mammalian cells, Proc. Natl. Acad. Sci. USA, 99(8):5515-20 (2002).
Szekeres et al., Resveratrol and resveratrol analogues—structure-activity relationship, Pharm. Res., 27(6)1 042-8 (2010).
Thomas, The interaction of $H_gCL_2$ with sodium thymonucleate, J. Am. Chem. Soc., 76:6032-4 (Dec. 5, 1954).
Tijsterman et al., RNA helicase MUT-14-dependent gene silencing triggered in C. elegans by short antisense RNAs, Science, 295(5555):694-7 (2002).

(56) References Cited

OTHER PUBLICATIONS

Trapp et al., Structure-activity studies on suramin analogues as inhibitors of NAD+-dependent histone deacetylases (sirtuins), ChemMedChem., 2(10)1 419-31 (2007).

Vickers et al., Efficient reduction of target RNAs by small interfering RNA and RNase H-dependent antisense agents. A comparative analysis, J. Biol. Chem., 278(9):7108-18 (2003).

Xu et al., miR-22 represses cancer progression by inducing cellular senescence, J. Cell Biol., 193(2):409-24 (2011).

Yamakuchi et al., miR-34a repression of SIRT1 regulates apoptosis, Proc. Natl. Acad. Sci. USA, 105(36):13421-6 (2008).

Yamane et al., On the complexing of deoxyribonucleic acid (DNA) by mercuric ion, J. Am. Chem. Soc., 83(12):2599-607 (1961).

Yang et al., Design and synthesis of compounds that extend yeast replicative lifespan, Aging Cell, 6(1):35-43 (2007).

Yasuda et al., Synthesis and characterization of SIRT6 protein coated magnetic beads: identification of a novel inhibitor of SIRT6 deacetylase from medicinal plant extracts, Anal. Chem., 83(19):7400-7 (2011).

Yu et al., RNA interference by expression of short-interfering RNAs and hairpin RNAs in mammalian cells, Proc. Natl. Acad. Sci. USA, 99(9):6047-52 (2002).

Zhang et al., An extremely stable and orthogonal DNA base pair with a simplified three-carbon backbone, J. Am. Chem. Soc., 127(1):74-5 (2005).

Zhang et al., Identification of a small molecule SIRT2 inhibitor with selective tumor cytotoxicity, Biochem. Biophys. Res. Commun., 386(4):729-33 (2009).

Zhang et al., PowerBLAST: a new network BLAST application for interactive or automated sequence analysis and annotation, Genome Res., 7(6):649-56 (1997).

Zhang et al., Resveratrol inhibited Tat-induced HIV-1 LTR transactivation via NAD(+)-dependent SIRT1 activity, Life Sci., 85(13-14):484-9 (2009).

Zimmermann et al., A novel silver(I)-mediated DNA base pair. J. Am. Chem. Soc., 124: 13684-5 (2002).

\* cited by examiner

SEQUENCE LISTING

```
<160> NUMBER OF SEQ ID NOS: 84

<210> SEQ ID NO 1
<211> LENGTH: 19
<212> TYPE: RNA
<213> ORGANISM: Artificial sequence
<220> FEATURE:
<223> OTHER INFORMATION: synthetic RNA

<400> SEQUENCE: 1
gugucauggu uccuuugca                                                  19

<210> SEQ ID NO 2
<211> LENGTH: 19
<212> TYPE: RNA
<213> ORGANISM: Artificial sequence
<220> FEATURE:
<223> OTHER INFORMATION: Synthetic RNA
```

```
<400> SEQUENCE: 2
ugcaaaggaa ccaugacac                                            19

<210> SEQ ID NO 3
<211> LENGTH: 19
<212> TYPE: RNA
<213> ORGANISM: Artificial sequence
<220> FEATURE:
<223> OTHER INFORMATION: Synthetic RNA

<400> SEQUENCE: 3
cugugaagcu guacgagga                                            19

<210> SEQ ID NO 4
<211> LENGTH: 19
<212> TYPE: RNA
<213> ORGANISM: Artificial sequence
<220> FEATURE:
<223> OTHER INFORMATION: Synthetic RNA

<400> SEQUENCE: 4
uccucguaca gcuucacag                                            19

<210> SEQ ID NO 5
<211> LENGTH: 19
<212> TYPE: RNA
<213> ORGANISM: Artificial sequence
<220> FEATURE:
<223> OTHER INFORMATION: Synthetic RNA

<400> SEQUENCE: 5
caacuauacc cagaacaua                                            19

<210> SEQ ID NO 6
<211> LENGTH: 19
<212> TYPE: RNA
<213> ORGANISM: Artificial sequence
<220> FEATURE:
<223> OTHER INFORMATION: Synthetic RNA

<400> SEQUENCE: 6
uauguucugg guauaguug                                            19

<210> SEQ ID NO 7
<211> LENGTH: 18
<212> TYPE: RNA
<213> ORGANISM: Artificial sequence
<220> FEATURE:
<223> OTHER INFORMATION: Synthetic RNA

<400> SEQUENCE: 7
cuacuccugc gugcuaca                                             18

<210> SEQ ID NO 8
<211> LENGTH: 19
<212> TYPE: RNA
<213> ORGANISM: Artificial sequence
<220> FEATURE:
<223> OTHER INFORMATION: Synthetic RNA

<400> SEQUENCE: 8
uguagcagcg caggaguag                                            19
```

```
<210> SEQ ID NO 9
<211> LENGTH: 19
<212> TYPE: RNA
<213> ORGANISM: Artificial sequence
<220> FEATURE:
<223> OTHER INFORMATION: Synthetic RNA

<400> SEQUENCE: 9
ggaguaaccu cccucaucu                                                    19

<210> SEQ ID NO 10
<211> LENGTH: 19
<212> TYPE: RNA
<213> ORGANISM: Artificial sequence
<220> FEATURE:
<223> OTHER INFORMATION: Synthetic RNA

<400> SEQUENCE: 10
agaugaggga gguuacucc                                                    19

<210> SEQ ID NO 11
<211> LENGTH: 19
<212> TYPE: RNA
<213> ORGANISM: Artificial sequence
<220> FEATURE:
<223> OTHER INFORMATION: Synthetic RNA

<400> SEQUENCE: 11
cgcguuucuu cuccuguau                                                    19

<210> SEQ ID NO 12
<211> LENGTH: 19
<212> TYPE: RNA
<213> ORGANISM: Artificial sequence
<220> FEATURE:
<223> OTHER INFORMATION: Synthetic RNA

<400> SEQUENCE: 12
auacaggaga agaaacgcg                                                    19

<210> SEQ ID NO 13
<211> LENGTH: 19
<212> TYPE: RNA
<213> ORGANISM: Artificial sequence
<220> FEATURE:
<223> OTHER INFORMATION: Synthetic RNA

<400> SEQUENCE: 13
gcuuucugug ccuaguuga                                                    19

<210> SEQ ID NO 14
<211> LENGTH: 19
<212> TYPE: RNA
<213> ORGANISM: Artificial sequence
<220> FEATURE:
<223> OTHER INFORMATION: Synthetic RNA

<400> SEQUENCE: 14
ucaacuaggc acagaaagc                                                    19

<210> SEQ ID NO 15
<211> LENGTH: 19
<212> TYPE: RNA
<213> ORGANISM: Artificial sequence
<220> FEATURE:
<223> OTHER INFORMATION: Synthetic RNA
```

```
<400> SEQUENCE: 15
agcuucaacc agcuuugag                                              19

<210> SEQ ID NO 16
<211> LENGTH: 19
<212> TYPE: RNA
<213> ORGANISM: Artificial sequence
<220> FEATURE:
<223> OTHER INFORMATION: Synthetic RNA

<400> SEQUENCE: 16
agcuucaacc agcuuugag                                              19

<210> SEQ ID NO 17
<211> LENGTH: 19
<212> TYPE: RNA
<213> ORGANISM: Artificial sequence
<220> FEATURE:
<223> OTHER INFORMATION: Synthetic RNA

<400> SEQUENCE: 17
gacaagaccu caugccuga                                              19

<210> SEQ ID NO 18
<211> LENGTH: 19
<212> TYPE: RNA
<213> ORGANISM: Artificial sequence
<220> FEATURE:
<223> OTHER INFORMATION: Synthetic RNA

<400> SEQUENCE: 18
ucaggcauga ggucuuguc                                              19

<210> SEQ ID NO 19
<211> LENGTH: 19
<212> TYPE: RNA
<213> ORGANISM: Artificial sequence
<220> FEATURE:
<223> OTHER INFORMATION: Synthetic RNA

<400> SEQUENCE: 19
gggaucaucc uugcaggua                                              19

<210> SEQ ID NO 20
<211> LENGTH: 19
<212> TYPE: RNA
<213> ORGANISM: Artificial sequence
<220> FEATURE:
<223> OTHER INFORMATION: Synthetic RNA

<400> SEQUENCE: 20
uaccugcaag gaugauccc                                              19

<210> SEQ ID NO 21
<211> LENGTH: 19
<212> TYPE: RNA
<213> ORGANISM: Artificial sequence
<220> FEATURE:
<223> OTHER INFORMATION: Synthetic RNA

<400> SEQUENCE: 21
gagaaacucg gaaagcugu                                              19
```

```
<210> SEQ ID NO 22
<211> LENGTH: 19
<212> TYPE: RNA
<213> ORGANISM: Artificial sequence
<220> FEATURE:
<223> OTHER INFORMATION: Synthetic RNA

<400> SEQUENCE: 22
acagcuuucc gaguuucuc                                                  19

<210> SEQ ID NO 23
<211> LENGTH: 19
<212> TYPE: RNA
<213> ORGANISM: Artificial sequence
<220> FEATURE:
<223> OTHER INFORMATION: Synthetic RNA

<400> SEQUENCE: 23
cuuugagcac cugggagaa                                                  19

<210> SEQ ID NO 24
<211> LENGTH: 19
<212> TYPE: RNA
<213> ORGANISM: Artificial sequence
<220> FEATURE:
<223> OTHER INFORMATION: Synthetic RNA

<400> SEQUENCE: 24
uucucccagg ugcucaaag                                                  19

<210> SEQ ID NO 25
<211> LENGTH: 19
<212> TYPE: RNA
<213> ORGANISM: Artificial sequence
<220> FEATURE:
<223> OTHER INFORMATION: Synthetic RNA

<400> SEQUENCE: 25
gugagacccg gcugggcaa                                                  19

<210> SEQ ID NO 26
<211> LENGTH: 19
<212> TYPE: RNA
<213> ORGANISM: Artificial sequence
<220> FEATURE:
<223> OTHER INFORMATION: Synthetic RNA

<400> SEQUENCE: 26
uugcccagcc gggucucac                                                  19

<210> SEQ ID NO 27
<211> LENGTH: 19
<212> TYPE: RNA
<213> ORGANISM: Artificial sequence
<220> FEATURE:
<223> OTHER INFORMATION: Synthetic RNA

<400> SEQUENCE: 27
cagcauccca guugagaaa                                                  19

<210> SEQ ID NO 28
<211> LENGTH: 19
<212> TYPE: RNA
<213> ORGANISM: Artificial sequence
<220> FEATURE:
<223> OTHER INFORMATION: Synthetic RNA
```

<400> SEQUENCE: 28
uuucucaacu gggaugcug					19

<210> SEQ ID NO 29
<211> LENGTH: 19
<212> TYPE: RNA
<213> ORGANISM: Artificial sequence
<220> FEATURE:
<223> OTHER INFORMATION: Synthetic RNA

<400> SEQUENCE: 29
gagauccaug guagcuuau					19

<210> SEQ ID NO 30
<211> LENGTH: 19
<212> TYPE: RNA
<213> ORGANISM: Artificial sequence
<220> FEATURE:
<223> OTHER INFORMATION: Synthetic RNA

<400> SEQUENCE: 30
auaagcuacc auggaucuc					19

<210> SEQ ID NO 31
<211> LENGTH: 19
<212> TYPE: RNA
<213> ORGANISM: Artificial sequence
<220> FEATURE:
<223> OTHER INFORMATION: Synthetic RNA

<400> SEQUENCE: 31
cuguccauca cgcugggua					19

<210> SEQ ID NO 32
<211> LENGTH: 19
<212> TYPE: RNA
<213> ORGANISM: Artificial sequence
<220> FEATURE:
<223> OTHER INFORMATION: Synthetic RNA

<400> SEQUENCE: 32
uacccagcgu gauggacag					19

<210> SEQ ID NO 33
<211> LENGTH: 19
<212> TYPE: RNA
<213> ORGANISM: Artificial sequence
<220> FEATURE:
<223> OTHER INFORMATION: Synthetic RNA

<400> SEQUENCE: 33
cucacuuugu uacuuguuu					19

<210> SEQ ID NO 34
<211> LENGTH: 19
<212> TYPE: RNA
<213> ORGANISM: Artificial sequence
<220> FEATURE:
<223> OTHER INFORMATION: Synthetic RNA

<400> SEQUENCE: 34
aaacaaguaa caaagugag					19

```
<210> SEQ ID NO 35
<211> LENGTH: 19
<212> TYPE: RNA
<213> ORGANISM: Artificial sequence
<220> FEATURE:
<223> OTHER INFORMATION: Synthetic RNA

<400> SEQUENCE: 35
ccaaguguaa gacgcagua                                                    19

<210> SEQ ID NO 36
<211> LENGTH: 19
<212> TYPE: RNA
<213> ORGANISM: Artificial sequence
<220> FEATURE:
<223> OTHER INFORMATION: Synthetic RNA

<400> SEQUENCE: 36
uacugcgucu uacacuugg                                                    19

<210> SEQ ID NO 37
<211> LENGTH: 19
<212> TYPE: RNA
<213> ORGANISM: Artificial sequence
<220> FEATURE:
<223> OTHER INFORMATION: Synthetic RNA

<400> SEQUENCE: 37
gggaguacgu gcgggvguu                                                    19

<210> SEQ ID NO 38
<211> LENGTH: 19
<212> TYPE: RNA
<213> ORGANISM: Artificial sequence
<220> FEATURE:
<223> OTHER INFORMATION: Synthetic RNA

<400> SEQUENCE: 38
aacacccgca cguacuccc                                                    19

<210> SEQ ID NO 39
<211> LENGTH: 19
<212> TYPE: RNA
<213> ORGANISM: Artificial sequence
<220> FEATURE:
<223> OTHER INFORMATION: Synthetic RNA

<400> SEQUENCE: 39
gacguaauca cgugcucga                                                    19

<210> SEQ ID NO 40
<211> LENGTH: 19
<212> TYPE: RNA
<213> ORGANISM: Artificial sequence
<220> FEATURE:
<223> OTHER INFORMATION: Synthetic RNA

<400> SEQUENCE: 40
ucgagcacgu gauuacguc                                                    19

<210> SEQ ID NO 41
<211> LENGTH: 19
<212> TYPE: RNA
<213> ORGANISM: Artificial sequence
<220> FEATURE:
<223> OTHER INFORMATION: Synthetic RNA
```

<400> SEQUENCE: 41
gacgucaugc ggcuccuca                                                19

<210> SEQ ID NO 42
<211> LENGTH: 19
<212> TYPE: RNA
<213> ORGANISM: Artificial sequence
<220> FEATURE:
<223> OTHER INFORMATION: Syntheric RNA

<400> SEQUENCE: 42
ugaggagccg caugacguc                                                19

<210> SEQ ID NO 43
<211> LENGTH: 57
<212> TYPE: DNA
<213> ORGANISM: Homo sapiens

<400> SEQUENCE: 43
ccgggcaaag cctttctgaa tctatctcga gatagattca gaaaggcttt gctttttt    57

<210> SEQ ID NO 44
<211> LENGTH: 57
<212> TYPE: DNA
<213> ORGANISM: Homo sapiens

<400> SEQUENCE: 44
ccggcctcga acaattctta aagatctcga gatctttaag aattgttcga ggttttt    57

<210> SEQ ID NO 45
<211> LENGTH: 57
<212> TYPE: DNA
<213> ORGANISM: Homo sapiens

<400> SEQUENCE: 45
ccgggcggga atccaaagga taattctcga gaattatcct ttggattccc gctttttt    57

<210> SEQ ID NO 46
<211> LENGTH: 58
<212> TYPE: DNA
<213> ORGANISM: Mus musculus

<400> SEQUENCE: 46
ccggagtgag accagtagca ctaatctcga gattagtgct actggtctca cttttttg   58

<210> SEQ ID NO 47
<211> LENGTH: 58
<212> TYPE: DNA
<213> ORGANISM: Mus musculus

<400> SEQUENCE: 47
ccgggccatg tttgatattg agtatctcga gatactcaat atcaaacatg gctttttg   58

<210> SEQ ID NO 48
<211> LENGTH: 58
<212> TYPE: DNA
<213> ORGANISM: Mus musculus

<400> SEQUENCE: 48
ccgggagggt aatcaatacc tgtttctcga gaaacaggta ttgattaccc tctttttg   58

<210> SEQ ID NO 49
<211> LENGTH: 58
<212> TYPE: DNA
<213> ORGANISM: Homo sapiens

<400> SEQUENCE: 49
ccggtatgac aacctagaga agtacctcga ggtacttctc taggttgtca tattttg    58

<210> SEQ ID NO 50
<211> LENGTH: 58
<212> TYPE: DNA
<213> ORGANISM: Homo sapiens

<400> SEQUENCE: 50
ccggcagaag acattgctta ttggactcga gtccaataag caatgtcttc tgttttg    58

<210> SEQ ID NO 51
<211> LENGTH: 58
<212> TYPE: DNA
<213> ORGANISM: Homo sapiens

<400> SEQUENCE: 51
ccggcctgtg gctaagtaaa ccatactcga gtatggttta cttagccaca ggttttg    58

<210> SEQ ID NO 52
<211> LENGTH: 57
<212> TYPE: DNA
<213> ORGANISM: Mus musculus

<400> SEQUENCE: 52
ccggccttcg ttctttaacc actttctcga gaaagtggtt aaagaacgaa ggttttt    57

<210> SEQ ID NO 53
<211> LENGTH: 57
<212> TYPE: DNA
<213> ORGANISM: Mus musculus

<400> SEQUENCE: 53
ccggcctcta tgcaaacctg gagaactcga gttctccagg tttgcataga ggttttt    57

<210> SEQ ID NO 54
<211> LENGTH: 57
<212> TYPE: DNA
<213> ORGANISM: Mus musculus

<400> SEQUENCE: 54
ccggcggctg ctcattaaca aggaactcga gttccttgtt aatgagcagc cgttttt    57

<210> SEQ ID NO 55
<211> LENGTH: 58
<212> TYPE: DNA
<213> ORGANISM: Homo sapiens

<400> SEQUENCE: 55
ccggcccaac gtcactcact actttctcga gaaagtagtg agtgacgttg ggttttg    58

<210> SEQ ID NO 56
<211> LENGTH: 58
<212> TYPE: DNA
<213> ORGANISM: Homo sapiens

<400> SEQUENCE: 56
ccgggcggct ctacacgcag aacatctcga gatgttctgc gtgtagagcc gcttttg    58

-continued

```
<210> SEQ ID NO 57
<211> LENGTH: 58
<212> TYPE: DNA
<213> ORGANISM: Homo sapiens

<400> SEQUENCE: 57
ccgggtgggt gcttcaagtg ttgttctcga gaacaacact tgaagcaccc acttttttg      58

<210> SEQ ID NO 58
<211> LENGTH: 58
<212> TYPE: DNA
<213> ORGANISM: Mus musculus

<400> SEQUENCE: 58
ccggcctact ccatatggct gacttctcga gaagtcagcc atatggagta ggttttttg      58

<210> SEQ ID NO 59
<211> LENGTH: 58
<212> TYPE: DNA
<213> ORGANISM: Mus musculus

<400> SEQUENCE: 59
ccggagacag ctccaacacg tttacctcga ggtaaacgtg ttggagctgt ctttttttg      58

<210> SEQ ID NO 60
<211> LENGTH: 58
<212> TYPE: DNA
<213> ORGANISM: Mus musculus

<400> SEQUENCE: 60
ccgggcccaa tgtcactcac tacttctcga gaagtagtga gtgacattgg gcttttttg      58

<210> SEQ ID NO 61
<211> LENGTH: 57
<212> TYPE: DNA
<213> ORGANISM: Homo sapiens

<400> SEQUENCE: 61
ccggcccgat tgcaatactg aacatctcga gatgttcagt attgcaatcg ggttttt       57

<210> SEQ ID NO 62
<211> LENGTH: 57
<212> TYPE: DNA
<213> ORGANISM: Homo sapiens

<400> SEQUENCE: 62
ccggccgtgc tcgaaagcct ccattctcga gaatggaggc tttcgagcac ggttttt       57

<210> SEQ ID NO 63
<211> LENGTH: 57
<212> TYPE: DNA
<213> ORGANISM: Homo sapiens

<400> SEQUENCE: 63
ccgggaaccc tgacaaggtt gatttctcga gaaatcaacc ttgtcagggt tcttttt       57

<210> SEQ ID NO 64
<211> LENGTH: 62
<212> TYPE: DNA
<213> ORGANISM: Mus musculus
```

<400> SEQUENCE: 64
gtaccggagt aaaccacaac tgtctatgct cgagcataga cagttgtggt ttactttttt    60
tg                                                                  62

<210> SEQ ID NO 65
<211> LENGTH: 58
<212> TYPE: DNA
<213> ORGANISM: Mus musculus

<400> SEQUENCE: 65
ccgggcagca tatccggaac cttaactcga gttaaggttc cggatatgct gctttttg     58

<210> SEQ ID NO 66
<211> LENGTH: 58
<212> TYPE: DNA
<213> ORGANISM: Mus musculus

<400> SEQUENCE: 66
ccggttgact ttcaggccga caaagctcga gctttgtcgg cctgaaagtc aatttttg     58

<210> SEQ ID NO 67
<211> LENGTH: 57
<212> TYPE: DNA
<213> ORGANISM: Homo sapiens

<400> SEQUENCE: 67
ccgggagtcc aatttgtcca gctttctcga gaaagctgga caaattggac tctttttt     57

<210> SEQ ID NO 68
<211> LENGTH: 57
<212> TYPE: DNA
<213> ORGANISM: Homo sapiens

<400> SEQUENCE: 68
ccgggctacg aacagattca ggtttctcga gaaacctgaa tctgttcgta gctttttt     57

<210> SEQ ID NO 69
<211> LENGTH: 57
<212> TYPE: DNA
<213> ORGANISM: Homo sapiens

<400> SEQUENCE: 69
ccggcgtcca cacgaaacca gatttctcga gaaatctggt ttcgtgtgga cgtttttt     57

<210> SEQ ID NO 70
<211> LENGTH: 58
<212> TYPE: DNA
<213> ORGANISM: Mus musculus

<400> SEQUENCE: 70
ccgggcagac aatctgttac gtgatctcga gatcacgtaa cagattgtct gctttttg     58

<210> SEQ ID NO 71
<211> LENGTH: 58
<212> TYPE: DNA
<213> ORGANISM: Mus musculus

<400> SEQUENCE: 71
ccggccagtt gtgttgtaga cgaaactcga gtttcgtcta caacacaact ggtttttg     58

<210> SEQ ID NO 72
<211> LENGTH: 58
<212> TYPE: DNA
<213> ORGANISM: Mus musculus

<400> SEQUENCE: 72
ccggcgacag attcaggttt catttctcga gaaatgaaac ctgaatctgt cgtttttg    58

<210> SEQ ID NO 73
<211> LENGTH: 58
<212> TYPE: DNA
<213> ORGANISM: Homo sapiens

<400> SEQUENCE: 73
ccggtggaag aatgtgccaa gtgtactcga gtacacttgg cacattcttc catttttg    58

<210> SEQ ID NO 74
<211> LENGTH: 58
<212> TYPE: DNA
<213> ORGANISM: Homo sapiens

<400> SEQUENCE: 74
ccgggcagtc ttccagtgtg gtgttctcga gaacaccaca ctggaagact gctttttg    58

<210> SEQ ID NO 75
<211> LENGTH: 58
<212> TYPE: DNA
<213> ORGANISM: Homo sapiens

<400> SEQUENCE: 75
ccgggctggg tacatcgctg cagatctcga gatctgcagc gatgtaccca gctttttg    58

<210> SEQ ID NO 76
<211> LENGTH: 58
<212> TYPE: DNA
<213> ORGANISM: Mus musculus

<400> SEQUENCE: 76
ccggcatgtc caacacagct cctttctcga gaaaggagct gtgttggaca tgtttttg    58

<210> SEQ ID NO 77
<211> LENGTH: 58
<212> TYPE: DNA
<213> ORGANISM: Mus musculus

<400> SEQUENCE: 77
ccgggcatgt ttcgtataag tccaactcga gttggactta tacgaaacat gctttttg    58

<210> SEQ ID NO 78
<211> LENGTH: 58
<212> TYPE: DNA
<213> ORGANISM: Mus musculus

<400> SEQUENCE: 78
ccgggtttga caccaccttc gagaactcga gttctcgaag gtggtgtcaa actttttg    58

<210> SEQ ID NO 79
<211> LENGTH: 58
<212> TYPE: DNA
<213> ORGANISM: Homo sapiens

<400> SEQUENCE: 79
ccgggtccag cctgaaggtt ctaaactcga gtttagaacc ttcaggctgg actttttg    58

```
<210> SEQ ID NO 80
<211> LENGTH: 57
<212> TYPE: DNA
<213> ORGANISM: Homo sapiens

<400> SEQUENCE: 80
ccggcgccaa atacttggtc gtctactcga gtagacgacc aagtatttgg cgttttt         57

<210> SEQ ID NO 81
<211> LENGTH: 57
<212> TYPE: DNA
<213> ORGANISM: Homo sapiens

<400> SEQUENCE: 81
ccgggcctga aggttctaaa gaagtctcga gacttcttta gaaccttcag gcttttt         57

<210> SEQ ID NO 82
<211> LENGTH: 58
<212> TYPE: DNA
<213> ORGANISM: Mus musculus

<400> SEQUENCE: 82
ccggcctccc tctttctact ccttactcga gtaaggagta gaaagaggga ggtttttg        58

<210> SEQ ID NO 83
<211> LENGTH: 58
<212> TYPE: DNA
<213> ORGANISM: Mus musculus

<400> SEQUENCE: 83
ccggtgcatc cctaacagag agtatctcga gatactctct gttagggatg catttttg        58

<210> SEQ ID NO 84
<211> LENGTH: 58
<212> TYPE: DNA
<213> ORGANISM: Mus musculus

<400> SEQUENCE: 84
ccggcctgga gattcctgtc tacaactcga gttgtagaca ggaatctcca ggtttttg        58
```

SIRTUIN MODULATORS AS INHIBITORS OF CYTOMEGALOVIRUS

CROSS-REFERENCE TO RELATED APPLICATIONS

This application is a continuation of U.S. patent application Ser. No. 13/982,779, filed Sep. 9, 2013, now abandoned, which is a National Phase Application of PCT/US2012/023621, filed Feb. 2, 2012, which claims priority under Section 119(e) from U.S. Provisional Application No. 61/438,846, filed Feb. 2, 2011, and U.S. Provisional Application No. 61/527,102, filed Aug. 24, 2011 is claimed, the disclosures of which are incorporated by reference in their entirety.

STATEMENT OF U.S. GOVERNMENT INTEREST

This invention was made with government support under Grant Nos. DA026192 and CA085786 awarded by the National Institutes of Health. The government has certain rights in the invention.

BACKGROUND

Humans express seven sirtuins, termed SIRT1-7, all of which contain a conserved central NAD+-binding and catalytic domain. Sirtuins are NAD+-dependent deacetylases and ADP-ribosyltransferases. Sirtuins deacetylate acyl-lysine residues of histones and other proteins. Given their requirement for NAD+, sirtuins are regulated by the pathways that produce the cofactor, and, as a result, are responsive to the metabolic state of cells. While their expression profiles can vary, sirtuins are ubiquitously expressed in a wide range of tissues. Sirtuins are found in different cellular compartments: SIRT1, 6 and 7 are predominantly nuclear; SIRT3-5 are mitochondrial; and SIRT2 is a predominantly cytoplasmic resident. Drugs that activate sirtuins, such as resveratrol, appear to be well tolerated.

There have been several reports relating to the effects of resveratrol and SIRT1 on viruses or expression from viral promoters. For example: Resveratrol has been reported to inhibit varicella zoster virus replication in cultured cells (Docherty et al., 2006, Antiviral Res 72, 171-7); Resveratrol or overexpression of SIRT1 have been reported to inhibit the transactivation of the HIV-1 LTR in a transfection assay performed in cultured cells (Zhang et al., 2009, Life Sciences 85, 484-9); Resveratrol, SRT1720 or overexpression of SIRT1 have been reported to inhibit transgene expression from a replication-defective adenovirus in cultured neuronal cells (Picchione and Bhattacharjee, 2011, J Neurovirol, 17, 184-8); and HIV-1 Tat protein has been shown to negatively regulate SIRT1 (Kwon et al., 2008, Cell Host Microbe 3, 158-67).

SUMMARY

In an aspect, the invention relates to a composition comprising a one or more sirtuin agonists. Sirtuin agonists can be polyhydroxy stilbene compounds, polyhydroxy flavonoids (e.g., flavones, flavonols, isoflavones, or the like), polyhydroxy chalcone compounds, or combinations thereof. Specific examples of contemplated agonists include:

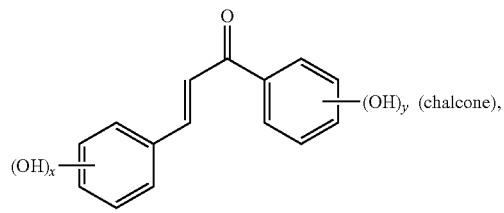

wherein x and y are each 0, 1, 2, 3, 4, or 5, and x+y≥1;

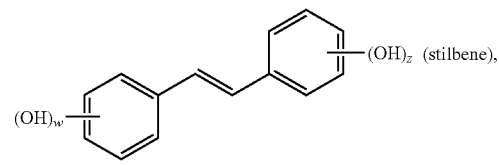

wherein w and z are each 0, 1, 2, 3, 4, or 5, and w+z≥1;

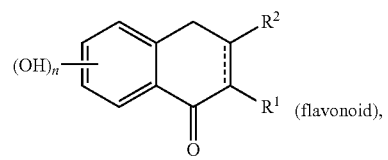

wherein $R^1$ is H or OH and $R^2$ is

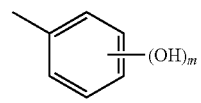

or $R^1$ is

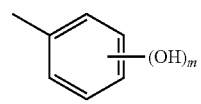

and $R^2$ is H or OH; n and m are each 0, 1, 2, 3, 4, or 5, n+m≥1, and the dashed line indicates an optional double bond. Also specifically contemplated are sirtuin 5 agonists, such as 3,5-dihydroxy-4'-chloro-trans-stilbene, dipyridamole, 3,5-dihydroxy-4'ethyl-trans-stilbene, 3,5-dihydroxy-4'-isopropyl-trans-stilbene, 3,5-dihydroxy-4'-methyl-trans-stilbene, resveratrol, 3,5-dihydroxy-4'thiomethyl-trans-stilbene, 3,5-dihydroxy-4'-carbomethoxy-trans-stilbene, isoliquiritgenin, 3,5-dihydro-4'nitro-trans-stilbene, 3,5-dihydroxy-4'azido-trans-stilbene, piceatannol, 3-methoxy-5-hydroxy-4'acetamido-trans-stilbene, 3,5-dihydroxy-4'-acetoxy-trans-stilbene, pinosylvin, fisetin, (E)-1-(3,5-dihydrophenyl)-2-(4-pyridyl)ethene, (E)-1-(3,5-dihydrophenyl)-2-(2-napthyl)ethene, 3,5-dihydroxy-4'-acetamide-trans-stilbene, butein, quercetin, 3,5-dihydroxy-4'-thioethyl-trans-stilbene), 3,5-dihydroxy-4'carboxy-trans-stilbene, and/or 3,4'-dihydroxy-5-acetoxy-trans-stilbene. Such agonists are described in US Patent Publication No. 2006/0014705, incorporated by reference in its entirety.

In an aspect, the invention relates to a composition comprising one or more sirtuin antagonists, or two or more sirtuin antagonists. Specifically contemplated SIRT1/SIRT2 dual inhibitors include cambinol, tenovin 1, tenovin 6, salermide, sirtinol, and combinations thereof. Also contemplated are compositions comprising a SIRT1 inhibitor and a SIRT2 inhibitor. Further contemplated are compositions comprising a SIRT1 inhibitor and one or more of the group comprising a SIRT2 inhibitor, a SIRT3 inhibitor, a SIRT4 inhibitor, a SIRT5 inhibitor, a SIRT6 inhibitor, and a SIRT7 inhibitor. SIRT inhibitors are readily identified through a screening assay.

In one aspect, disclosed herein are methods of inhibiting both SIRT1 and SIRT2 comprising contacting both SIRT1 and SIRT2 with one or more antagonist compounds. In various cases, the antagonist (e.g., a SIRT1/SIRT2 dual inhibitor or a SIRT1 inhibitor and a SIRT2 inhibitor) is cambinol, tenovin 1, tenovin 6, salermide, sirtinol, or combinations thereof, or is one or more compounds as detailed below. Further disclosed is a method of inhibiting virus production comprising contacting a virus-infected cell with a SIRT1/SIRT2 dual inhibitor or a combination of a SIRT1 inhibitor and a SIRT2 inhibitor.

Further disclosed are methods of inhibiting virus production comprising contacting a virus-infected cell with one or more inhibitors of two or more sirtuins, e.g., inhibiting SIRT1 and SIRT2; SIRT1 and SIRT3; SIRT1 and SIRT4; SIRT1 and SIRT5; SIRT1 and SIRT6; SIRT1 and SIRT7; SIRT2 and SIRT3; SIRT2 and SIRT4; SIRT2 and SIRT5; SIRT2 and SIRT6; SIRT2 and SIRT7; SIRT3 and SIRT4; SIRT3 and SIRT5; SIRT3 and SIRT6; SIRT3 and SIRT7; SIRT4 and SIRT5; SIRT4 and SIRT6; SIRT4 and SIRT7; SIRT5 and SIRT6; SIRT5 and SIRT7; and SIRT6 and SIRT7. Also disclosed are methods of inhibiting three or more sirtuins (e.g., non-limiting examples include inhibiting SIRT1, SIRT2, and SIRT3; inhibiting SIRT1, SIRT2, and SIRT5; and inhibiting SIRT1, SIRT3, and SIRT5). The inhibitors can be the same, or can be different (e.g., an inhibitor to both SIRT2 and SIRT3 or a SIRT2 inhibitor and a SIRT3 inhibitor). Also contemplated are methods of inhibiting virus production comprising containing a virus-infected cell with one or more inhibitors of three or more sirtuins.

In an aspect, the invention relates to a composition comprising one or more sirtuin antagonists that decreases the activity of both or each of SIRT1 and SIRT2. In some cases, the composition comprises a first compound that is a SIRT1 antagonist and a second compound that is a SIRT2 antagonist. Further disclosed are compositions comprising inhibitors of two or more sirtuins, e.g., inhibiting SIRT1 and SIRT2; SIRT1 and SIRT3; SIRT1 and SIRT4; SIRT1 and SIRT5; SIRT1 and SIRT6; SIRT1 and SIRT7; SIRT2 and SIRT3; SIRT2 and SIRT4; SIRT2 and SIRT5; SIRT2 and SIRT6; SIRT2 and SIRT7; SIRT3 and SIRT4; SIRT3 and SIRT5; SIRT3 and SIRT6; SIRT3 and SIRT7; SIRT4 and SIRT5; SIRT4 and SIRT6; SIRT4 and SIRT7; SIRT5 and SIRT6; SIRT5 and SIRT7; and SIRT6 and SIRT7. Also specifically disclosed are compositions comprising inhibitors of three or more sirtuins (e.g., non-limiting examples include SIRT1, SIRT2, and SIRT3 inhibitors; SIRT1, SIRT2, and SIRT5 inhibitors; and SIRT1, SIRT3, and SIRT5 inhibitors). The inhibitors can be the same, or can be different (e.g., an inhibitor to both SIRT2 and SIRT3 or a SIRT2 inhibitor and a SIRT3 inhibitor).

In an aspect, the invention relates to a pharmaceutical composition including any of the compositions herein and a pharmaceutically acceptable carrier.

In an aspect, the invention relates to a method of treating disease comprising administering any of the compositions or pharmaceutical compositions herein to a patient, e.g., a patient suffering from a viral infection or a disorder associated with a viral infection.

BRIEF DESCRIPTION OF THE FIGURES

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

DETAILED DESCRIPTION

Figure 1:
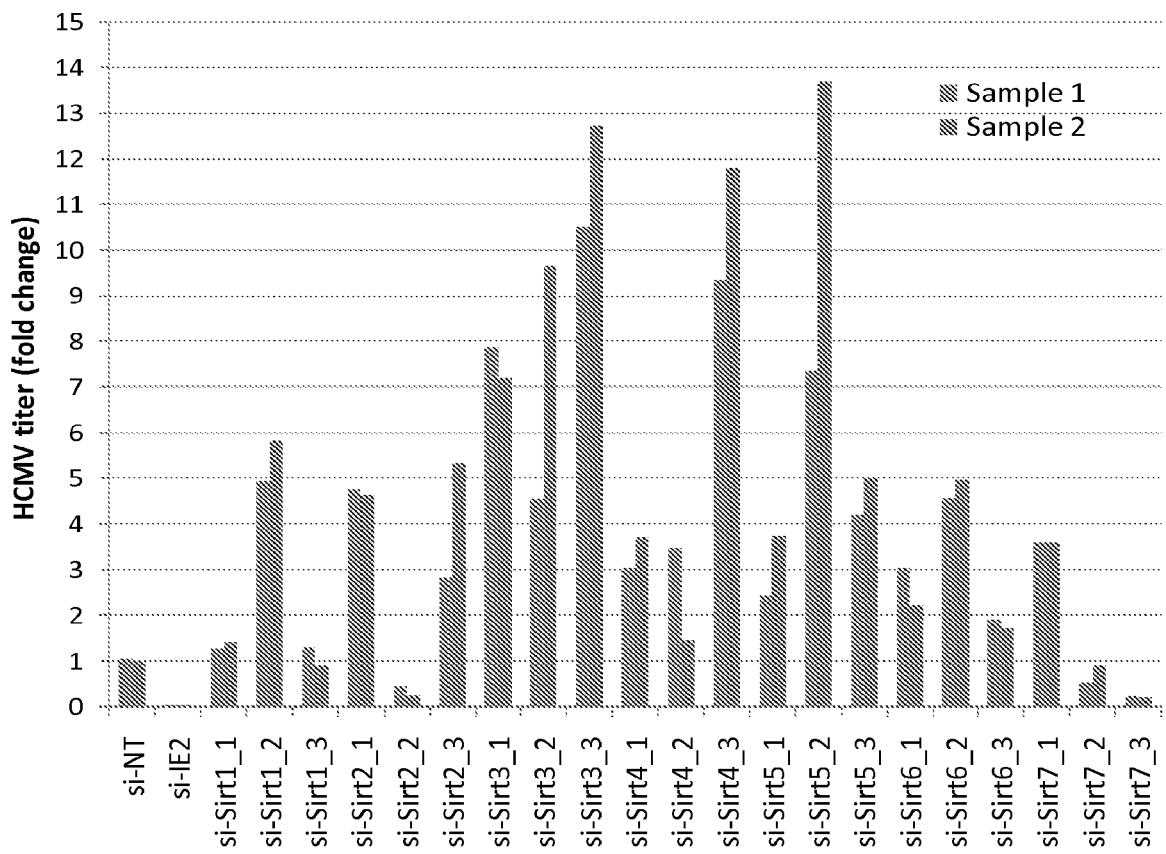
FIG. 1 illustrates that inhibition of sirtuins enhances the production of infectious human cytomegalovirus (HCMV) progeny.

Certain terminology is used in the following description for convenience only and is not limiting. The words "right," "left," "top," and "bottom" designate directions in the drawings to which reference is made.

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Referring to FIG. 1, MRC5 fibroblasts were transfected with three different siRNAs targeting each of the seven sirtuins. 24 hours later, cells were infected with the HCMV AD169 strain at a multiplicity of 0.5 IU/cell, and the yield of HCMV was determined at 96 hpi. Sample 1 (left bar above each siRNA label) and sample 2 (right bar above each siRNA label) represent two independent knockdown experiments. As illustrated, siRNA-mediated inhibition of each of the seven sirtuins augments the production of HCMV progeny in cultured fibroblasts.

Figure 2:
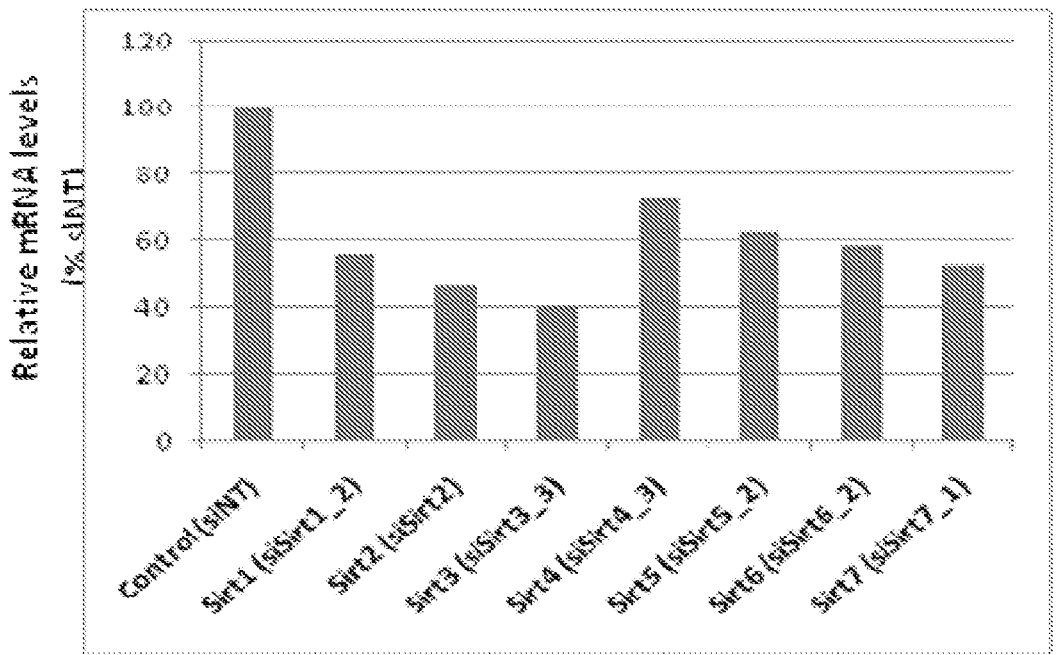
FIG. 2 illustrates that the siRNAs used effectively reduced the levels of target sirtuin RNAs.

Referring to FIG. 2, MRC5 cells were transfected with the indicated siRNAs; 24 hours later, cells were infected with the HCMV AD169 strain at a multiplicity of 0.5 IU/cell, and at 72 hpi the levels of sirtuin RNAs was determined by quantitative RT-qPCR by using GAPDH as the comparator. The level of knockdown induced by the siRNA that caused the greatest increase in virus yield for each sirtuin was monitored by quantitative RT-PCR, and each of the siRNAs proved to reduce the level of the targeted RNA.

Figure 3:
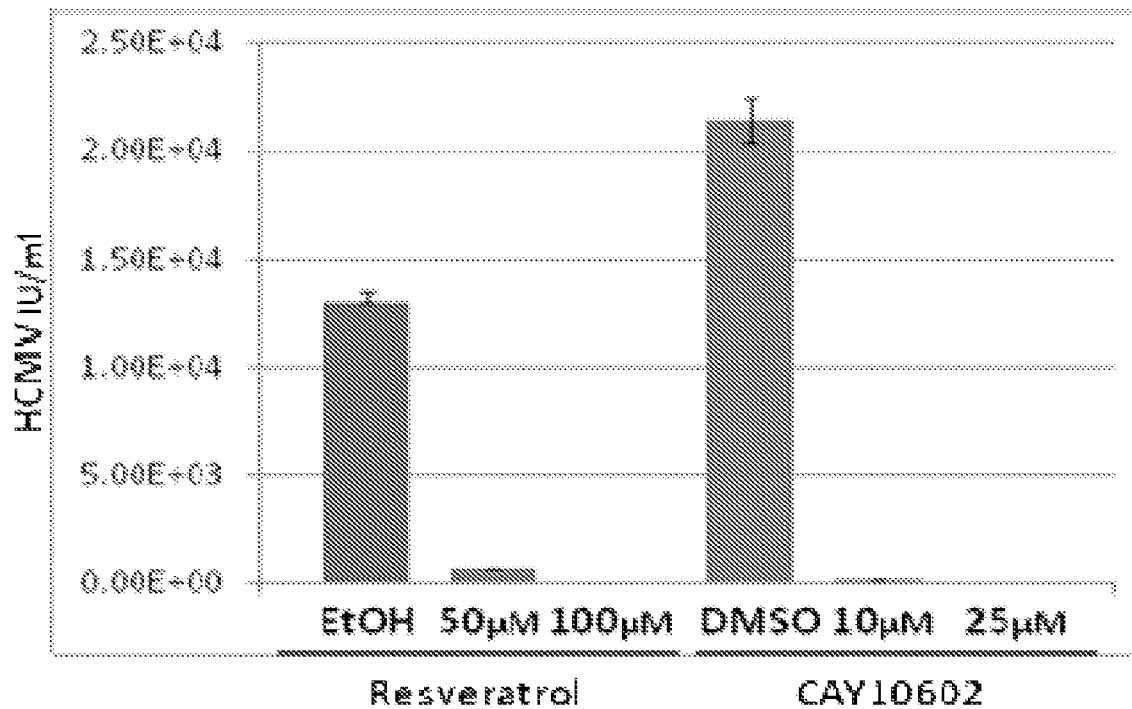
FIG. 3 illustrates that sirtuin agonists inhibit the production of infectious HCMV progeny.

Referring to FIG. 3, MRC5 fibroblasts were infected with an HCMV variant expressing GFP tagged pUL99 (the product of late viral UL99 gene) at a multiplicity of 0.25 IU/cell. Four hours after infection cells were treated with the indicated concentrations of resveratrol, CAY10602 or the carrier in which the drugs were dissolved (ethanol or DMSO). Virus yield at 96 h after infection was determined by infecting fibroblasts and assaying IE1 expression by immunofluorescence 24 h later. Treatment with 100 μM resveratrol or 25 μM CAY10602 reduced the virus yield to below the limit of detection (<$10^2$ IU/ml).

Figure 4:
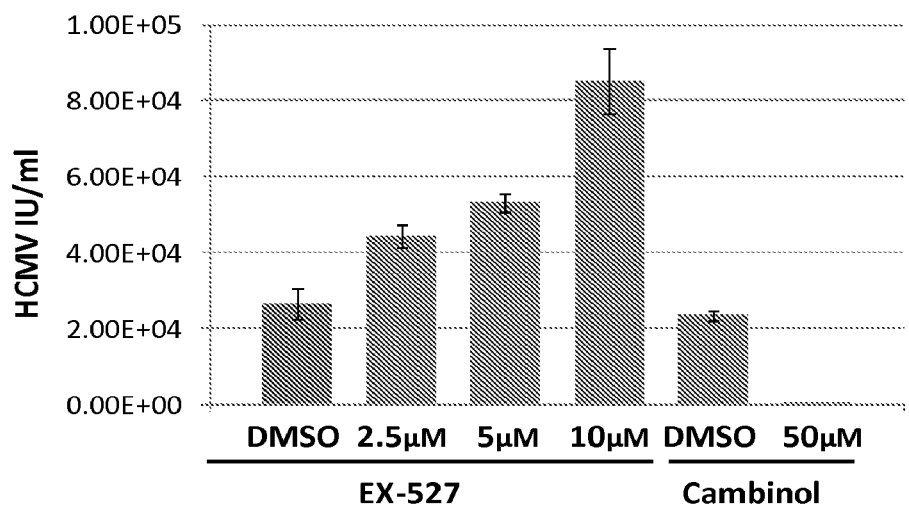
FIG. 4 illustrates that a SIRT1 antagonist elevates the production of infectious virus, whereas an antagonist of both SIRT1 and SIRT2 inhibits the production of infectious HCMV progeny.

Referring to FIG. 4, MRC5 fibroblasts were infected with an HCMV variant expressing GFP tagged pUL99 (the product of late viral UL99 gene) at a multiplicity of 0.25 IU/cell. Two hours after infection cells were treated with the indicated concentrations of SIRT1 inhibitor, EX-527; the dual SIRT1 and 2 inhibitor, Cambinol, or the carrier in which the drugs were dissolved (DMSO). Virus yield at 96 h after infection was determined by infecting fibroblasts and assaying IE1 expression by immunofluorescence 24 h later. Treatment with 50 μM cambinol reduced the virus yield to below the limit of detection (<$10^2$ IU/ml).

These results demonstrate that all members of the sirtuin family inhibit HCMV replication, and they strongly predict that drugs that increase the activity of sirtuins (sirtuin agonists) will have anti-HCMV activity. The most prominent effects on HCMV replication were observed when the mitochondrial sirtuins, SIRT3, SIRT4, and SIRT5, were inhibited by siRNAs (FIG. 1). These enzymes modulate key factors responsible for central carbon metabolism. For instance, glutamate dehydrogenase, which directs glutamine flux to the tricarboxylic acid (TCA) cycle by converting it to α-ketoglutarate, is targeted by SIRT3 and 4. Of note, glutamine is the major carbon source feeding the TCA cycle in HCMV infected cells and essential for HCMV replication. These results indicate that activators of mitochondrial sirtuins are preferential targets for antiviral therapy.

Activation of one or more sirtuins is an embodiment. Activation of one or more mitochondrial sirtuins is an embodiment. A compound that increases sirtuin activity is referred to as a sirtuin agonist herein. The compound can be a small molecule, nucleic acid, protein, or peptide. Specific sirtuin agonists contemplated include stilbene, flavone, isoflavone, flavanone, catechin, free radical protective compound, isonicotinamide, dipyridamole, ZM 336372 (3-(dimethylamino)-N-[3-[(4-hydroxybenzoyl)-amino]-4-methylphenyl]benzamide), camptothecin, coumestrol, nordihydroguaiaretic acid, esculetin, SRT-1720 (Sirtris), SRT-1460 (Sirtris), SRT-2183 (Sirtris), analogs thereof, or combinations thereof.

In some embodiments, the sirtuin agonist is a stilbene. In some embodiments, the stilbene is trans-stilbene, cis-stilbene, resveratrol, piceatannol, rhapontin, deoxyrhapontin, butein, or combinations thereof.

In some embodiments, the agonist is a chalcone. In some embodiments, the chalcone is chalcon; isoliquirtigen; butein; 4,2',4'-trihydroxychalcone; 3,4,2',4',6'-pentahydroxychalcone; or combinations thereof.

In some embodiments, the agonist is a flavone. In some embodiments, the flavone is flavone, morin, fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; or combinations thereof.

In some embodiments, the agonist is an isoflavone. In some embodiments, the isoflavone is daidzein, genistein, or combinations thereof.

In some embodiments, the agonist is a flavanone. In some embodiments, the flavanone is naringenin; flavanone; 3,5,7,3',4'-pentahydroxyflavanone; or combinations thereof.

In some embodiments, the agonist is an anthocyanidin. In some embodiments, the anthocyanidin is pelargonidin chloride, cyanidin chloride, delphinidin chloride, or combinations thereof.

In some embodiments, the agonist is a catechin. In some embodiments, the catechin is (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); or combinations thereof.

In some embodiments, the agonist is a free radical protective compound. In some embodiments, the free radical protective compound is Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanam-inium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)m-ethyl)-3,4-dihydro-2,5,7,8-tetramethyl-2H-1-benzopyran-6-ol 2HCl); or combinations thereof.

In some embodiments, the agonist is isonicotinamide or an analog of isonicotinamide. In some embodiments, the analog of isonicotinamide is .beta.-1'-5-methyl-nicotinamide-2'-deoxyribose; .beta.-D-1'-5-methyl-nico-tinamide-2'-deoxyribofuranoside; .beta.-1'-4,5-dimethyl-nicotinamide-2'-de-oxyribose; or .beta.-D-1'-4,5-dimethyl-nicotinamide-2'-deoxyribofuranoside. For additional analogs of isonicotinamide see U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/0096830; 2004/0053944; 2004/0110772; and 2004/0181063, which are hereby incorporated by reference for that disclosure.

Further examples of sirtuin agonists include trans-stilbene, cis-stilbene, resveratrol, piceatannol, rhapontin, deoxyrhapontin, butein, chalcon; isoliquirtigen; butein; trihydroxychalcone; 3,4,2',4',6'-pentahydroxychalcone; flavone, morin, fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein, genistein, naringenin; flavanone; 3,5,7,3',4'-pentahydroxyflavanone; pelargonidin chloride, cyanidin chloride, delphinidin chloride, (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanam-inium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)m-ethyl)-3,4-dihydro-2,5,7,8-tetramethyl-2H-1-benzopyran-6-ol.2HCl); .beta.-1'-5-methyl-nicotinamide-2'-deoxyribose; .beta.-D-1'-5-methyl-nico-tinamide-2'-deoxyribofuranoside; .beta.-1'-4,5-dimethyl-nicotinamide-2'-de-oxyribose; or .beta.-D-1'-4,5-dimethyl-nicotinamide-2'-deoxyribofuranoside; dipyridamole, ZM 336372 (3-(dimethylamino)-N-[3-[(4-hydroxybenzoyl)-amino]-4-methylphenyl]benzamide), camptothecin, coumestrol, nordihydroguaiaretic acid, esculetin, SRT-1720 (Sirtris), SRT-1460 (Sirtris), SRT-2183 (Sirtris), analogs thereof, or combinations thereof.

To further investigate the importance of sirtuins as anti-HCMV targets, the effect of known sirtuin activating compounds on HCMV replication was assayed. A variety of such small molecule SIRT1 activating compounds (STACs) have been described in the literature (for a review see Camins et al., 2010, Biochimica et Biophysica Acta 1799, 740-9, which is incorporated herein by reference as if fully set forth, (Table 1, below). In addition to the compounds listed in Table 1, dihydropyridine and imidazol¬[1,2-b]thiazole derivatives have been recently identified as novel SIRT1 agonists (Mia et al., 2009, J. Med Chem., 52, 5496-504, which is incorporated herein by reference as if fully set forth). SRT1720 has a structure

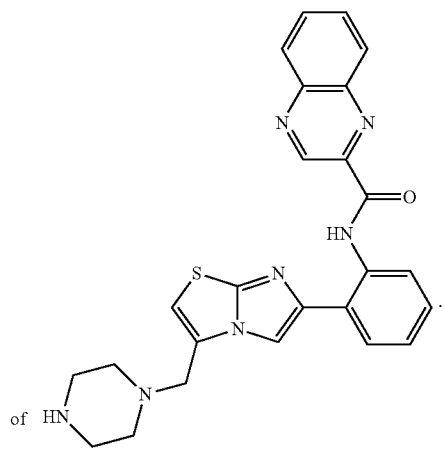 [SMILES: O=C(Nc1ccccc1-c1cn2c(CN3CCNCC3)csc2n1)c1cnc2ccccc2n1]

of

SRT1460 has a structure of

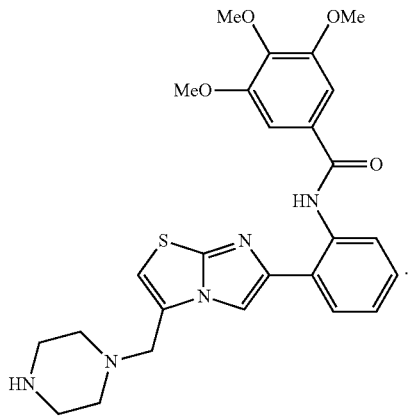 [SMILES: COc1cc(C(=O)Nc2ccccc2-c2cn3c(CN4CCNCC4)csc3n2)cc(OC)c1OC]

TABLE 1

| Compounds that increase the activity of sirtuins | | | |
|---|---|---|---|
| Compounds of natural origin | $EC_{1.5}$ | Synthetic compounds | $EC_{1.5}$ |
| Resveratrol | 46 μM | Pyrroloquinoxaline | 10 μM* |
| Quercetin | | Oxazolopyridine | 0.09 μM |
| Butein | | SRT1720 | 0.16 μM |
| Piceatannol | | SRT1460 | 2.9 μM |
| Isoliquiritigenin | | SRT2379 | 0.36 μM |

TABLE 1-continued

Compounds that increase the activity of sirtuins

| Compounds of natural origin | $EC_{1.5}$ | Synthetic compounds | $EC_{1.5}$ |
|---|---|---|---|
| Fisetin | | SRT2104 | |
| | | GSK184072 | |

$EC_{1.5}$: The concentration to activate 1.5-fold
*233% activation at this concentration Resveratrol, which is a polyphenol naturally found in some plants, is perhaps the best studied SIRT1 agonist. It increases SIRT1 activity by 1.5 fold at 46 μM and by 13 fold at 100 μM concentration (Howitz et al., 2003, Nature 425, 191-6). Resveratrol is selective for SIRT1 since it does not activate SIRT2 at 100 μM. To evaluate its effect on HCMV replication the compound was added to the culture medium of HCMV infected MRC5 cells containing 10% fetal calf serum at 4 hours after infection. Resveratrol inhibited cytopathic effect of HCMV and expression of late viral pUL99 was substantially reduced in a dose dependent manner (data not shown). The compound reduced the yield of infectious HCMV by a factor of >18-fold at 50 μM and >100-fold at 100 μM (FIG. 3).

Resveratrol has been reported to inhibit HCMV replication previously (Evers et al., 2004, Antiviral Res 63, 85-95. In particular, it was concluded that Resveratrol only inhibited viral attachment and entry. In contrast, the work herein is the first to show that modulation of each of the seven sirtuins, including SIRT1 (a principal target of resveratrol), can influence viral replication and therefore predict that induction any one of the different known sirtuin activities will inhibit the production of HCMV progeny.

The antiviral effect of SIRT1 activation on HCMV was further confirmed by employing a second SIRT1-activating compound, CAY10602, which has a structure:

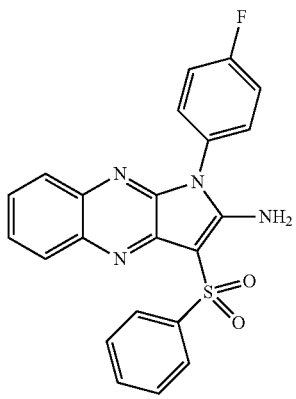 [SMILES: Nc1c(S(=O)(=O)c2ccccc2)c2nc3ccccc3nc2n1-c1ccc(F)cc1]

and is structurally distinct from resveratrol. CAY10602 was identified in a high-throughput screen as a compound that increases SIRT1-mediated deacetylation of a SIRT1-specific substrate and is a highly potent activator of SIRT1. It suppresses tumor necrosis factor alpha (TNFα) release, a process which is linked to the activity of SIRT1, to a 10-fold greater extent than resveratrol. In line with this, CAY10602 showed a strong anti-HCMV effect. At 25 μM, CAY10602 almost completely inhibited pUL99 expression and reduced the yield of infectious HCMV below the detection limit (FIG. 3). These results demonstrate that compounds activating SIRT1 block the production of infectious HCMV, and, therefore, have utility as antiviral drugs in the treatment of HCMV infections.

Next, to further confirm the anti-viral effect of sirtuins observed in siRNA experiments, small molecule inhibitors which block the activity of one or multiple sirtuins, were evaluated for effects on HCMV replication. As used herein, the term "sirtuin antagonist" or "sirtuin inhibitor" refers to a compound that decreases sirtuin activity. The compound can be a small molecule, nucleic acid, protein, or peptide. In some embodiments, the sirtuin antagonist is a dual antagonist, referring to its ability to decrease activity of two sirtuins. More specifically, disclosed herein are SIRT1/SIRT2 dual inhibitors, including, but not limited to cambinol, tenovin 6, tenovin 1, salermide, sirtinol, and combinations thereof. Further disclosed herein are combinations of a SIRT1 inhibitor and a SIRT2 inhibitor.

Several sirtuin inhibitors have been reported in literature. Among these, EX-527, is a highly selective to SIRT1 (Solomon et al., 2006, Mol Cell Biol 26, 28-38) having a structure

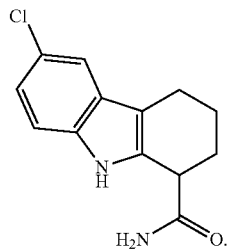 [SMILES: NC(=O)C1CCCc2c1[nH]c1ccc(Cl)cc21]

Another SIRT1 inhibitor is (S)-35 which has a structure

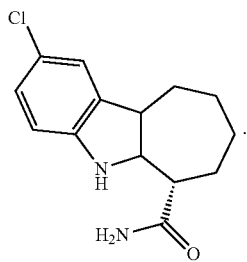 [SMILES: NC(=O)[C@H]1CCCCC2c3cc(Cl)ccc3NC21]

Cambinol inhibits NAD dependent deacetylase activity of both SIRT1 and SIRT2 (Heltweg et al., 2006, Cancer Res 66, 4368-77). Supporting the phenotype of the siRNA-mediated SIRT1 knockdown, 10 μM EX-527 increased the accumulation of late viral pUL99 protein (data not shown) and production of infectious HCMV progeny by a factor of ~4 fold in MRC5 fibroblasts (FIG. 4).

The dual SIRT1/SIRT2 inhibitor Cambinol, having a structure of

Figure 5:
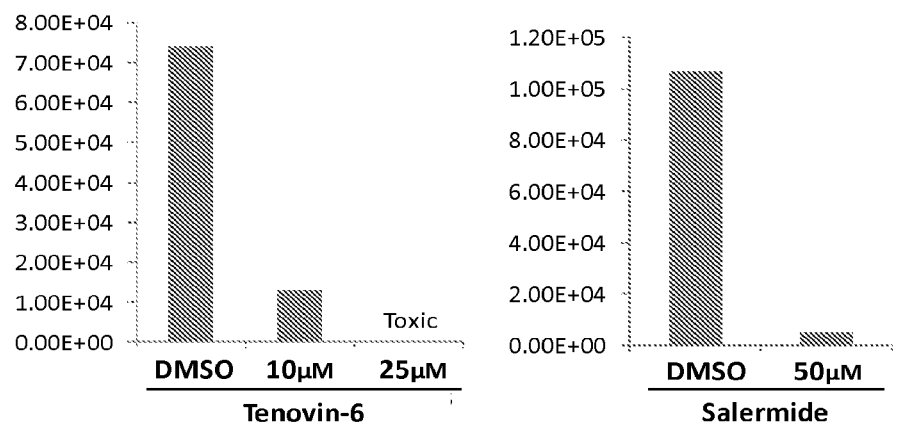
FIG. 5 illustrates that SIRT1/SIRT2 dual inhibitors tenovin-6 (left panel) and salermide (right panel) inhibit production of HCMV.

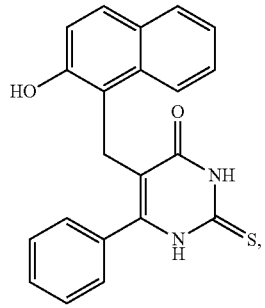 [SMILES: O=c1[nH]c(=S)[nH]c(-c2ccccc2)c1Cc1c(O)ccc2ccccc12]

showed a substantial block of pUL99 accumulation (data not shown) at 50 μM and the yield of infectious HCMV was below detection limit (<$10^2$ IU/ml) at this concentration of drug (FIG. 4). Cambinol is well-tolerated in mice and inhibits Burkitt lymphoma xenografts. The dual SIRT1/SIRT2 inhibitors Tenovin-6 and Salermide also blocked the production of infectious HCMV (FIG. 5). By blocking SIRT1 and 2, cambinol, tenovin-6 and salermide induce hyperacetylation of the p53 tumor suppressor protein, which is required for its activation during stress. p53 plays a major role in cell-cycle control, it contributes to virus-induced apoptosis, and it is a direct activator of type I interferons that induce antiviral defense. Several viruses require inactivation of p53 for efficient replication. Therefore these results demonstrate that multiple SIRT1/SIRT2 inhibitors have antiviral activity, and strongly predict that dual SIRT1 and SIRT2 inhibitors constitute a class of novel antiviral agents that inhibit HCMV as well as other viruses that require inactivation of p53. A list of non-limiting exemplary inhibitors is presented in Table 2. Tenovin 1 has a structure of

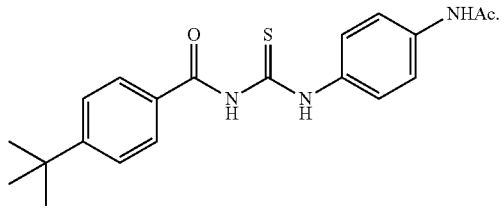 [SMILES: CC(=O)Nc1ccc(NC(=S)NC(=O)c2ccc(C(C)(C)C)cc2)cc1]

Tenovin 6 has a structure of

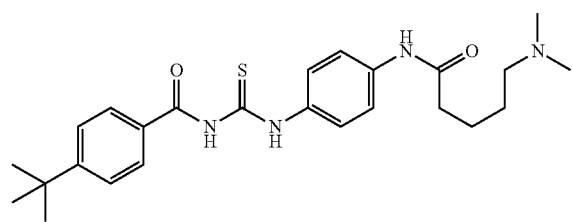

Salermide has a structure of

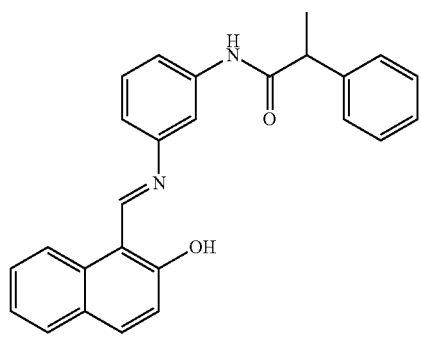

Sirtinol has a structure of

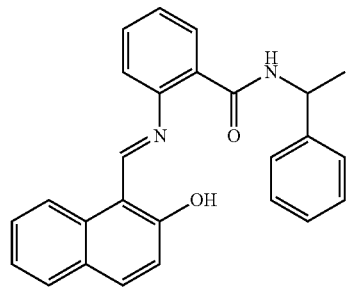 [SMILES: CC(NC(=O)c1ccccc1/N=C/c1c(O)ccc2ccccc12)c1ccccc1]

TABLE 2

| Compound | Target | $IC_{50}$ |
|---|---|---|
| Tenovin 1 | SIRT 1 and 2 | 21, 10, and 67 µM respectively |
| Tenovin 6 | SIRT1, 2 and 3 | 21, 10, and 67 µM, respectively |
| Salermide | SIRT1 and 2 | 76.2 and 45 µM respectively |
| Sirtinol | SIRT1 and 2 | 131 and 57.7 respectively |
| Cambinol | SIRT1 and 2 | 56 and 59 µM respectively |

Figure 6:
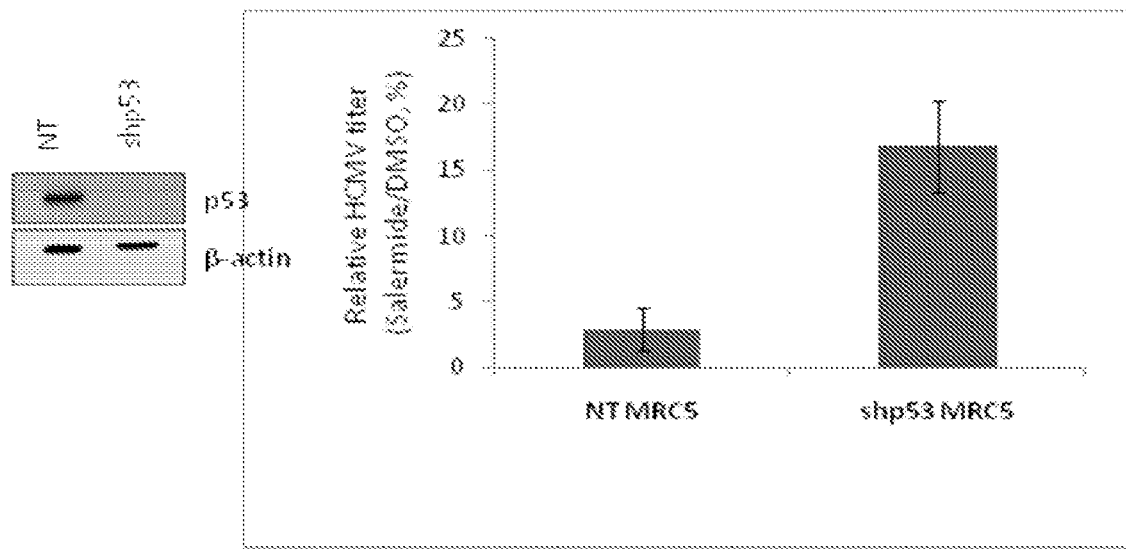
FIG. 6 illustrates that inhibition of HCMV replication by a dual SIRT1/SIRT2 inhibitor (Salermide) requires p53. Right panel: MRC5 cells stably expressing either p53 shRNA (shp53 MRC5) or non-targeting shRNA (NT MRC5) were infected with AD169 HCMV strain at a multiplicity of 0.5 IU/cell. At 2hpi, cells were treated either with 50 µM Salermide in DMSO or DMSO alone. This treatment was repeated at 48hpi. At 96hpi, virus-containing supernatants were collected and HCMV titers determined using infectious center assay in MRC5 cells. The result is representative of biological duplicates. Left panel: The knockdown of p53 in shp53 cell line was verified by Western Blot.

Dual SIRT1/SIRT2 inhibitors are thought to act in part by blocking the ability of sirtuins to inhibit and consequently activating the tumor suppressor protein p53 (see Heltweg et al., 2006 and references therein). Therefore the possibility that p53 activity is needed for dual SIRT1/SIRT2 inhibitors to inhibit the production of HCMV progeny was tested (FIG. 6). Results showed that salermide inhibited the production of HCMV progeny by a factor of nearly 80 in cells expressing p53. In contrast, the drug inhibited HCMV production by a factor of only about 5 in cells in which p53 levels were substantially reduced by knockdown with a p53-specific shRNA. This observation reveals that dual SIRT1/SIRT2 inhibitors inhibit HCMV production at least in part through a p53-dependent mechanism. Many viruses are known to block the activity of p53 as part of their strategy for successful replication. The block can be achieved by degradation of a substantial portion of the cellular p53, by interaction with a viral protein that inhibits p53 activity or by posttranslational modification of p53, including changes in acetylation status. Dual SIRT1/SIRT2 inhibitors can relieve the block either by hyper-activation of residual active p53 or re-activation of inactivated p53. Therefore, the demonstration of a role for p53 predicts that any virus that inactivates p53 will be sensitive to dual SIRT1/SIRT2 inhibitors. Contemplated viruses that inactivate p53 include, but are not limited to, Adenoviridae (Adenovirus, with E1B-55K as a p53 inactivating protein); Hepadnaviridae (HBV, with X protein a p53 inactivating protein); Herpesviridae (EBV, with LMP1 a p53 inactivating protein; HSV-1 with ICP0 as a p53 inactivating protein; HCMV, with 1E1 as a p53 inactivating protein; KSHV with LANA as a p53 inactivating protein); Flaviviridae (HCV with NS5A as a p53 inactivating protein); Orthomixoviridae (Influenza A with NS1 as a p53 inactivating protein); Papillomaviridae (HPV with E6 as a p53 inactivating protein); Polyomaviridae (SV40 with Large T-antigen as a p53 inactivating protein; JC virus with Large T-antigen as a p53 inactivating protein; BK virus with Large T antigen as a p53 inactivating protein); and Retroviridae (HIV with Tat as a p53 inactivating protein).

In addition to dual SIRT1/SIRT 2 inhibitors (or inhibitors of two or more sirtuins), further contemplated are combination administration of two sirtuin inhibitors, e.g., a SIRT1 inhibitor and a SIRT2 inhibitor or a SIRT1 inhibitor and SIRT3 inhibitor, or a SIRT2 inhibitor and a SIRT3 inhibitor, or other combinations of sirtuin inhibitors as disclosed above, to achieve dual inhibition of the sirtuins.

SIRT1 inhibitors include EX-527 and (S)-35 as noted above, and HR73, having a structure
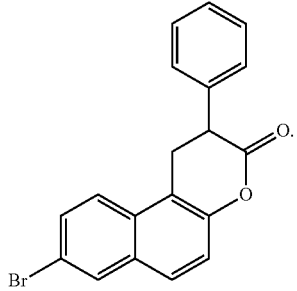 [SMILES: O=C1Oc2ccc3cc(Br)ccc3c2CC1c1ccccc1]
SIRT2 inhibitors include Ro31-8220 having a structure
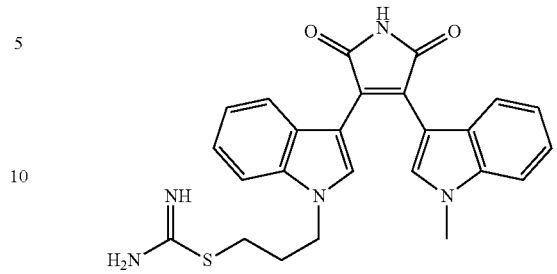
Other sirtuin inhibitors contemplated include the following but specifically exclude suramin (see, e.g., Trapp, et al., *Chem. Med. Chem.*, 2:1419-1431 (2007)):
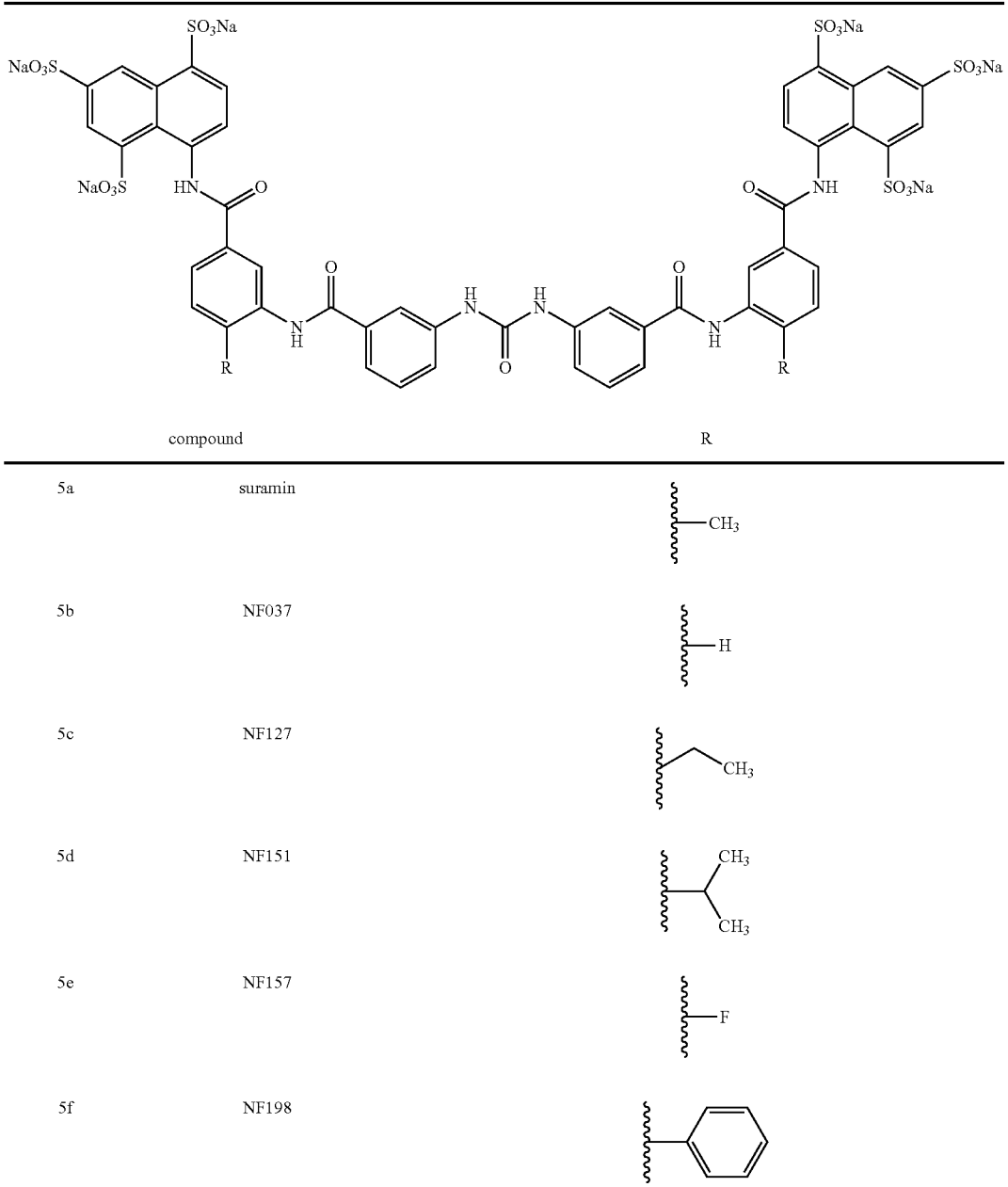
| compound | | R |
|---|---|---|
| 5a | suramin | —CH₃ |
| 5b | NF037 | —H |
| 5c | NF127 | —CH₂CH₃ |
| 5d | NF151 | —CH(CH₃)₂ |
| 5e | NF157 | —F |
| 5f | NF198 | —C₆H₅ |

-continued
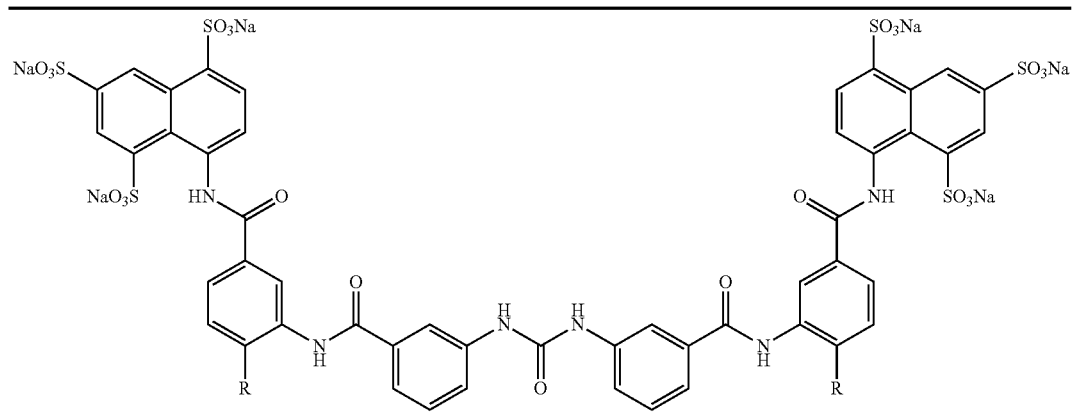
| compound | | R |
|---|---|---|
| 5g | NF222 | 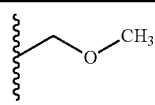 |
| 5h | NF258 | 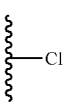 |
| 5i | NF260 | 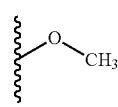 |
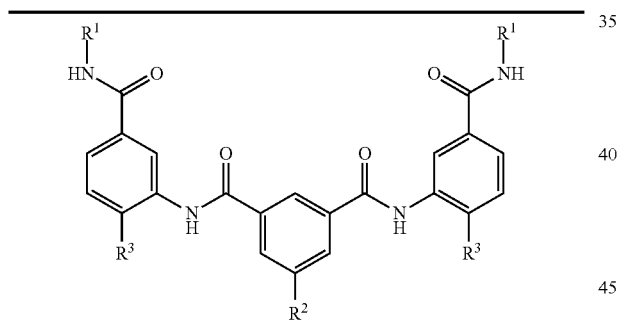
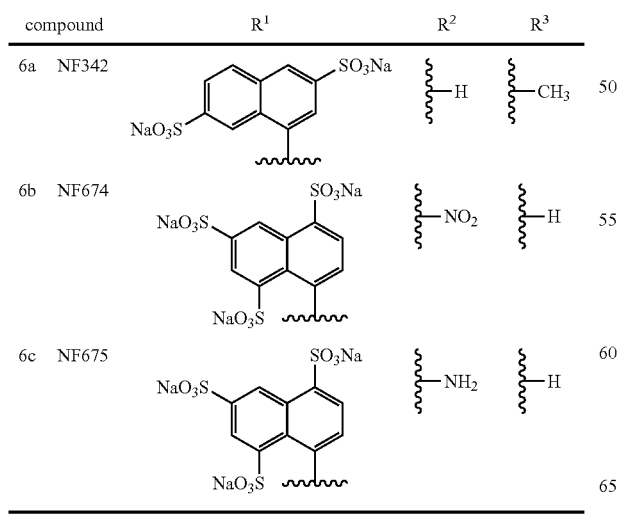

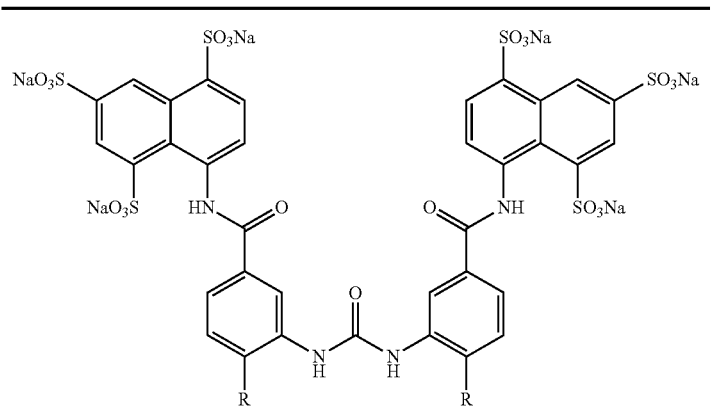
| compound | | R |
|---|---|---|
| 7a | NF023 | —H |
| 7b | NF150 | —CH(CH₃)₂ |
| 7c | NF156 | —F |
| 7d | NF259 | —OCH₃ |
| 7e | NF058 | —CH₃ |
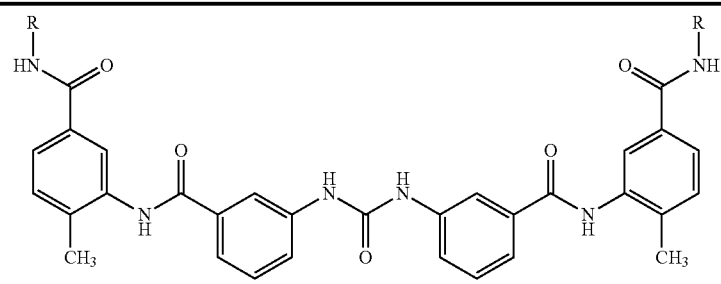
| compound | | R |
|---|---|---|
| 8a | NF763 | 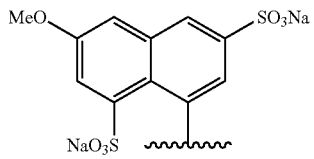 |

| | | |
|---|---|---|
| 8b | NF770 | 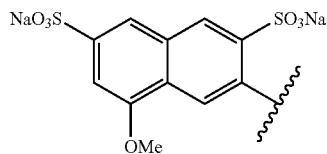 |
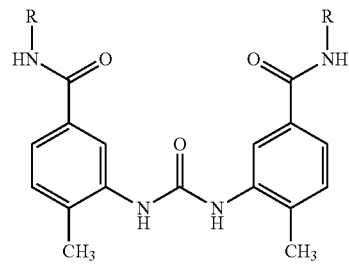
| compound | | R |
|---|---|---|
| 9a | NF290 | 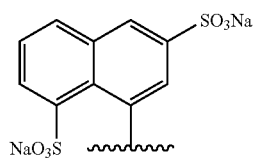 |
| 9a | NF762 | 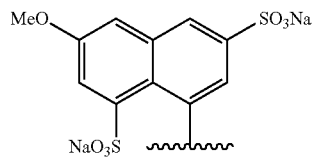 |
| 9a | NF769 | 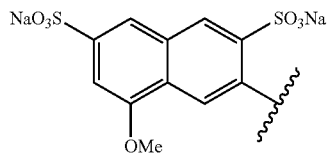 |
| compound | | |
|---|---|---|
| 10 | NF136 | 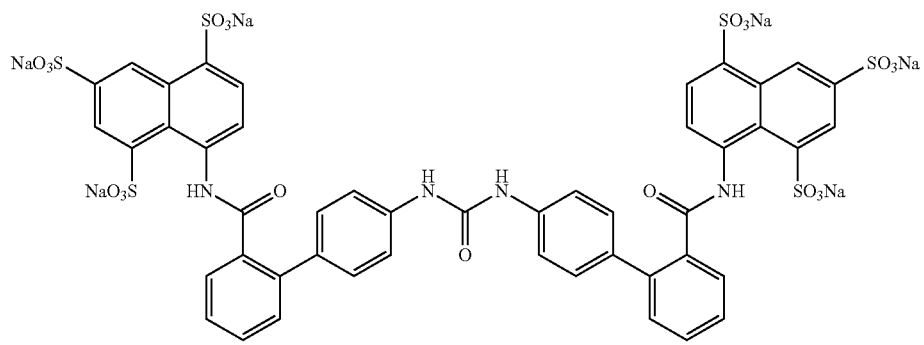 |

| 11 | NF444 | 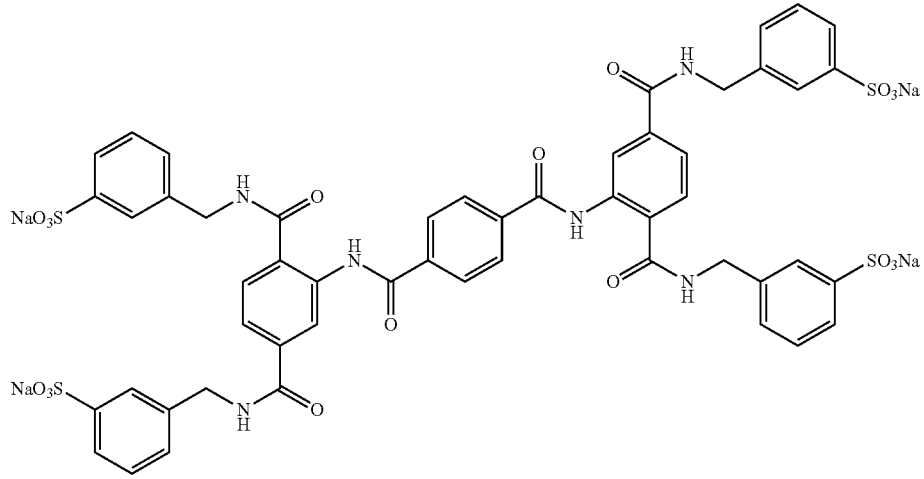 |
| 12 | NF343 | 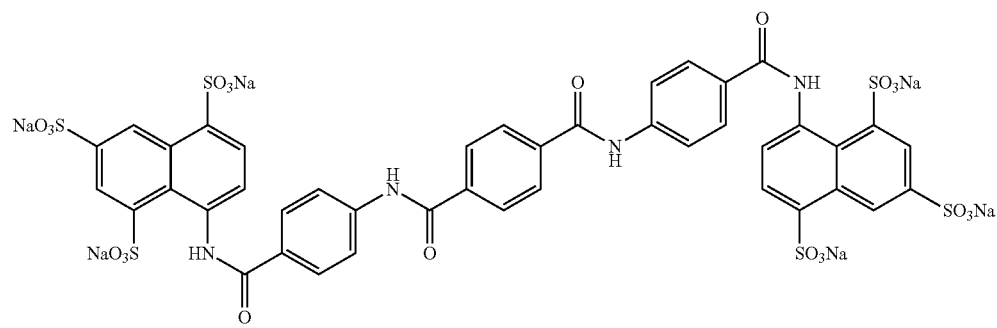 |
| 13a | NF443 n = 1 | 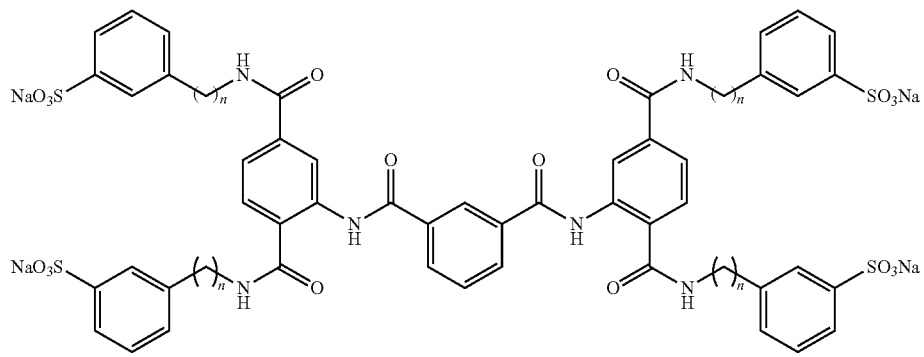 |
| 13b | NF451 n = 0 | |
| 14a | NF154 | 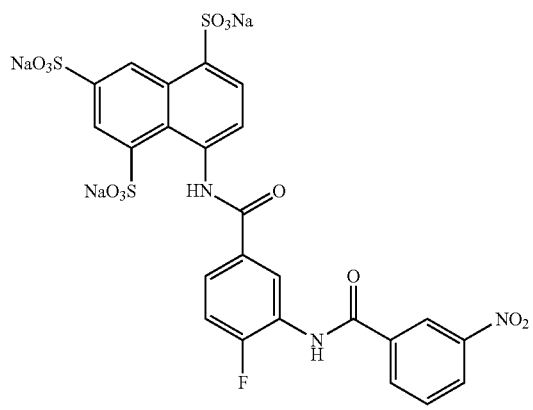 |

| | | | | | | | |
|---|---|---|---|---|---|---|---|
| 14b | NF155 | 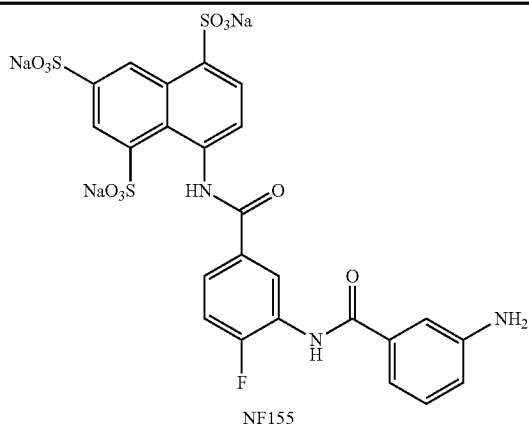 NF155 | | | | | |
| 15 | NF669 | 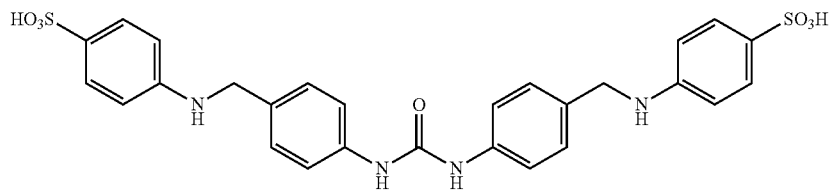 | | | | | |
| 16 | AMI 1 | 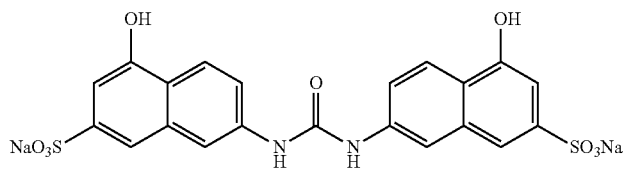 | | | | | |

Further contemplated sirtuin inhibitors include the following (see, e.g., Medda, et al., *J. Med. Chem.*, 52:2673-2682 (2009)):

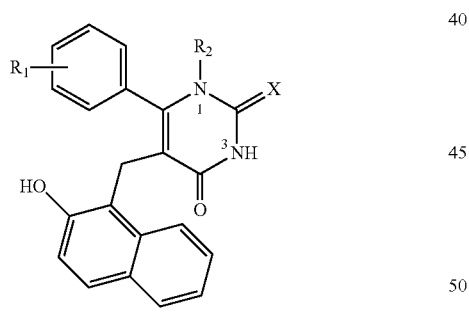

1 $R_1$=$R_2$=H, X=S, Cambinol
6a $R_1$=$R_2$=H, X=O
6b $R_1$=p-Br, $R_2$=H, X=S
6c $R_1$=p-OMe, $R_2$=H, X=S
6e $R_1$=H, $R_2$=Me; X=S
6i-xi $R_2$=H, X=S
6f,g,h,j $R_1$=H, X=S, $R_2$ varies

TABLE 1

Inhibition (at 60 μM ± SE$^a$ (%)) of Sirtuins by the Novel Analogs 6i-xi and 6a-6j

| compd | $R_1$ | $R_2$ | X | SIRT1 | IC$_{50}$$^b$ | SIRT2 | IC$_{50}$$^b$ |
|---|---|---|---|---|---|---|---|
| 1 | H | H | S | 59.5 ± 1 | 40.7 ± 11 | 51.9 ± 1 | 47.9 ± 12 |
| 6a | H | H | O | 15.5 ± 2 | | 6.5 ± 4 | |

TABLE 1-continued

Inhibition (at 60 μM ± SE$^a$ (%)) of Sirtuins by the Novel Analogs 6i-xi and 6a-6j

| compd | R$_1$ | R$_2$ | X | SIRT1 | IC$_{50}$$^b$ | SIRT2 | IC$_{50}$$^b$ |
|---|---|---|---|---|---|---|---|
| 6b | p-Br | H | S | 82.3 ± 1 | 12.7 ± 2 | 9.4 ± 1 | >90 |
| 6c | p-CH$_3$O | H | S | 6.4 ± 1 | | 9.2 ± 2 | |
| 6d | H | H | S | 37.8 ± 1 | | 52.7 ± 2 | |
| 6i | o-CH$_3$ | H | S | 79.6 ± 1 | 43.0 ± 2 | 29.1 ± 2 | |
| 6ii | m-CH$_3$ | H | S | 83.2 ± 4 | 44.2 ± 2 | 12.7 ± 2 | |
| 6iii | p-CH$_3$ | H | S | 79.0 ± 2 | 44.5 ± 1 | 13.4 ± 3 | |
| 6iv | p-Cl | H | S | 13.7 ± 1 | | 20.1 ± 1 | |
| 6v | p-I | H | S | 7.7 ± 1 | | 7.7 ± 1 | |
| 6vi | p-CF$_3$ | H | S | 15.1 ± 1 | | 6.7 ± 1 | |
| 6vii | o-Br | H | S | 19.7 ± 1 | | | |
| 6viii | m-Br | H | S | 4.8 ± 1 | | 6.6 ± 3 | |
| 6ix | m-Cl | H | S | 11.3 ± 1 | | 7.6 ± 6 | |
| 6x | o-F | H | S | 89.0 ± 1 | 50.0 ±1 | 19.5 ± 1 | |
| 6xi | m-F | H | S | 87.8 ± 1 | 38.3 ± 1 | 52.1 ± 1 | |
| 6e | H | Me | S | 29.4 ± 1 | >90 | 80.4 ± 1 | 20.1 ± 5 |
| 6f | H | Et | S | 31.9 ± 1 | | 86.8 ± 1 | 10.5 ± 3 |
| 6g | H | allyl | S | 37.5 ± 1 | | 88.3 ± 1 | 22.2 ± 1 |
| 6h | H | n-prop | S | 25.0 ± 2 | | 94.7 ± 1 | 4.8 ± 2 |
| 6j | H | n-But | S | 16.9 ± 1 | | 97.6 ± 1 | 1.0 ± 1 |

$^a$SE, standard error (n = 2).
$^b$IC$_{50}$ values were determined for compounds that had over 60% inhibition at 60 μM for SIRT1 and SIRT2 (repeated at least twice).

Also contemplated as SIRT1 and SIRT2 inhibitors are the following (see, e.g., Napper, et al., *J. Med. Chem.*, 48:8045-8054 (2005)):

| compd | R$_1$ | R$_2$ | R$_3$ | R$_4$ | R$_5$ | IC$_{50}$ (μM)$^a$ |
|---|---|---|---|---|---|---|
| 1 | Cl | H | H | CONH$_2$ | H | 0.098 |
| 1 (e1) | Cl | H | H | CONH$_2$ | H | 0.123 |
| 1 (e2) | Cl | H | H | CONH$_2$ | H | >100 |
| 2 | CH$_3$ | H | H | CONH$_2$ | H | 0.205 |
| 3 | H | H | H | CONH$_2$ | H | 1.47 |
| 5 | Cl | H | H | CO$_2$Et | H | >100 |
| 8 | Cl | H | H | CO$_2$H | H | >100 |
| 12 | OH | H | H | CONH$_2$ | H | 15.0 |
| 15 | Cl | H | H | CONHOH | H | 77.6 |
| 26 | Cl | H | H | H | CONH$_2$ | 34.5 |
| 27 | Br | H | H | H | CONH$_2$ | 2.44 |
| 36 | Cl | H | H | CONHEt | H | >100 |
| 37 | Cl | H | H | CONHEt$_2$ | H | >100 |
| 38 | Cl | H | H | CONHCH$_2$CONH$_2$ | H | >100 |
| 39 | CH$_3$ | H | H | CH$_2$NH$_2$ | H | >100 |
| 40 | CH$_3$ | CH$_3$ | H | CONH$_2$ | H | >100 |
| 41 | CH$_3$ | H | CH$_3$ | CONH$_2$ | H | 13.0 |

$^a$Data are reported as the mean of at least three independent determinations; standard error of the mean ≤30%.

| compd | R | n | X | IC$_{50}$ (μM)$^a$ |
|---|---|---|---|---|
| 1 | Cl | 1 | CH$_2$ | 0.098 |
| 3 | H | 1 | CH$_2$ | 1.47 |
| 13 | — | — | — | >100 |
| 20 | Cl | 1 | NH | 18.0 |
| 21 | Br | 1 | NH | >100 |
| 23 | Cl | 1 | NHCOCH$_3$ | 79.9 |
| 30 | Cl | 0 | CH$_2$ | 0.409 |
| 31 | H | 0 | CH$_2$ | 2.67 |
| 35 | Cl | 2 | CH$_2$ | 0.124 |
| (S)-35 | Cl | 2 | CH$_2$ | 0.063 |
| (R)-35 | Cl | 2 | CH$_2$ | 23.0 |

$^a$Data are reported as the mean of at least three independent determinations; standard error of the mean ≤30%.

Further contemplated are sirtuin inhibitors having the following structures (see e.g. Bodner, et al., *PNAS*, 103(11): 4246-4251 (2006) and Outeiro et al., *Science*, 317:516-519 (2007)):

C
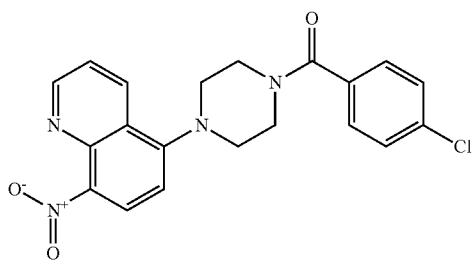
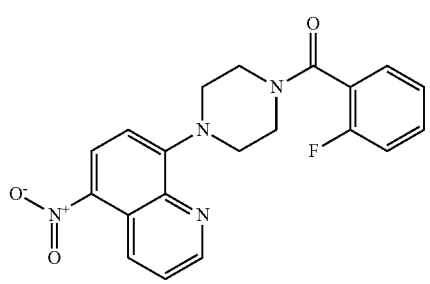
B22
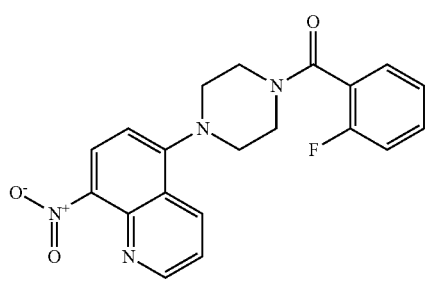
B21
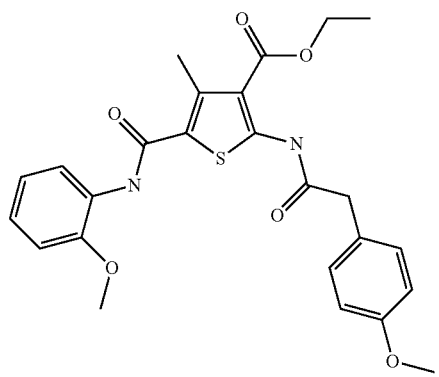
B5
B2
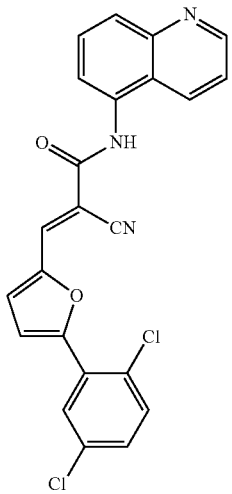
AGK2
Also contemplated are sirtuin inhibitors having the following structures (see, e.g., Kiviranta, et al., *J Med. Chem.*, 49(26):7907 (2006)):
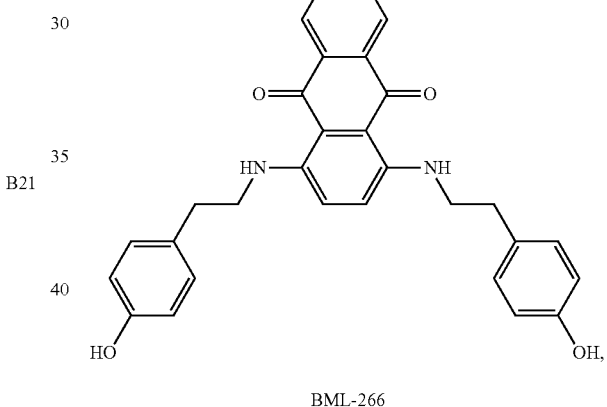
BML-266
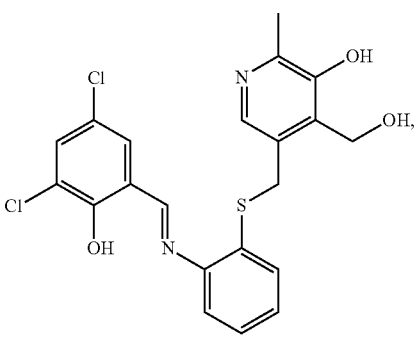
2
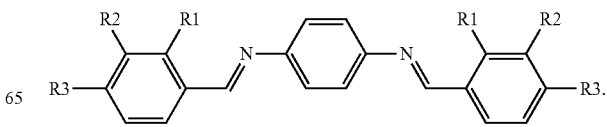

-continued

| compd | R1 | R2 | R3 | inhibition at 200 μM ± SD,[a]% |
|---|---|---|---|---|
| 3a | H | H | H | 35 ± 1.4 |
| 3b | OH | H | H | 56 ± 8.2 |
| 3c | H | OH | H | 12 ± 0.9 |
| 3d | H | H | OH | 22 ± 1.6 |
| 3e | H | OH | OH | 13 ± 0.2 |
| 3f | OCH₃ | H | H | 13 ± 0.5 |
| 3g | H | OCH₃ | H | 20 ± 1.2 |
| 3h | H | H | OCH₃ | ND[b] |

[a]SD = standard deviation.
[b]The product did not dissolve.

(4)

| compd | R1 | R2 | R3 | inhibition at 200 μM ± SD.[a]% |
|---|---|---|---|---|
| 4a | H | H | H | 21 ± 1.7 |
| 4b | OH | H | H | 27 ± 2.4 |
| 4c | H | OH | H | 8 ± 0.4 |
| 4d | H | H | OH | 14 ± 0.5 |

[a]SD = standard deviation.

(5)

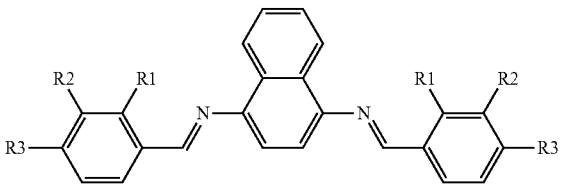

| compd | R1 | R2 | R3 | inhibition at 200 mM ± SD,[a]% |
|---|---|---|---|---|
| 5a | H | H | H | 18 ± 0.5 |
| 5b | OH | H | H | 38 ± 1.2 |
| 5c | H | OH | H | 53 ± 1.9 |
| 5d | H | H | OH | 64 ± 1.9 |
| 5e | OCH₂ | H | H | 34 ± 1.2 |
| 5f | H | OCH₃ | H | 20 ± 0.2 |
| 5g | H | H | OCH₃ | 17 ± 1.1 |

Further contemplated are sirtuin inhibitors as shown below (see, e.g., Sanders, et al., *Bioorg. Med. Chem.,* 17(19): 7031-7041 (2009)).

(7)

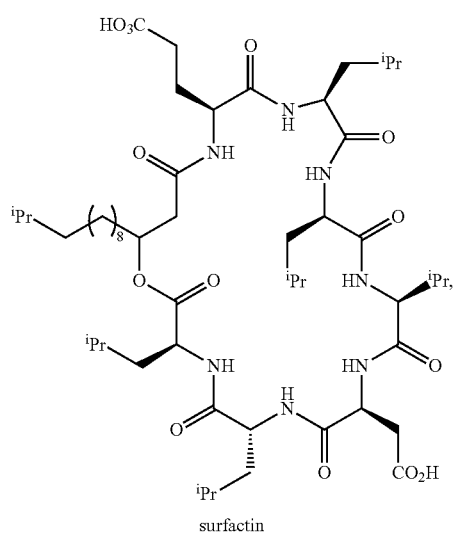

surfactin (10)

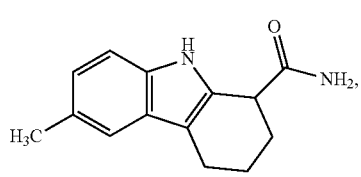 [SMILES: Cc1ccc2[nH]c3c(c2c1)CCCC3C(N)=O]

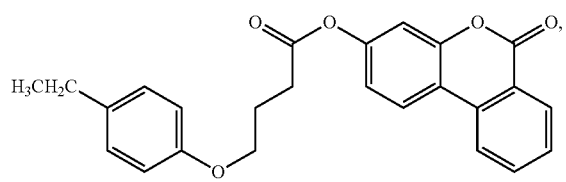
(11)
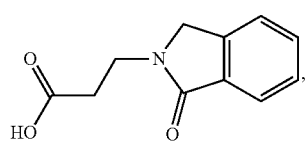 [SMILES: O=C(O)CCN1Cc2ccccc2C1=O]
(12)
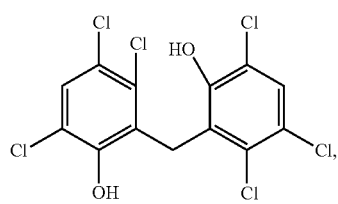 [SMILES: Oc1c(Cl)cc(Cl)c(Cl)c1Cc1c(O)c(Cl)cc(Cl)c1Cl]
(13)
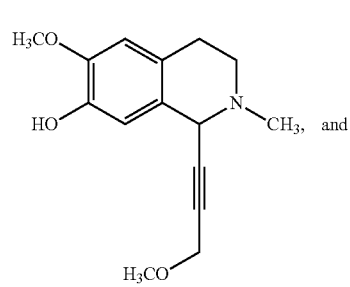 [SMILES: COCC#CC1c2cc(O)c(OC)cc2CCN1C]
(14a)
and
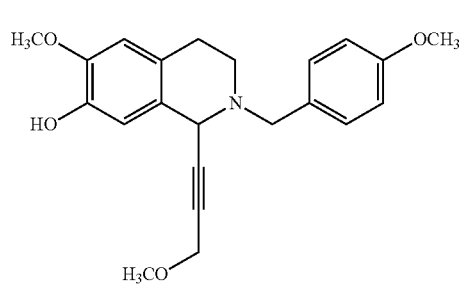 [SMILES: COCC#CC1c2cc(O)c(OC)cc2CCN1Cc1ccc(OC)cc1]
(14b)
| Compound | Hst2 IC$_{50}$ (µM) | SIRT1 IC$_{50}$ (µM) |
| --- | --- | --- |
| Nicotinamide (1) | 91 ± 7 | 250 ± 80 |
| Sirtinol (2) | 48 ± 11 | 120 ± 23 |
| Splitomycin (3) | >600 | >500 |
| Cambinol (4) | >1000 | >600 |
| Tenovin-6 (5) | >100* | ~100* |
| Ro 31-8220 (6) | 20.0 ± 0.9 | 25 ± 7 |
| Surfactin (7) | >700 | >600 |
| Suramin (8) | 240 ± 70 | 0.6 ± 0.3 |
| Indole 35 (9) | 1.3 ± 0.1 | 0.18 ± 0.02 |
| Indole 2 (10) | 14.5 ± 0.6 | 0.64 ± 0.06 |
| 11 | 6.5 ± 1.3 | 6.0 ± 0.4 |
| 12 | 19.9 ± 0.6 | 80 ± 5 |
| 13 | 12.5 ± 0.6 | 34 ± 10 |
| 14a | 130 ± 4 | 570 ± 200 |
| 14b | 260 ± 20 | nd |

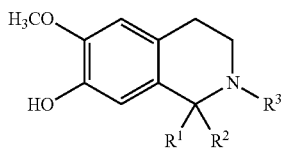

| Compound | R¹ | R² | R³ | % Activity at 50 μM | % Activity at 500 μM |
|---|---|---|---|---|---|
| 7-133 | H | H | —CH(CH₃)₂ | 100 | 98 |
| 7-52 | —CH₂—C≡CH | H | —CH(CH₃)₂ | 100 | 86 |
| 7-56 | —CH₂—C≡CH (S) | H | —CH(CH₃)₂ | 96 | 70 |
| 7-57 | —CH₂—C≡CH (R) | H | —CH(CH₃)₂ | 97 | 74 |
| 14a | —CH₂—C≡C—CH₂—OCH₃ | H | —CH₂—C₆H₄—OCH₃ | 76 | 5 |
| 14b | —CH₂—C≡C—CH₂—OCH₃ | H | —CH(CH₃)₂ | 92 | 2 |
| 7-128 | —CH₂CH₂CH₂—OCH₃ | H | —CH(CH₃)₂ | 99 | 92 |
| 7-129 | —CH₂—CH=CH—OCH₃ | H | —CH(CH₃)₂ | 97 | 94 |
| 7-123 | —CH₂—C≡C—CH₂—OCH₃ | —CH₃ | —CH(CH₃)₂ | 100 | 100 |

Data are reported as the precent of residual enzyme activity in the presence of 50 or 500 μM compound relative to the control reaction with no added inhibitor. Data are reproted as the average of three independent determinations, standard deviation of the average ≤10%.

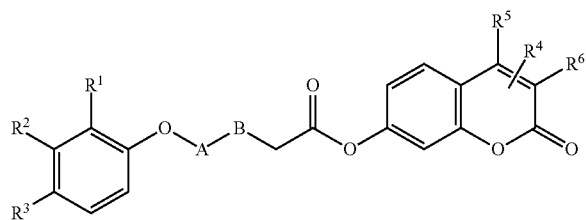

| Compound | A | B | $R^1$ | $R^2$ | $R^3$ | $R^4$ | $R^5$ | $R^6$ | % Activity at 50 μM | % Activity at 500 μM |
|---|---|---|---|---|---|---|---|---|---|---|
| 11 | $CH_2$ | $CH_2$ | H | H | H | $CH_2CH_3$ | phenyl | — | — | <1 | <1 |
| 5140108 | — | — | H | $CH_3$ | H | — | $CH_3$ | H | 90 | 13 |
| 6959933 | $CH_2$ | $CH_2$ | H | H | $OCH_3$ | — | $CH_3$ | H | 93 | 35 |
| 5237467 | — | — | H | H | H | — | $CH_3$ | H | 91 | 45 |
| 7985301 | $CH_2$ | $CH_2$ | $CH_3$ | H | $CH_3$ | cyclopentyl | — | — | 93 | 49 |
| 7988362 | $CH_2$ | $CH_2$ | $CH_2$ | H | $CH_3$ | — | $CH_3$ | H | 90 | 51 |
| 6802623 | $CH_2$ | $CH_2$ | H | H | $CH_2CH_3$ | — | $CH_3$ | H | 86 | 53 |
| 6836332 | $CH_2$ | $CH_2$ | H | H | $CH_3$ | — | $CH_3$ | H | 99 | 57 |
| 6978945 | $CH_2$ | $CH_2$ | H | H | $OCH_3$ | cyclopentyl | — | — | 95 | 58 |
| 5366302 | $CH_2$ | $CH_2$ | Cl | H | Cl | — | $CH_3$ | H | 90 | 68 |
| 53378 | CONH | $CH_2$ | H | H | H | — | $CH_3$ | Cl | 100 | 74 |

Data are reported as the precent of residual enzyme activity in the presence of 50 or 500 μM compound relative to the control reaction with no added inhibitor. Data are reproted as the average of three independent determinations, standard deviation of the average ≤10%.

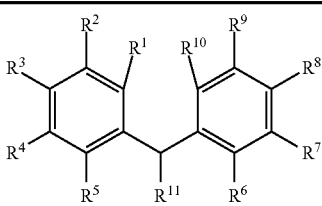

| Compound | $R^1$ | $R^2$ | $R^3$ | $R^4$ | $R^5$ | $R^6$ | $R^7$ | $R^8$ | $R^9$ | $R^{10}$ | $R^{11}$ | % Activity at 50 μM | % Activity at 500 μM |
|---|---|---|---|---|---|---|---|---|---|---|---|---|---|
| 13 | Cl | Cl | H | Cl | OH | Cl | Cl | H | Cl | OH | H | <1 | <1 |
| 97252 | H | $CH_3$ | OH | $CH_3$ | H | H | $CH_3$ | OH | $CH_3$ | H | H | 89 | 43 |
| 97211 | H | H | $CF_3$ | H | H | H | H | H | H | H | OH | 100 | 81 |
| 72030 | H | H | H | H | H | H | OH | H | H | H | H | 100 | 88 |
| 56413 | H | H | H | $NH_2$ | H | H | $NH_2$ | H | H | H | H | 100 | 100 |
| 43909 | Cl | H | H | H | H | OH | pyridyl | | H | H | $NHCOCH_3$ | 100 | 100 |

Data are reported as the precent of residual enzyme activity in the presence of 50 or 500 μM compound relative to the control reaction with no added inhibitor. Data are reproted as the average of three independent determinations, standard deviation of the average ≤10%.

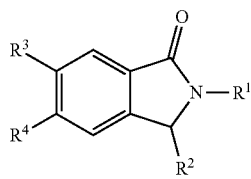
| Compound | R¹ | R² | R³ | R⁴ | IC$_{50}$ (μM) |
|---|---|---|---|---|---|
| 12 | ~~~CH₂CH₂COOH | H | H | H | 19.9 ±0.5 |
| 39008 | ~~~CH₂CH₂COOH | =O | Cl | Cl | No inhibition |
| 47054 | ~~~CH₂CH₂COOH | =O | 4H-benzo[d][1,3]oxazin-4-one-2-yl | H | No inhibition |
| 42071 | ~~~CH₂CH₂COOH | H | NH₂ | H | No inhibition |
| 47032 | ~~~CH₂CH₂COOH | =O | H | H | No inhibition |
| 04265 | ~~~CH₂CH₂C(O)CH(CH₃)₂ | =O | H | H | No inhibition |
| 91032 | ~~~CH₂CH₂Br | =O | H | H | No inhibition |
| 00032 | ~~~CH(COOH)CH₂CH₂S(O)CH₃ | =O | H | H | No inhibition |

Further contemplated are sirtuin inhibitors disclosed below (see, e.g., Schlicker, et al., *Aging*, 3(9):852 (2011)):
(3)
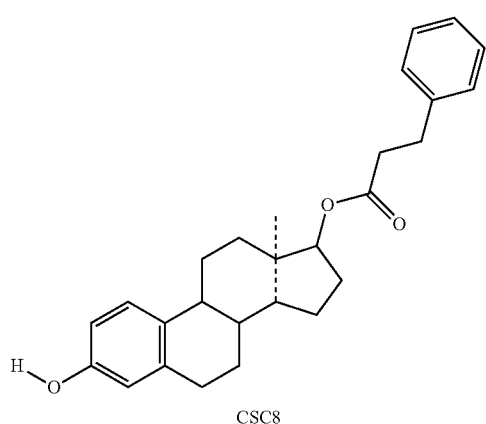
CSC8
(4)
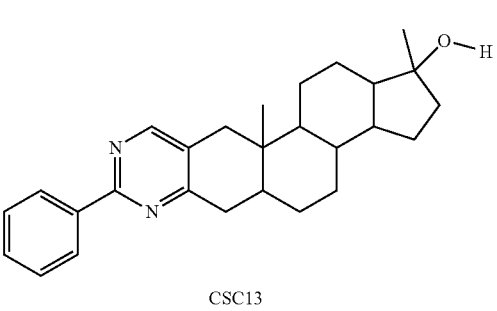
CSC13
b
(8)
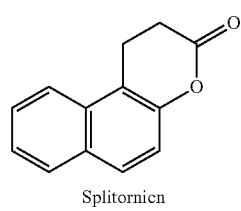
Splitornien
(9)
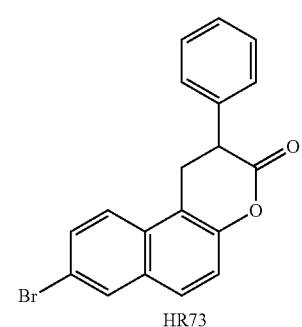
HR73
(10)
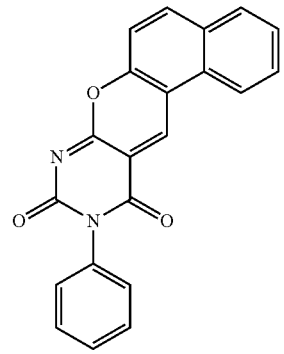
(11)
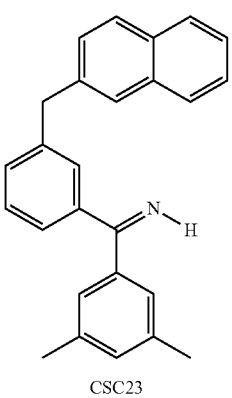
CSC23
(12)
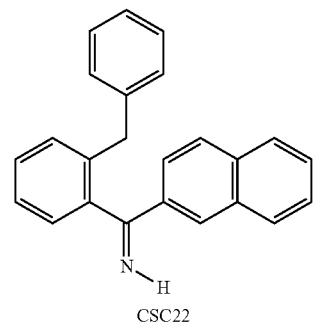
CSC22
(13)
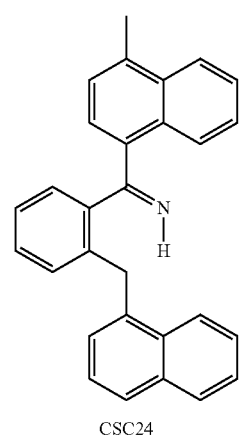
CSC24

| cmp-no. | NCS no. | Chemical structure |
|---|---|---|
| CSC1 | 11241 | |
| CSC2 | 12339 | 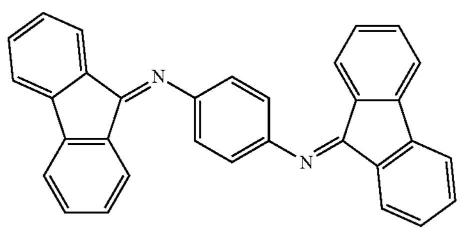 [SMILES: c1ccc2c(c1)C(=Nc1ccc(N=C3c4ccccc4-c4ccccc43)cc1)c1ccccc1-2] |
| CSC3 | 12363 | 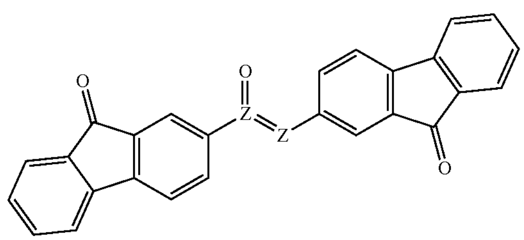 |
| CSC4 | 13726 | 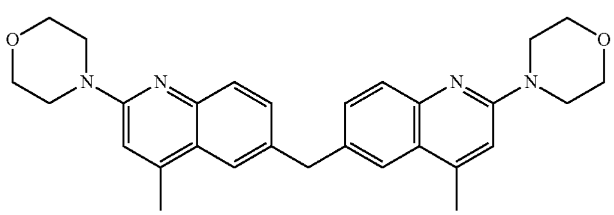 [SMILES: Cc1cc(N2CCOCC2)nc2ccc(Cc3ccc4nc(N5CCOCC5)cc(C)c4c3)cc12] |
| CSC5 | 13728 | 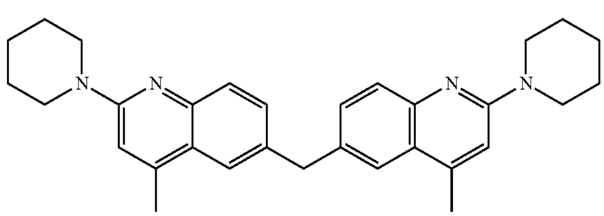 [SMILES: Cc1cc(N2CCCCC2)nc2ccc(Cc3ccc4nc(N5CCCCC5)cc(C)c4c3)cc12] |

-continued

| cmp-no. | NCS no. | Chemical structure |
|---|---|---|
| CSC6 | 23128 | 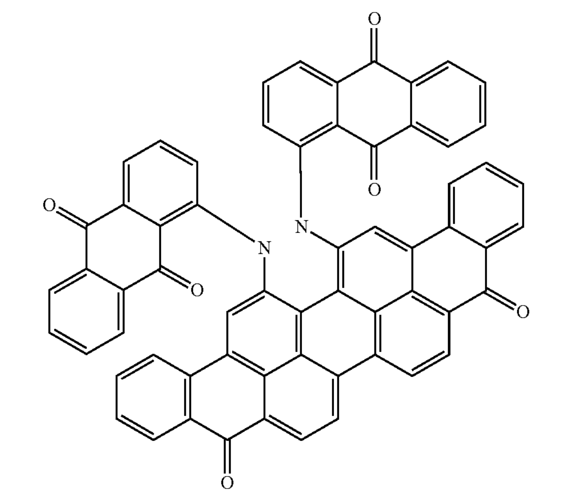 [SMILES: O=C1c2ccccc2C(=O)c2c(Nc3cc4c5c(ccc6c7ccc8c9c(cc(Nc%10cccc%11c%10C(=O)c%10ccccc%10C%11=O)c(c3c56)c97)-c3ccccc3C8=O)C(=O)c3ccccc3-4)cccc21] |
| CSC7 | 23217 | 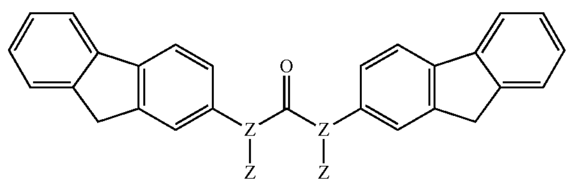 |
| CSC8 | 26645 | 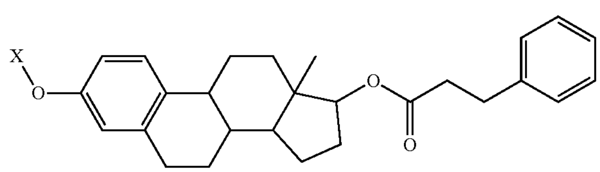 |
| CSC9 | 35049 | 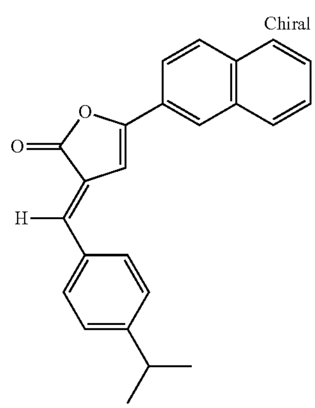 [SMILES: CC(C)c1ccc(/C=C2\C=C(c3ccc4ccccc4c3)OC2=O)cc1] |
| CSC11 | 35949 | 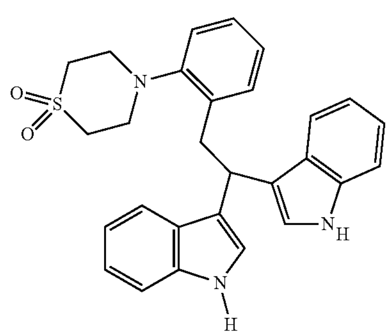 |

-continued

| cmp-no. | NCS no. | Chemical structure |
|---|---|---|
| CSC12 | 37245 | 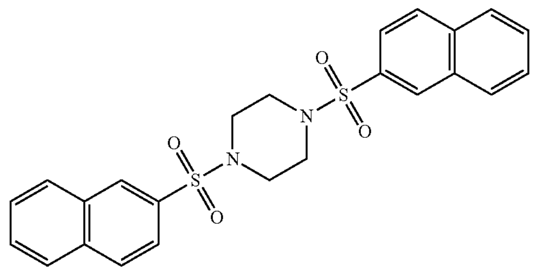 [SMILES: O=S(=O)(c1ccc2ccccc2c1)N1CCN(S(=O)(=O)c2ccc3ccccc3c2)CC1] |
| CSC13 | 39863 | 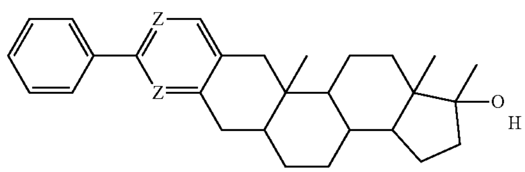 |
| CSC14 | 51535 | 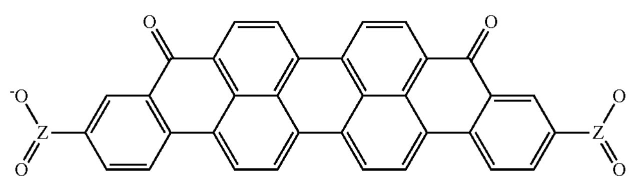 |
| CSC15 | 63875 | 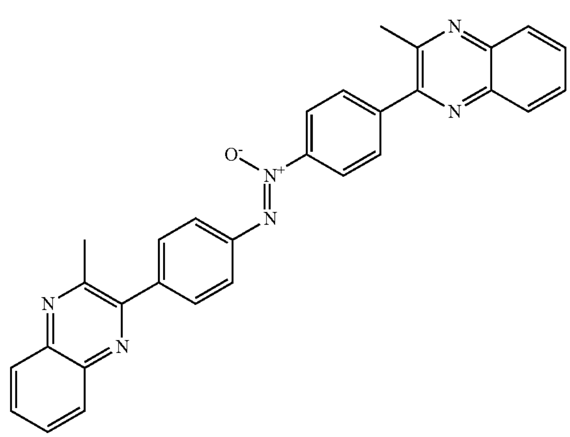 [SMILES: Cc1nc2ccccc2nc1-c1ccc(/N=[N+](\[O-])c2ccc(-c3nc4ccccc4nc3C)cc2)cc1] |
| CSC16 | 72254 | 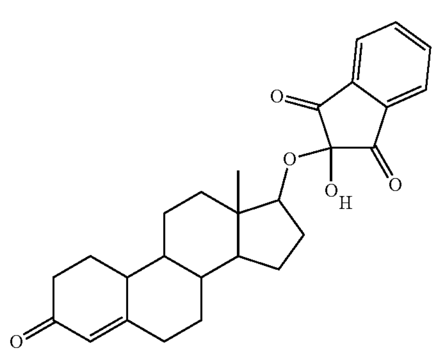 |

-continued

| cmp-no. | NCS no. | Chemical structure |
|---|---|---|
| CSC17 | 74702 | 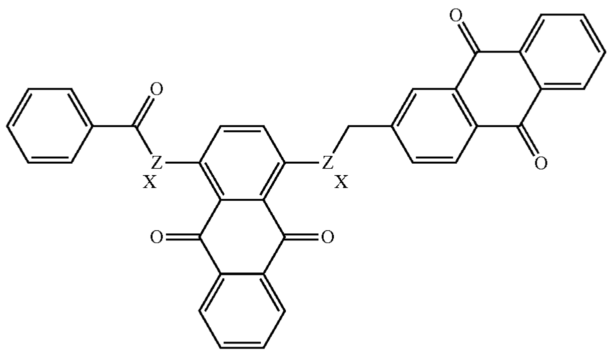 |
| CSC18 | 79050 | 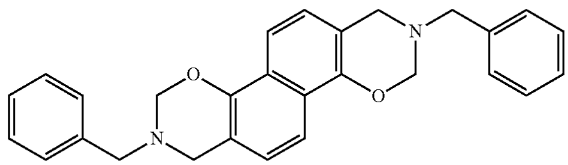 [SMILES: c1ccc(CN2COc3c(ccc4c5c(ccc34)CN(Cc3ccccc3)CO5)C2)cc1] |
| CSC19 | 90318 | 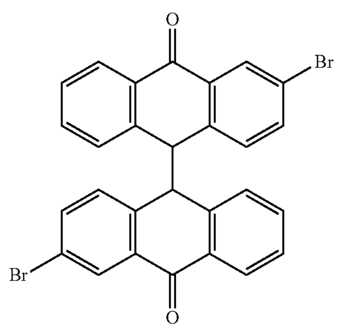 [SMILES: O=C1c2ccccc2C(C2c3ccccc3C(=O)c3cc(Br)ccc32)c2ccc(Br)cc21] |
| CSC20 | 94820 | 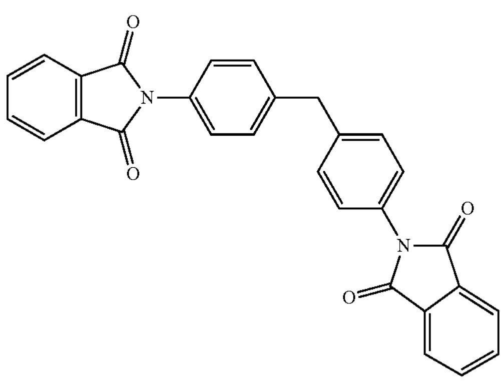 [SMILES: O=C1c2ccccc2C(=O)N1c1ccc(Cc2ccc(N3C(=O)c4ccccc4C3=O)cc2)cc1] |
| CSC21 | 95090 | 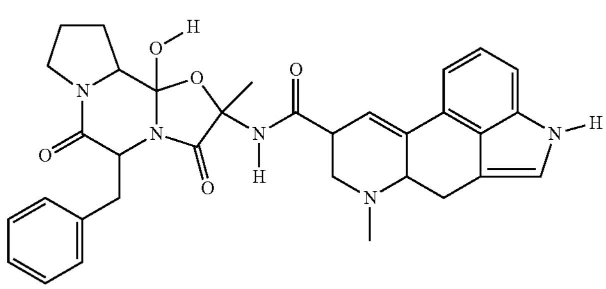 [SMILES: CN1CC(C(=O)NC2(C)OC3(O)C4CCCN4C(=O)C(Cc4ccccc4)N3C2=O)C=C2c3cccc4[nH]cc(c34)CC21] |

-continued
| cmp-no. | NCS no. | Chemical structure |
|---|---|---|
| CSC22 | 99515 | 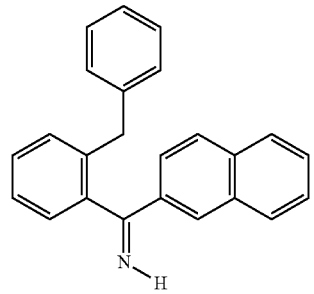 [SMILES: [H]/N=C(\c1ccc2ccccc2c1)c1ccccc1Cc1ccccc1] |
| CSC23 | 99543 | 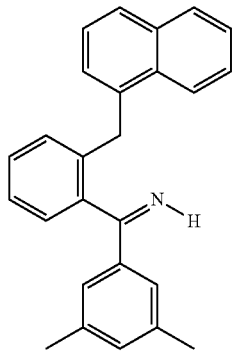 [SMILES: [H]/N=C(\c1cc(C)cc(C)c1)c1ccccc1Cc1cccc2ccccc12] |
| CSC24 | 99550 | 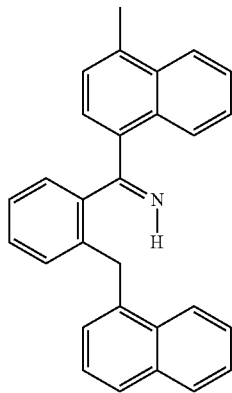 [SMILES: [H]/N=C(\c1ccccc1Cc1cccc2ccccc12)c1ccc(C)c2ccccc12] |
| CSC25 | 105550 | 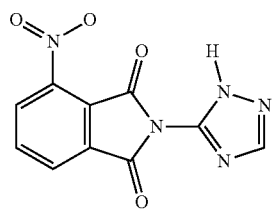 |

-continued
| cmp-no. | NCS no. | Chemical structure | |
|---|---|---|---|
| CSC26 | 111326 | 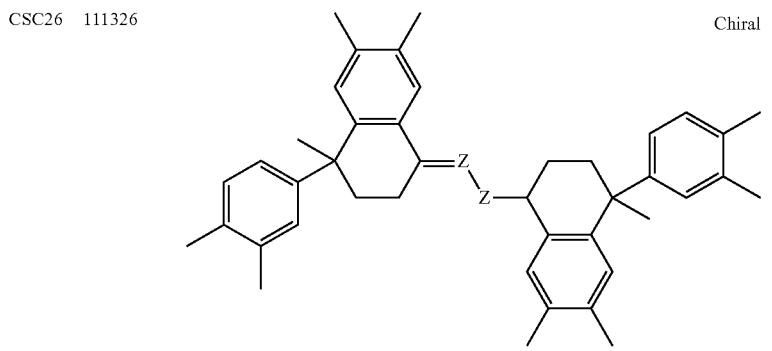 | Chiral |
| CSC27 | 115448 | 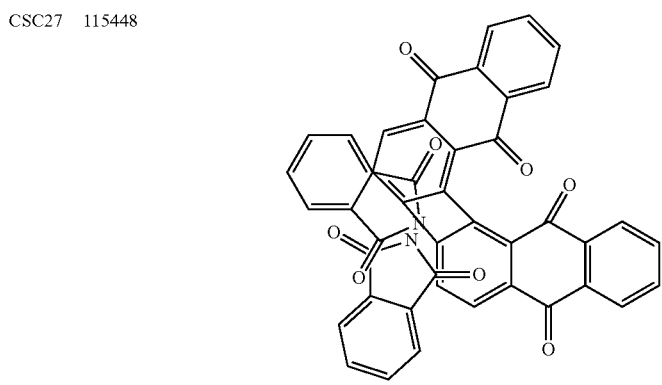 | |
| CSC28 | 119886 | 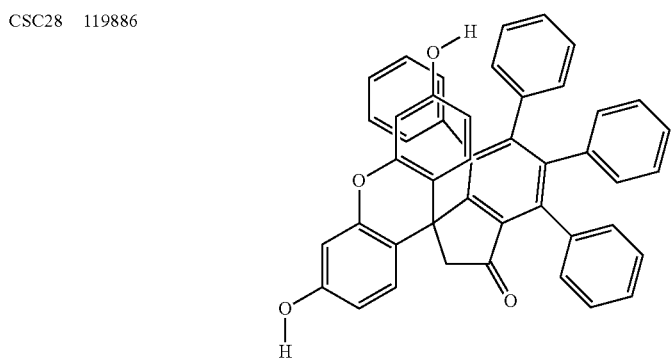 | |
| CSC29 | 122140 | 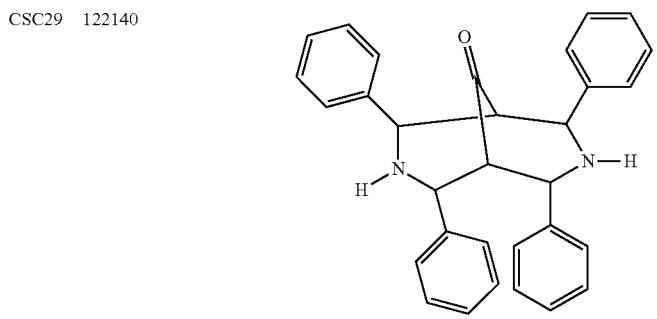 | |

-continued
| cmp-no. | NCS no. | Chemical structure |
|---|---|---|
| CSC30 | 125252 | 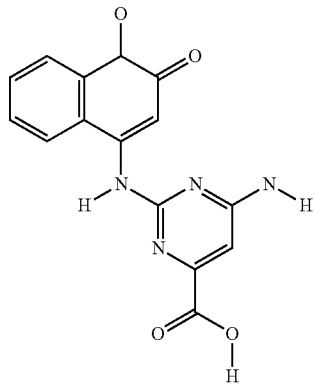 [SMILES: Nc1cc(C(=O)O)nc(NC2=CC(=O)C(O)c3ccccc32)n1] |
| CSC31 | 128609 | 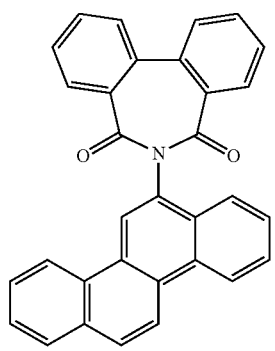 [SMILES: O=c1c2ccccc2c2ccccc2c(=O)n1-c1cc2c3ccccc3ccc2c2ccccc12] |
| CSC32 | 132230 | 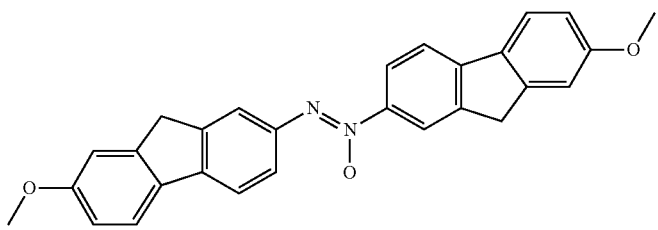 |
| CSC33 | 135371 | 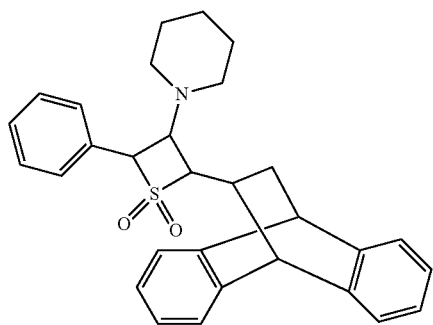 [SMILES: O=S1(=O)C(c2ccccc2)C(N2CCCCC2)C1C1CC2c3ccccc3C1c1ccccc12] |

-continued
| cmp-no. | NCS no. | Chemical structure |
|---|---|---|
| CSC34 | 234766 | 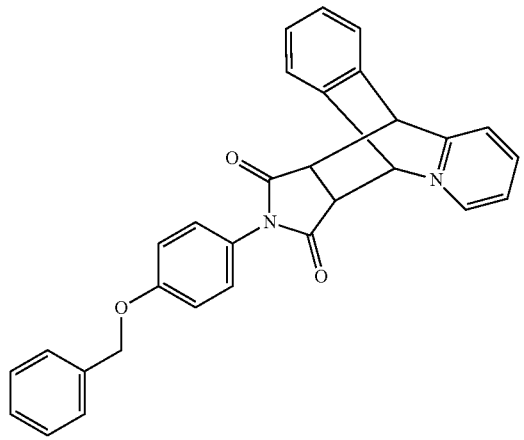 |
| CSC35 | 282058 | 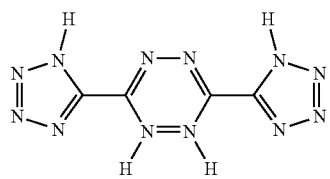 |
| CSC36 | 299137 | 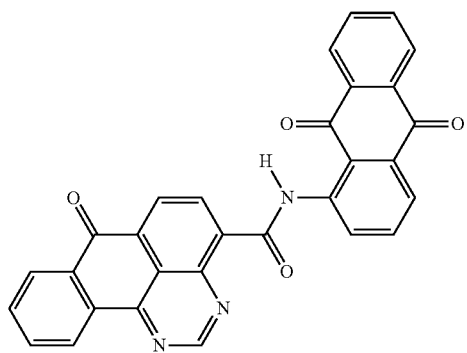 [SMILES: O=C1c2ccccc2C(=O)c2c(NC(=O)c3ccc4c5c(ncnc35)-c3ccccc3C4=O)cccc21] |
| CSC37 | 300545 | 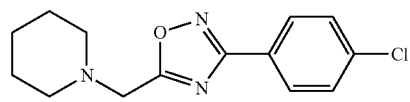 [SMILES: Clc1ccc(-c2noc(CN3CCCCC3)n2)cc1] |
| CSC38 | 309883 | 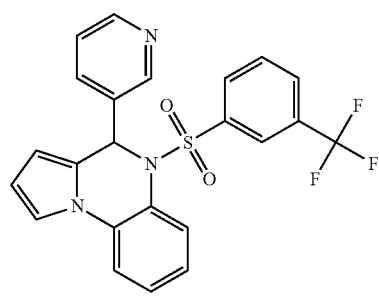 [SMILES: O=S(=O)(c1cccc(C(F)(F)F)c1)N1c2ccccc2-n2cccc2C1c1cccnc1] |

-continued

| cmp-no. | NCS no. | Chemical structure |
|---|---|---|
| CSC39 | 351123 | 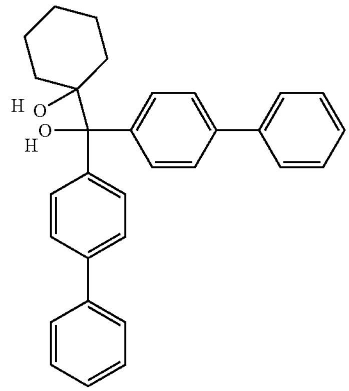 |
| CSC40 | 402959 | 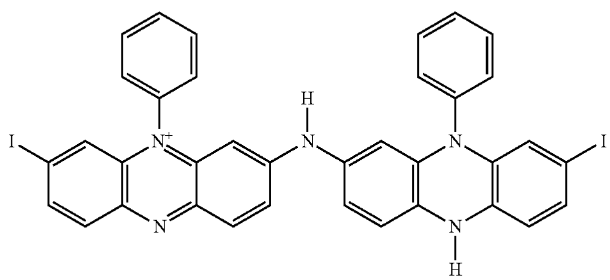 [SMILES: Ic1ccc2c(c1)N(c1ccccc1)c1cc(Nc3ccc4nc5ccc(I)cc5[n+](-c5ccccc5)c4c3)ccc1N2] |

| Compound (NCS) | Sirt2 | Sirt3 | Sirt5 | Sirt6 |
|---|---|---|---|---|
| CSC1 (11241) | inhibition[a] | inhibition | inhibition | inhibition |
| CSC2 (12339) | inhibition | — | — | — |
| CSC3 (12363) | — | — | — | — |
| CSC4 (13726) | inhibition | — | — | — |
| CSC5 (13728) | n.c.[b] | n.c. | n.c. | n.c. |
| CSC6 (23128) | inhibition | — | — | inhibition |
| CSC7 (23217) | inhibition | — | — | — |
| CSC8 (26645) | inhibition | — | — | — |
| CSC9 (35049) | inhibition | — | activation[c] | — |
| CSC10 (35489) | inhibition | inhibition | — | inhibition |
| CSC11 (35949) | — | — | — | — |
| CSC12 (37245) | — | — | — | — |
| CSC13 (39863) | inhibition | — | — | — |
| CSC14 (51535) | inhibition | — | inhibition | — |
| CSC15 (63875) | — | — | — | — |
| CSC16 (72254) | — | — | — | — |
| CSC17 (74702) | — | — | — | — |
| CSC18 (79050) | — | — | — | — |
| CSC19 (90318) | — | — | — | — |
| CSC20 (94820) | — | — | — | — |
| CSC21 (95090) | inhibition | — | inhibition | inhibition |
| CSC22 (99515) | inhibition | — | — | — |
| CSC23 (99543) | inhibition | — | — | — |
| CSC24 (99550) | inhibition | — | — | — |
| CSC25 (105550) | — | — | — | — |
| CSC26 (11326) | — | — | — | — |
| CSC27 (115448) | inhibition | — | — | inhibition |
| CSC28 (119886) | inhibition | — | — | activation |
| CSC29 (122140) | — | — | — | — |
| CSC30 (125252) | — | — | — | — |
| CSC31 (128609) | — | — | — | — |
| CSC32 (132230) | inhibition | — | — | — |
| CSC33 (135371) | — | — | activation | activation |
| CSC34 (234766) | inhibition | — | — | activation |
| CSC35 (282058) | — | — | — | — |
| CSC36 (299137) | — | — | — | — |
| CSC37 (300545) | inhibition | — | — | — |
| CSC38 (309883) | inhibition | — | activation | activation |
| CSC39 (351123) | — | — | — | — |
| CSC40 (402959) | n.c. | n.c. | n.c. | n.c. |

Further contemplated are sirtuin inhibitors disclosed below (see, e.g., Yasuda, et al., *Analytical Chem.*, 83:7400-7407 (2011)): quercetin and vitexin, as SIRT6 inhibitors.

Further contemplated are sirtuin inhibitors disclosed below (see, e.g., Kalle, et al. *Biochem. Biophys. Res. Comm.*, 401:13-19 (2010):

KS-JGB-1741

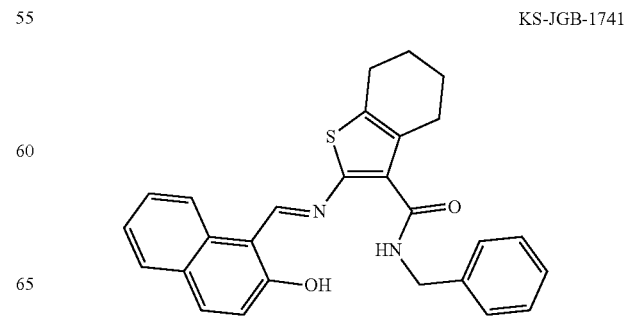

Further contemplated are sirtuin inhibitors disclosed below (see, e.g., Asaba, et al., *J. Am. Chem. Soc.,* 131:6989-6996 (2009)):

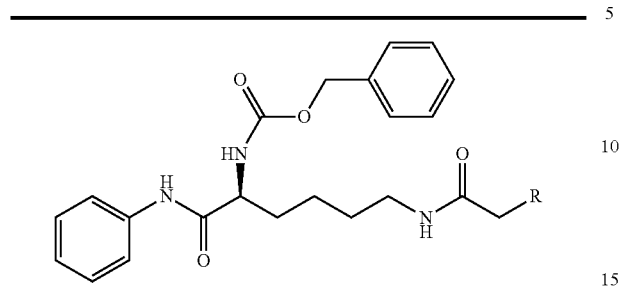

| compound | R | inhibition at 300 μM (%) | IC$_{50}$ (μM) |
| --- | --- | --- | --- |
| 2a | —CN | 50 ± 7.9 | 300 ± 6.2 |
| 2b | —CF$_3$ | 44 ± 17 | >300 |
| 2c | —SCH$_3$ | 32 ± 20 | >300 |
| 2d | —SOCH$_3$ | 46 ± 3.0 | >300 |
| 2e | —SO$_2$CH$_3$ | 56 ± 1.9 | n.D.[d] |
| 2f | 2-CF$_3$Ph | 49 ± 13 | >300 |
| 2g | 4-CF$_3$Ph | 41 ± 20 | >300 |
| 2h | 2-NO$_2$Ph | 40 ± 12 | >300 |
| 2i | 4-NO$_2$Ph | 51 ± 17 | N.D.[d] |
| 2j | —COOCH$_3$ | 92 ± 1.2 | 35 ± 5.2 |
| 2k | —COOEt | 91 ± 1.3 | 3.9 ± 0.29 |
| 2l | —COOn-Pr | 73 ± 0.72 | 62 ± 3.7 |
| 2m | —COOi-Pr | 72 ± 5.1 | 47 ± 5.3 |
| 2n | —COOn-Bu | 64 ± 6.1 | 73 ± 3.2 |
| 2o | —COOt-Bu | 6.0 ± 0.64 | >300 |
| 2p | —COOCH$_2$-c-Pr | 93 ± 1.2 | 14 ± 2.6 |
| 2q | —COOCH$_2$CF$_3$ | 94 ± 1.5 | 15 ± 3.1 |
| 2r | —COOCH$_2$Ph | 71 ± 4.3 | 96 ± 4.8 |
| 2s | —CONH$_2$ | 25 ± 2.3 | >300 |
| 2t | —CONHCH$_3$ | 24 ± 2.5 | >300 |
| 2u | —CON(CH$_3$)$_2$ | 20 ± 1.3 | >300 |
| 2v | —COCH$_3$ | 45 ± 6.0 | >300 |
| 2w | —COOEt | 67 ± 1.2 | 88 ± 3.9 |
| 2x | —COn-Pr | 78 ± 5.2 | 56 ± 5.3 |
| 2y | —COCF$_3$ | 7.9 ± 0.92 | >300 |
| 2z | —COPh | 37 ± 7.4 | >300 |

[a]SIRT1 was preincubated with NAD$^+$ and compounds 2a-z, and then acetylated lysine substrate was added.
[b]Values are means ± SD determined from at leas three experiments.
[c]Nicotinamide[22] (IC$_{50}$ = 25 ± 5.1 μM) and EX-527[12] (IC$_{50}$ = 1.4 ± 0.23 μM) were used as positive controls.
[d]N.D. = not determined.

, and in particular 2k.

Further contemplated are sirtuin inhibitors as disclosed below (see, e.g., Gutierrez, et al., *J. Org. Chem.,* 74:5267-5275 (2009)):

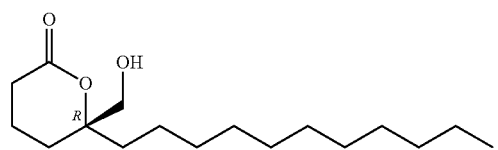

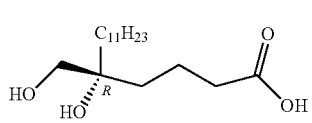

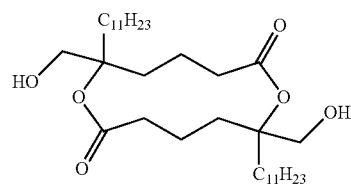

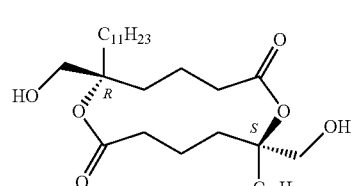

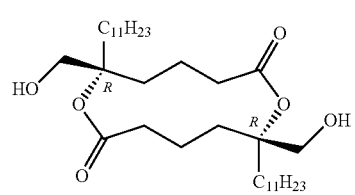

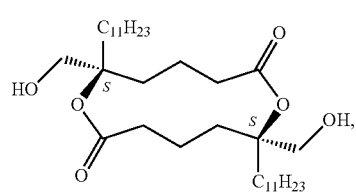

and in particular compounds 4, 5, and ent-5 as SIRT2 inhibitors.

Further contemplated are sirtuin inhibitors as disclosed below (see, e.g., Zhang, et al., *Biochem. Biophys. Res. Comm.,* 386:729-733 (2009)):

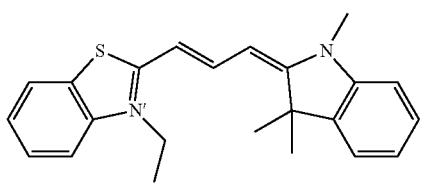
(AC-93253).
Further contemplated are sirtuin inhibitors as disclosed below (see, e.g., Huber, et al., *J. Med. Chem.*, 53:1383-1386 (2010)):
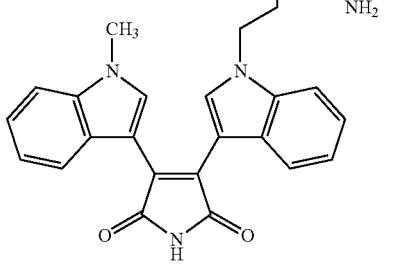
1
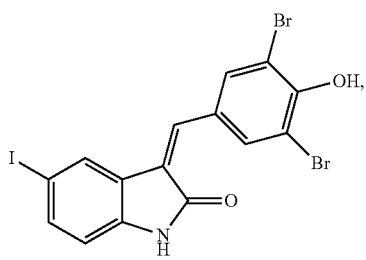
2
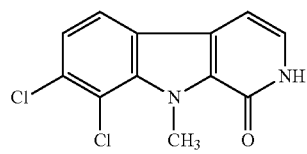
3
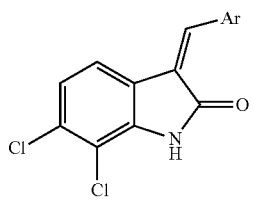
4-14
TABLE 1
| | | Sirtuin Inhibition | | |
|---|---|---|---|---|
| | | IC$_{50}$ ± SE [μM] or inhibition [%] @ 50 μM | | |
| Compound | Ar | SIRT1 | SIRT2 | SIRT3 |
| 2 | — | 41.6 ± 0.17 | 15.6 ± 1 | 25.1 ± 0.6 |
| 3 | — | NA$^a$ | 87.2 ± 9.5 | NA |
| Sensitivity | — | NA | 122.7 ± 23.6 | 26.4% |
| 4 | ![Br,OH,Br phenyl] | 40.6 ± 0.6 | 28.4 ± 2.5 | 23.6 ± 0.4 |
| 5 | ![4-OH phenyl] | NA | 34.7% | 13.5% |
| 6 | ![3,4,5-trimethoxyphenyl] | NA | NA | NA |
| 7 | ![4-F phenyl] | 24.4% | 33.4 ± 5.6 | NA |

TABLE 1-continued

Sirtuin Inhibition

| Compound | Ar | SIRT1 | SIRT2 | SIRT3 |
|---|---|---|---|---|
| | | \multicolumn{3}{c}{IC$_{50}$ ± SE [μM] or inhibition [%] @ 50 μM} |
| 8 | 4-(N,N-dimethylamino)phenyl | 20.7% | NA | NA |
| 9 | 4-nitrophenyl | 30.2% | 10.4 ± 1.4 | NA |
| 10 | 3,5-dimethyl-1H-pyrrol-2-yl | 19.9% | 135.4 ± 14.8 | NA |
| 11 | pyridin-2-yl | 22.7% | 30.6% | NA |
| 12 | pyridin-4-yl | 19.6% | 16.5% | NA |
| 13 | 4-(trifluoromethyl)phenyl | 45.4% | 16.3% | NA |
| 14 | 3,5-bis(trifluoromethyl)phenyl | 19.8% | 10.1% | NA |

$^a$Inhibition of <10% at 50 μM.

Other inhibitors of sirtuin(s) include the cyclic lipopeptide surfactin or derivatives thereof (see, Chakrabarty et al., *Molec. Biochem. Parasitol.*, 158:139-151 (2008).

Other inhibitors of sirtuin(s) include microRNA, such as disclosed in, e.g., Gambari, et al., *Biochem. Pharmacol.*, 82:1416-1429 (2011), Yamakuchi et al., *PNAS*, 105(36): 13421-13426 (2008), Xu, et al., *J. Cell. Biol.*, 193:409-124 (2011), or more specifically miR-34a, miR-22, or a derivative thereof as a sirtuin inhibitor.

B2, AGK2, and BML-266 are each SIRT2 inhibitors. EX-527 and (S)-35 are each SIRT1 inhibitors. Specifically contemplated are administration of a SIRT2 inhibitor selected from B2, AGK2, BML-266, or combinations thereof and a SIRT1 inhibitor selected from EX-527, (S)-35, and combinations thereof.

Since p53 is at least partially responsible for the ability of dual SIRT1/SIRT2 inhibitors to block HCMV replication (FIG. 6) and other sirtuins have been shown to alter the activity of p53 (see, e.g., Li et al., PLoS One 5, e10486, 2010), it is further contemplated that drugs inhibiting combinations of sirtuins in addition to SIRT1/SIRT2 dual inhibitors inhibit HCMV replication and the replication of other viruses that depend on the inactivation of p53. Specifically contemplated are administration of drugs that inhibit two or more sirtuins, including SIRT1 plus SIRT2, SIRT1 plus SIRT2 plus another sirtuin, SIRT1 plus one or more sirtuins that do not include SIRT2, SIRT2 plus one or more sirtuins that do not include SIRT1, or a combination of two or more sirtuins that do not include SIRT1 or SIRT2. As such, these combinations of sirtuin inhibitors are disclosed herein as antiviral therapeutics. Thus the present disclosure includes methods of treating a viral infection by administering one or more inhibitors of two or more sirtuins. Further contemplated are methods of administering inhibitors of multiple sirtuins and further administering one or more activators of one or more of the sirtuins that are not inhibited, or combinations of drugs that inhibit and activate different sirtuins. For example, contemplated are methods of treating a viral infection comprising administering a SIRT1 inhibitor, a SIRT2 inhibitor, and a SIRT3 activator (agonist) to subject in need thereof.

The present disclosure includes methods of treating HCMV infections using activators of any, a subset or all of seven sirtuins. Also provided is the use of therapeutics that simultaneously inhibit SIRT1 and SIRT2 (or, more generally, simultaneously inhibiting two or more sirtuins) to treat HCMV infections. These inhibitors include without limitation small molecules, nucleic acids, proteins, and peptide based activators. Beyond those described herein, additional small molecule activators can be found by screening of compound libraries and/or design of molecules that bind to specific pockets in the structures of these enzymes. The properties of these molecules can be optimized through derivatization, including iterative rounds of synthesis and experimental testing.

Figure 7:
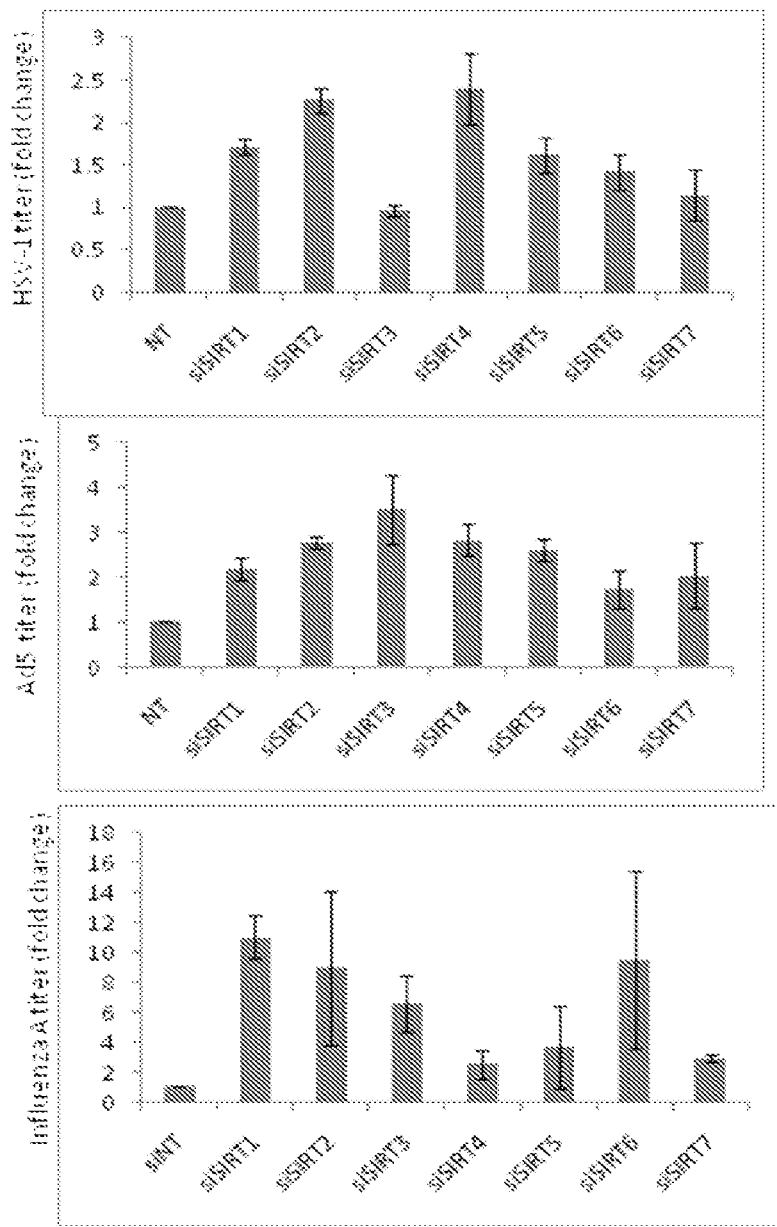
FIG. 7 illustrates that inhibition of sirtuins enhances the production of infectious herpes simplex virus type 1 (HSV1), adenovirus type 5 (Ad5) and influenza A (Flu A) progeny. MRC5 fibroblasts were transfected with siRNAs (the most robust siRNAs based on their activity in the HCMV assay) targeting each of the seven sirtuins. 72 h later, cells were infected with: top panel, HSV1 KOS strain at a multiplicity of 1 infectious unit per cell, and after an additional 22 h supernatants were collected and virus yields were determined by infectious center assay in MRC5 cells; middle panel, Ad5 at a multiplicity of 5 infectious units per cell, and after an additional 72 h, supernatants were collected and virus yields were determined by infectious center assay in HeLa cells; bottom panel, influenza WSN/33/A strain at a multiplicity of 0.5 infectious unit per cell and after an additional 22 h supernatants were collected and virus yields were determined by TCID50 assay in MDCK cells.

In addition to HCMV, siRNA screens were performed to test whether sirtuins also inhibit the replication of herpes simplex type 1 (HSV1), adenovirus (Ad5) and influenza A (Flu A) viruses. Each of these viruses generated elevated yields in response to knock down of multiple, individual siRNAs (FIG. 7). This result leads to a conclusion that sirtuin activators will inhibit not only HCMV, but also herpes simplex viruses, adenoviruses and influenza viruses. Given the diversity of these viruses (both slow and fast growing; both RNA and DNA viruses), the results predict that sirtuin agonists will exhibit broad spectrum antiviral activity. Thus, the present disclosure includes the use of sirtuin agonists as broad spectrum antiviral therapeutics.

Figure 8:
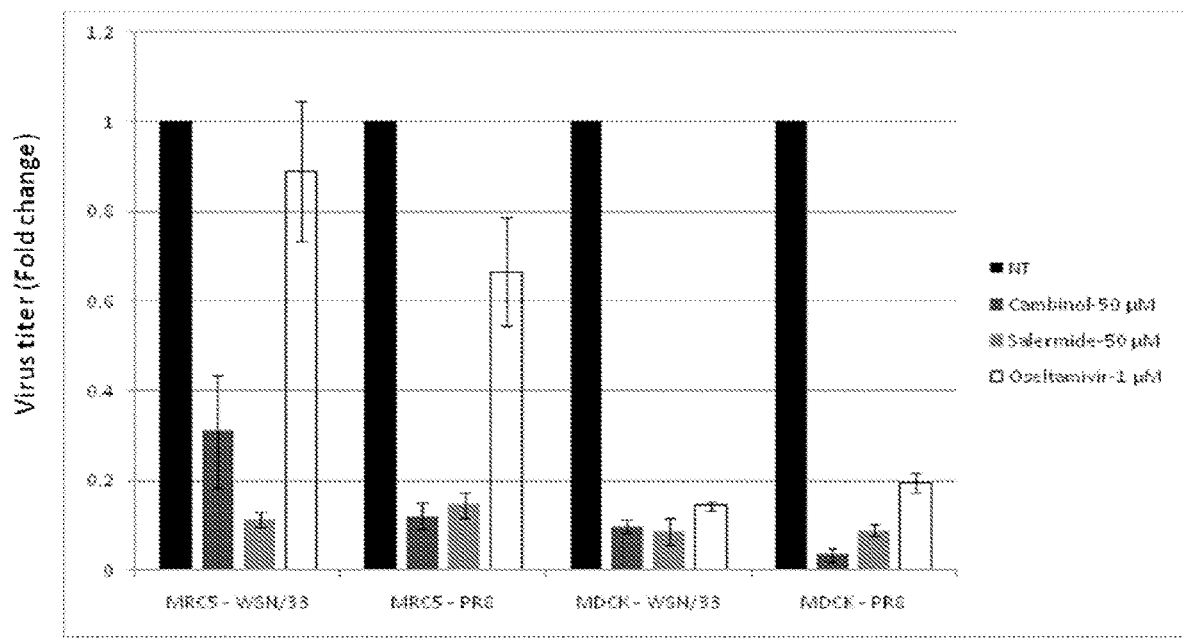
FIG. 8 illustrates dual Sirt1/Sirt2 inhibitors, Cambinol and Salermide, block the production of infectious Influenza A progeny. MRC5 fibroblasts and MDCK cells were infected with the influenza WSN/33/A strain at a multiplicity of 0.01 $TCID_{50}$/cell or PR8 strain at 0.1 $TCID_{50}$/cell. The medium of the cells was replaced with fresh medium containing the solvent (DMSO) or drugs dissolved in solvents at 1 hpi, and the yield of influenza A was determined at 24 hpi by standard $TCID_{50}$ method on MDCK cells. The marketed neuraminidase inhibitor, oseltamivir (TamiFlu®), was used as a comparator for the efficacy of tested compounds in the assay.
Figure 9:
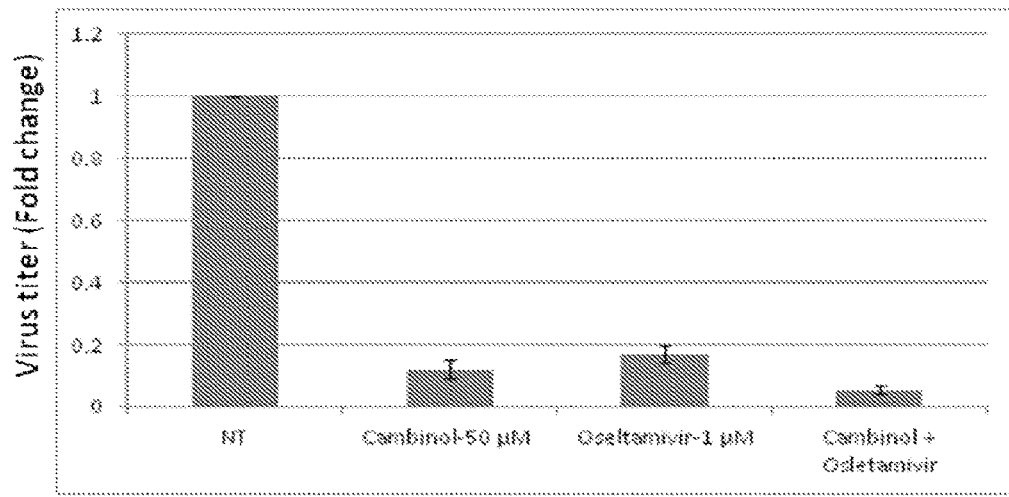
FIG. 9 illustrates that the dual Sirt1/Sirt2 inhibitor, Cambinol, cooperates with oseltamivir to block the production of infectious Influenza A progeny. MDCK cells were infected with the influenza WSN/33/A strain at a multiplicity of 0.001 $TCID_{50}$/cell. The medium of the cells was replaced with fresh medium containing the solvent (DMSO) or drugs dissolved in solvents at 1 hpi, and the yield of influenza A was determined at 24 hpi by standard $TCID_{50}$ method on MDCK cells.
Figure 10:
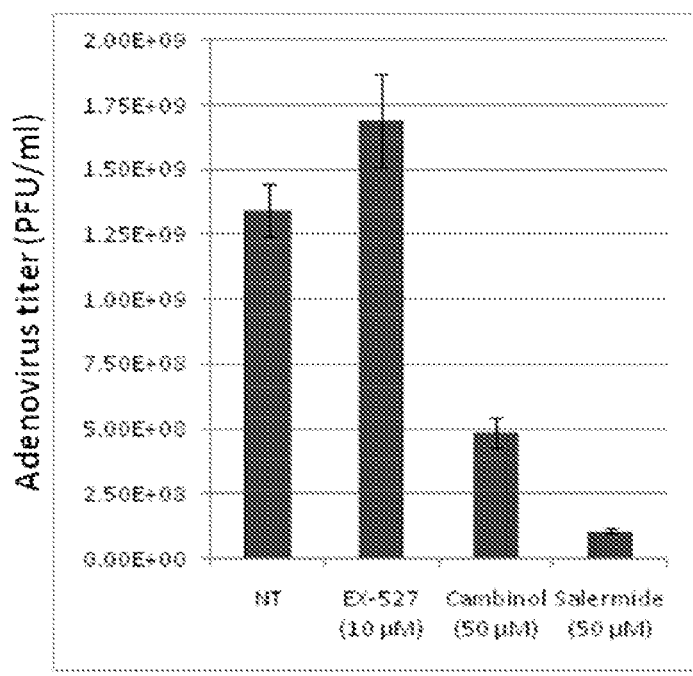
FIG. 10 illustrates that a SIRT1 antagonist enhances the production of infectious adenovirus (Ad5) progeny, but dual SIRT1/SIRT2 antagonists block the production of progeny. MRC5 fibroblasts were infected with Ad5 at a multiplicity of 5 IU/cell. The medium of the cells was replaced with fresh medium containing the solvent (DMSO) or drugs dissolved in solvents at 2 hpi, and the yield of Ad5 was determined at 72 hpi.

In addition to HCMV, the dual SIRT1/SIRT2 inhibitors cambinol and saleramide inhibited the production of infectious progeny for two Influenza A viruses, WSN/33 and PR8, in two different cell types, MRC5 fibroblasts and MDCK epithelial cells. The dual inhibitors reduced virus replication to a greater extent than did oseltamivir (TamiFlu®) which was included as a comparator (FIG. 8), and cambinol cooperated with oseltamivir to inhibit influenza A (FIG. 9). The dual inhibitors also blocked the production of adenovirus progeny (FIG. 10). Thus, dual SIRT1/SIRT2 inhibitors inhibit not only HCMV, but also influenza A and adenoviruses, making dual SIRT1/SIRT2 inhibitors broad spectrum antivirals that are useful for treatment as a single agent or in combination with other agents, as described further below.

Embodiments herein include methods of treating viral infections, including HCMV and adenovirus infections, using dual SIRT1 and 2 inhibitors (or more generally, inhibitors of two or more sirtuins), and optionally in combination with activators of another sirtuin. These sirtuin modulators include without limitation small molecules, nucleic acids, proteins, and derivatives thereof. Additional small molecule activators and inhibitors can be found by screening of compound libraries and/or design of molecules that bind to specific pockets in the structures of these enzymes. The properties of these molecules can be optimized through derivatization, including iterative rounds of synthesis and experimental testing.

Sirtuin agonists, dual SIRT1 and SIRT2 inhibitors, and inhibitors of two or more sirtuins have utility as anti-viral drugs.

The work herein is the first to show that the yields of HCMV are induced by inhibition of individual sirtuins and therefore indicate that induction of sirtuin levels or activity or both would inhibit the production of HCMV, herpes simplex virus, adenovirus, and influenza virus progeny. Modulation of each of the seven sirtuins can influence viral replication and therefore predict that induction of any one of the different known sirtuin activities will inhibit the production of HCMV progeny. These results also raise the possibility that induction of multiple sirtuins will synergistically inhibit the production of HCMV progeny. Importantly, simultaneous inhibition of SIRT1 and SIRT2 inhibits HCMV, in spite of the fact that inhibition of either separately increases virus yield.

Embodiments include inhibition of HCMV by agonists of one or more sirtuin (SIRT1-7), and the agonists. Some agonists may only target one sirtuin, but one or more agonists targeting multiple sirutins may also be provided. An embodiment includes an agonist of one or more of the mitochondrial sirtuins (SIRT3-5), because the siRNA data reveals that modulation of SIRT3 and SIRT5 has the greatest effect on HCMV yield.

Embodiments include inhibition of a virus by antagonists of SIRT1 and SIRT2, or antagonists of two or more sirtuins (SIRT1-7), and the agents capable of causing the inhibition. The virus may be HCMV. The virus may be one that must inactivate p53 in order to produce an optimal yield of infectious progeny or maintain itself within an infected cell. The virus may be any virus. Inhibition can be accomplished using drugs that inhibit both sirtuins or by using a combination of two drugs, one of which inhibits SIRT1 and the other of which inhibits SIRT2.

Embodiments include methods of treating viral infections. Embodiments include methods of treating HCMV infections in human patients. The methods include a step of administering agonists, or activators, of any sirtuin, agonists of a subset sirtuins or agonists all of seven sirtuins to a patient. These agonists include without limitation at least one of small molecules, nucleic acids, proteins, or peptide based activators. Beyond those described herein, additional small molecule activators can be found by screening of compound libraries and/or design of molecules that bind to specific pockets in the structures of these enzymes. The properties of these molecules can be optimized through derivatization, including iterative rounds of synthesis and experimental testing.

Embodiments include methods of treating viral infections. Embodiments include methods of treating HCMV infections in mammals, or more specifically human patients. Embodiments include methods of treating viral infections where the virus requires p53 inactivation. The methods include a step of administering antagonists of sirtuins, in particular antagonists of both SIRT1 and SIRT2 to a patient. These antagonists include without limitation at least one of small molecules, nucleic acids, proteins, or peptide based activators. Beyond those described herein, additional small molecule antagonists can be found by screening of compound libraries and/or design of molecules that bind to specific pockets in the structures of these enzymes. The properties of these molecules can be optimized through derivatization, including iterative rounds of synthesis and experimental testing.

Embodiments include anti-viral drugs that may be used for treating viral infections. The anti-viral drugs may be agonists or antagonists of any sirtuin, agonists or antagonists of a subset sirtuins or agonists or antagonists all of seven sirtuins. These activators include without limitation small molecules, nucleic acids, proteins, or peptide based activators. Beyond those described herein, additional small molecule activators can be found by screening of compound libraries and/or design of molecules that bind to specific pockets in the structures of these enzymes. The properties of these molecules can be optimized through derivatization, including iterative rounds of synthesis and experimental testing.

Further disclosed herein are methods that further comprise contacting a virus with a second agent, e.g., an antiviral agent that is not the SIRT1 and SIRT2 inhibitors or the sirtuin agonist or a second agent that is a different SIRT1 and/or SIRT2 inhibitor or sirtuin agonist as disclosed herein. Contemplated second agents include, without limitation, acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, assembly inhibitors (e.g., rifampicin), and zidovudine.

Further disclosed herein are methods of treating HCMV or other virus infection that is present within the tumor of a subject, e.g., a human. HCMV DNA, RNA and protein have been shown to be present in some human tumors, including malignant glioma (Cobbs CS. Herpesviridae 2:10, 2011), and the presence of the virus is thought to promote the pathogenesis of these cancers. Therefore, inhibition of HCMV gene expression, replication, growth or spread by dual sirtuin antagonists (or, more generally, by simultaneously inhibiting two or more sirtuins) in patients with cancers, where at least a portion of the tumor cells (malignant tumor cells or tumor-associated stromal cells) contain the HCMV genome, is predicted to be therapeutically beneficial. Dual sirtuin inhibitors could be used alone or in combination with other anti-viral or anti-tumor therapeutics. A preferred embodiment of this therapeutic application of dual sirtuin inhibitors would be treatment of malignant glioma, but any tumor containing the HCMV genome in at least a portion of its cells is disclosed herein as a target for this therapy. A second preferred embodiment of this therapeutic application would be treatment of tumors containing the genome of HCMV, but tumors with the genome any virus whose replication can be inhibited by dual sirtuin inhibitors, are disclosed herein as a target for this therapy. A preferred therapeutic application comprises inhibitors of SIRT1 and SIRT2, inhibitors of SIRT1 plus SIRT2 plus another sirtuin, inhibitors of SIRT1 plus one or more sirtuins that do not include SIRT2, inhibitors of SIRT2 plus one or more sirtuins that do not include SIRT1, or a combination of inhibitors of two or more sirtuins that do not include SIRT1 or SIRT2.

Embodiments include a pharmaceutical composition including any of the anti-viral drugs herein and a pharmaceutically acceptable carrier. The pharmaceutically acceptable carrier may include at least one of ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts, electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, waxes, polyethylene glycol, starch, lactose, dicalcium phosphate, microcrystalline cellulose, sucrose, talc, magnesium carbonate, kaolin, non-ionic surfactants, edible oils, physiological saline, bacteriostatic water, Cremophor EL™ (BASF, Parsippany, N.J.), or phosphate buffered saline (PBS).

The route for administering a drug or pharmaceutical composition may be by any route. The route of administration may be any one or more route including but not limited to oral, injection, topical, enteral, rectal, gastrointestinal, sublingual, sublabial, buccal, epidural, intracerebral, intracerebroventricular, intracisternal, epicutaneous, intradermal, subcutaneous, nasal, intravenous, intraarterial, intramuscular, intracardiac, intraosseous, intrathecal, intraperitoneal, intravesical, intravitreal, intracavernous, intravaginal, intrauterine, extra-amniotic, transdermal, intratumoral, and transmucosal.

Methods of Increasing Viral Yield

Also disclosed herein are methods of increasing virus yield by inhibiting sirtuin activity, e.g., inhibiting one or more of SIRT1, SIRT2, SIRT3, SIRT4, SIRT5, SIRT6, and SIRT7. Further contemplated are methods wherein neither SIRT1 nor SIRT2 are inhibited or only one of SIRT1 and SIRT2 are inhibited. In various cases, one or more of SIRT3, SIRT4, SIRT5, SIRT6, and SIRT7 are inhibited.

The results herein are the first to show that the yield of HCMV, herpes simplex virus, adenovirus, and influenza virus is induced by inhibition of sirtuins and therefore indicate that reduction of sirtuin protein levels or activity or both would enhance the production of HCMV, herpes simplex virus, adenovirus, and influenza virus progeny and other viruses that are inhibited by sirtuin activity. Importantly, the results herein are also the first to show that modulation of each of the seven sirtuins can influence viral replication and therefore provide a prediction that inhibition of any one of the different known sirtuin activities will enhance the production of HCMV, herpes simplex virus, adenovirus, and influenza virus progeny.

Since production of very different viruses (DNA genome and RNA genome; naked and enveloped) has been enhanced by inhibiting sirtuin activity, it is contemplated that the growth of additional viruses and their attenuated or otherwise modified derivatives also can be enhanced by inhibition of sirtuins. These additional viruses include but are not limited to: polio viruses, hepatitis A virus, rabies virus, measles virus, mumps virus, rubella virus, rotavirus, varicella zoster virus, yellow fever virus, lentiviruses including HIV, retroviruses and adeno-associated virus.

Inhibition of sirtuins to increase viral yields can be achieved by contacting a cell with an inhibitor of a sirtuin or inhibitor of sirtuin expression. Inhibition of sirtuin expression can be by RNAi, e.g., contacting one or more siRNA to one or more of the mRNAs encoding sirtuins. Specific siRNAs tested and shown in FIG. 1 are in Table 3.

TABLE 3

| Target | siRNA Sequence (5' to 3') | SEQ ID NO |
|---|---|---|
| Sirt1_1 | GUGUCAUGGUUCCUUUGCA [dT] [dT] | 1 |
|  | UGCAAAGGAACCAUGACAC [dT] [dT] | 2 |
| Sirt1_2 | CUGUGAAGCUGUACGAGGA [dT] [dT] | 3 |
|  | UCCUCGUACAGCUUCACAG [dT] [dT] | 4 |
| Sirt1_3 | CAACUAUACCCAGAACAUA [dT] [dT] | 5 |
|  | UAUGUUCUGGGUAUAGUUG [dT] [dT] | 6 |
| Sirt2_1 | CUACUCCUGCGUGCUACA  [dT] [dT] | 7 |
|  | UGUAGCAGCGCAGGAGUAG [dT] [dT] | 8 |
| Sirt2_2 | GGAGUAACCUCCCUCAUCU [dT] [dT] | 9 |
|  | AGAUGAGGGAGGUUACUCC [dT] [dT] | 10 |
| Sirt2_3 | CGCGUUUCUUCUCCUGUAU [dT] [dT] | 11 |
|  | AUACAGGAGAAGAAACGCG [dT] [dT] | 12 |
| Sirt3_1 | GCUUUCUGUGCCUAGUUGA [dT] [dT] | 13 |
|  | UCAACUAGGCACAGAAAGC [dT] [dT] | 14 |
| Sirt3_2 | CUCAAAGCUGGUUGAAGCU [dT] [dT] | 15 |
|  | AGCUUCAACCAGCUUUGAG [dT] [dT] | 16 |
| Surt3_3 | GACAAGACCUCAUGCCUGA [dT] [dT] | 17 |
|  | UCAGGCAUGAGGUCUUGUC [dT] [dT] | 18 |
| Sirt4_1 | GGGAUCAUCCUUGCAGGUA [dT] [dT] | 19 |
|  | UACCUGCAAGGAUGAUCCC [dT] [dT] | 20 |
| Sirt4_2 | GAGAAACUCGGAAAGCUGU [dT] [dT] | 21 |
|  | ACAGCUUUCCGAGUUUCUC [dT] [dT] | 22 |
| Sirt4_3 | CUUUGAGCACCUGGGAGAA [dT] [dT] | 23 |
|  | UUCUCCCAGGUGCUCAAAG [dT] [dT] | 24 |
| Sirt5_1 | GUGAGACCCGGCUGGGCAA [dT] [dT] | 25 |
|  | UUGCCCAGCCGGGUCUCAC [dT] [dT] | 26 |
| Sirt5_2 | CAGCAUCCCAGUUGAGAAA [dT] [dT] | 27 |
|  | UUUCUCAACUGGGAUGCUG [dT] [dT] | 28 |
| Sirt5_3 | GAGAUCCAUGGUAGCUUAU [dT] [dT] | 29 |
|  | AUAAGCUACCAUGGAUCUC [dT] [dT] | 30 |
| Sirt6_1 | CUGUCCAUCACGCUGGGUA [dT] [dT] | 31 |
|  | UACCCAGCGUGAUGGACAG [dT] [dT] | 32 |
| Sirt6_2 | CUCACUUUGUUACUUGUUU [dT] [dT] | 33 |
|  | AAACAAGUAACAAAGUGAG [dT] [dT] | 34 |
| Sirt6_3 | CCAAGUGUAAGACGCAGUA [dT] [dT] | 35 |
|  | UACUGCGUCUUACACUUGG [dT] [dT] | 36 |
| Sirt7_1 | GGGAGUACGUGCGGGUGUU [dT] [dT] | 37 |
|  | AACACCCGCACGUACUCCC [dT] [dT] | 38 |
| Sirt7_2 | GACGUAAUCACGUGCUCGA [dT] [dT] | 39 |
|  | UCGAGCACGUGAUUACGUC [dT] [dT] | 40 |
| Sirt7_3 | GACGUCAUGCGGCUCCUCA [dT] [dT] | 41 |
|  | UGAGGAGCCGCAUGACGUC [dT] [dT] | 42 |

A subset of sequences from Table 3 contemplated for use as inhibitors of sirtuin gene expression and increase in virus production are shown in Table 3A, below. The use of these siRNAs and any other siRNA able to inhibit sirtuin expression is contemplated.

TABLE 3A

| Target | SEQ ID NO: | siRNA Sequence (5' to 3') |
|---|---|---|
| Sirt1_2 | 3 | CUGUGAAGCUGUACGAGGA [dT] [dT] |
|  | 4 | UCCUCGUACAGCUUCACAG [dT] [dT] |
| Sirt2_1 | 7 | CUACUCCUGCGUGCUACA  [dT] [dT] |
|  | 8 | UGUAGCAGCGCAGGAGUAG [dT] [dT] |
| Sirt2_3 | 11 | CGCGUUUCUUCUCCUGUAU [dT] [dT] |
|  | 12 | AUACAGGAGAAGAAACGCG [dT] [dT] |
| Sirt3_1 | 13 | GCUUUCUGUGCCUAGUUGA [dT] [dT] |
|  | 14 | UCAACUAGGCACAGAAAGC [dT] [dT] |
| Sirt3_2 | 15 | CUCAAAGCUGGUUGAAGCU [dT] [dT] |
|  | 16 | AGCUUCAACCAGCUUUGAG [dT] [dT] |
| Sirt3_3 | 17 | GACAAGACCUCAUGCCUGA [dT] [dT] |
|  | 18 | UCAGGCAUGAGGUCUUGUC [dT] [dT] |
| Sirt4_1 | 19 | GGGAUCAUCCUUGCAGGUA [dT] [dT] |
|  | 20 | UACCUGCAAGGAUGAUCCC [dT] [dT] |
| Sirt4_2 | 21 | GAGAAACUCGGAAAGCUGU [dT] [dT] |
|  | 22 | ACAGCUUUCCGAGUUUCUC [dT] [dT] |
| Sirt4_3 | 23 | CUUUGAGCACCUGGGAGAA [dT] [dT] |
|  | 24 | UUCUCCCAGGUGCUCAAAG [dT] [dT] |
| Sirt5_1 | 25 | GUGAGACCCGGCUGGGCAA [dT] [dT] |
|  | 26 | UUGCCCAGCCGGGUCUCAC [dT] [dT] |
| Sirt5_2 | 27 | CAGCAUCCCAGUUGAGAAA [dT] [dT] |
|  | 28 | UUUCUCAACUGGGAUGCUG [dT] [dT] |
| Sirt5_3 | 29 | GAGAUCCAUGGUAGCUUAU [dT] [dT] |
|  | 30 | AUAAGCUACCAUGGAUCUC [dT] [dT] |
| Sirt6_1 | 31 | CUGUCCAUCACGCUGGGUA [dT] [dT] |
|  | 32 | UACCCAGCGUGAUGGACAG [dT] [dT] |
| Sirt6_2 | 33 | CUCACUUUGUUACUUGUUU [dT] [dT] |
|  | 34 | AAACAAGUAACAAAGUGAG [dT] [dT] |
| Sirt6_3 | 35 | CCAAGUGUAAGACGCAGUA [dT] [dT] |
|  | 36 | UACUGCGUCUUACACUUGG [dT] [dT] |
| Sirt7_1 | 37 | GGGAGUACGUGCGGGUGUU [dT] [dT] |
|  | 38 | AACACCCGCACGUACUCCC [dT] [dT] |

Inhibition of sirtuin expression can be by RNAi, e.g., contacting one or more shRNAs to one or more of the mRNAs encoding sirtuins. Sequences of shRNA for various sirtuin genes are shown in Table 4, below. The use of these shRNAs and any other shRNA able to inhibit sirtuin expression is contemplated.

TABLE 4

| Gene | Species | SEQ ID NO | shRNA sequence |
|---|---|---|---|
| Sirt1 | H. Sapiens | 43 | CCGGGCAAAGCCTTTCTGAATCTATCTCGAGATAGATTCAGAAAGGCTTTGCTTTTT |
|  |  | 44 | CCGGCCTCGAACAATTCTTAAAGATCTCGAGATCTTTAAGAATTGTTCGAGGTTTTT |
|  |  | 45 | CCGGGCGGGAATCCAAAGGATAATTCTCGAGAATTATCCTTTGGATTCCCGCTTTTT |

TABLE 4-continued

| Gene | Species | SEQ ID NO | shRNA sequence |
|---|---|---|---|
| | M. musculus | 46 | CCGGAGTGAGACCAGTAGCACTAATCTCGAGATTAGTGCTACTGGTCTCACTTTTTG |
| | | 47 | CCGGGCCATGTTTGATATTGAGTATCTCGAGATACTCAATATCAAACATGGCTTTTTG |
| | | 48 | CCGGGAGGGTAATCAATACCTGTTTCTCGAGAAACAGGTATTGATTACCCTCTTTTTG |
| Sirt2 | H. Sapiens | 49 | CCGGTATGACAACCTAGAGAAGTACCTCGAGGTACTTCTCTAGGTTGTCATATTTTTG |
| | | 50 | CCGGCAGAAGACATTGCTTATTGGACTCGAGTCCAATAAGCAATGTCTTCTGTTTTTG |
| | | 51 | CCGGCCTGTGGCTAAGTAAACCATACTCGAGTATGGTTTACTTAGCCACAGGTTTTTG |
| | M. musculus | 52 | CCGGCCTTCGTTCTTTAACCACTTTCTCGAGAAAGTGGTTAAAGAACGAAGGTTTTT |
| | | 53 | CCGGCCTCTATGCAAACCTGGAGAACTCGAGTTCTCCAGGTTTGCATAGAGGTTTTT |
| | | 54 | CCGGCGGCTGCTCATTAACAAGGAACTCGAGTTCCTTGTTAATGAGCAGCCGTTTTT |
| Sirt3 | H. Sapiens | 55 | CCGGCCCAACGTCACTCACTACTTTCTCGAGAAAGTAGTGAGTGACGTTGGGTTTTG |
| | | 56 | CCGGGCGGCTCTACACGCAGAACATCTCGAGATGTTCTGCGTGTAGAGCCGCTTTTTG |
| | | 57 | CCGGGTGGGTGCTTCAAGTGTTGTTCTCGAGAACAACACTTGAAGCACCCACTTTTTG |
| | M. musculus | 58 | CCGGCCTACTCCATATGGCTGACTTCTCGAGAAGTCAGCCATATGGAGTAGGTTTTTG |
| | | 59 | CCGGAGACAGCTCCAACACGTTTACCTCGAGGTAAACGTGTTGGAGCTGTCTTTTTG |
| | | 60 | CCGGGCCCAATGTCACTCACTACTTCTCGAGAAGTAGTGAGTGACATTGGGCTTTTTG |
| Sirt4 | H. Sapiens | 61 | CCGGCCCGATTGCAATACTGAACATCTCGAGATGTTCAGTATTGCAATCGGGTTTTT |
| | | 62 | CCGGCCGTGCTCGAAAGCCTCCATTCTCGAGAATGGAGGCTTTCGAGCACGGTTTTT |
| | | 63 | CCGGGAACCCTGACAAGGTTGATTTCTCGAGAAATCAACCTTGTCAGGGTTCTTTTT |
| | M. musculus | 64 | GTACCGGAGTAAACCACAACTGTCTATGCTCGAGCATAGACAGTTGTGGTTTACTTTTTTTG |
| | | 65 | CCGGGCAGCATATCCGGAACCTTAACTCGAGTTAAGGTTCCGGATATGCTGCTTTTTG |
| | | 66 | CCGGTTGACTTTCAGGCCGACAAAGCTCGAGCTTTGTCGGCCTGAAAGTCAATTTTTG |
| Sirt5 | H. Sapiens | 67 | CCGGGAGTCCAATTTGTCCAGCTTTCTCGAGAAAGCTGGACAAATTGGACTCTTTTT |
| | | 68 | CCGGGCTACAACAGATTCAGGTTTCTCGAGAAACCTGAATCTGTTCGTAGCTTTTT |
| | | 69 | CCGGCGTCCACACGAAACCAGATTTCTCGAGAAATCTGGTTTCGTGTGGACGTTTTT |
| | M. musculus | 70 | CCGGGCAGACAATCTGTTACGTGATCTCGAGATCACGTAACAGATTGTCTGCTTTTTG |
| | | 71 | CCGGCCAGTTGTGTTGTAGACGAAACTCGAGTTTCGTCTACAACACAACTGGTTTTG |
| | | 72 | CCGGCGACAGATTCAGGTTTCATTTCTCGAGAAATGAAACCTGAATCTGTCGTTTTG |
| Sirt6 | H. Sapiens | 73 | CCGGTGGAAGAATGTGCCAAGTGTACTCGAGTACACTTGGCACATTCTTCCATTTTTG |
| | | 74 | CCGGGCAGTCTTCCAGTGTGGTGTTCTCGAGAACACCACACTGGAAGACTGCTTTTTG |
| | | 75 | CCGGGCTGGGTACATCGCTGCAGATCTCGAGATCTGCAGCGATGTACCCAGCTTTTTG |
| | M. musculus | 76 | CCGGCATGTCCAACACAGCTCCTTTCTCGAGAAAGGAGCTGTGTTGGACATGTTTTTG |
| | | 77 | CCGGGCATGTTTCGTATAAGTCCAACTCGAGTTGGACTTATACGAAACATGCTTTTTG |
| | | 78 | CCGGGTTTGACACCACCTTCGAGAACTCGAGTTCTCGAAGGTGGTGTCAAACTTTTTG |
| Sirt7 | H. Sapiens | 79 | CCGGGTCCAGCCTGAAGGTTCTAAACTCGAGTTTAGAACCTTCAGGCTGGACTTTTTG |
| | | 80 | CCGGCGCCAAATACTTGGTCGTCTACTCGAGTAGACGACCAAGTATTTGGCGTTTTT |
| | | 81 | CCGGGCCTGAAGGTTCTAAAGAAGTCTCGAGACTTCTTTAGAACCTTCAGGCTTTTT |
| | M. musculus | 82 | CCGGCCTCCCTCTTTCTACTCCTTACTCGAGTAAGGAGTAGAAAGAGGGAGGTTTTG |
| | | 83 | CCGGTGCATCCCTAACAGAGAGTATCTCGAGATACTCTCTGTTAGGGATGCATTTTTG |
| | | 84 | CCGGCCTGGAGATTCCTGTCTACAACTCGAGTTGTAGACAGGAATCTCCAGGTTTTTG |

Gene sequences for each of the sirtuins in various species can be found at the Genbank Accession Nos. noted in Table 5, below. As such, siRNA and shRNA that inhibit gene expression of any of the genes referenced in Table 5, as well as sirtuin genes from other species, are specifically contemplated.

TABLE 5

| Gene | Species | Genbank Accession No |
|---|---|---|
| Sirt1 | Homo sapiens | NM_012238.4 |
| | Mus musculus | NM_019812.2 |
| | Canis lupus familiaris | XM_546130.3 |
| | Cricetulus griseus | XM_003501011.1 (Sirt1-like) |
| Sirt2 | Homo sapiens | NM_012237.3 |
| | Mus musculus | NM_022432.4 |
| | Canis lupus familiaris | XM_850289.2 |
| Sirt3 | Homo sapiens | NM_012239.5 |
| | Mus musculus | NM_001127351.1 |
| | Canis lupus familiaris | XM_850716.2 |
| Sirt4 | Homo sapiens | NM_012240.2 |
| | Mus musculus | NM_001167691.1 |
| | Canis lupus familiaris | XM_858071.2 |
| | Cricetulus griseus | XM_003495917.1 (Sirt4-like) |
| Sirt5 | Homo sapiens | NM_012241.4 |
| | Mus musculus | NM_178848.3 |
| | Canis lupus familiaris | XM_535891.3 |
| | Cricetulus griseus | XM_003497937.1 (Sirt5-like) |
| Sirt6 | Homo sapiens | NM_016539.2 |
| | Mus musculus | NM_181586.3 |
| | Canis lupus familiaris | XM_542163.3 |
| | Cricetulus griseus | XM_003506436.1 |
| Sirt7 | Homo sapiens | NM_016538.2 |
| | Mus musculus | NM_153056.2 |
| | Canis lupus familiaris | XM_540490.3 |
| | Cricetulus griseus | XM_003496941.1 (Sirt7-like) |

RNAi

RNA interference (RNAi), a post-transcriptional process triggered by the introduction of double-stranded RNA, leads to gene silencing in a sequence-specific manner. In many species the introduction of double-stranded structures, such as double-stranded RNA (dsRNA) molecules, has been shown to induce potent and specific antisense-mediated reduction of the function of a gene or its associated gene products. The RNAi compounds are often referred to as short interfering RNAs (siRNAs) or short hairpin RNAs (shRNAs). It has been shown that it is, in fact, the single-stranded RNA oligomers of antisense polarity of the siRNAs which are the potent inducers of RNAi (Tijsterman et al., Science, 2002, 295, 694-697). RNAi compounds (i.e., single- or double-stranded RNA or RNA-like compounds) and single-stranded RNase H-dependent antisense compounds bind to their RNA target by base pairing (i.e., hybridization) and induce site-specific cleavage of the target RNA by specific RNAses; i.e., both are antisense mechanisms (Vickers et al., 2003, J. Biol. Chem., 278, 7108-7118). Double-stranded ribonucleases (dsRNases) such as those in the RNase III and ribonuclease L family of enzymes also play a role in RNA target degradation. Double-stranded ribonucleases and oligomeric compounds that trigger them are further described in U.S. Pat. Nos. 5,898,031 and 6,107,094.

In order to obtain long-term gene silencing, expression vectors that continually express siRNAs or shRNAs in stably transfected mammalian cells can be used (Brummelkamp et al., Science 296: 550-553, 2002; Lee et al., Nature Biotechnol. 20:500-505, 2002; Miyagishi, M, and Taira, K. Nature Biotechnol. 20:497-500, 2002; Paddison, et al., Genes & Dev. 16:948-958, 2002; Paul et al., Nature Biotechnol. 20:505-508, 2002; Sui, Proc. Natl. Acad. Sci. USA 99(6):5515-5520, et al., 2002; Yu et al., Proc. Natl. Acad. Sci. USA 99(9):6047-6052, 2002). Many of these plasmids have been engineered to express shRNAs lacking poly (A) tails. Transcription of shRNAs can be initiated at a polymerase III (pol III) promoter and is believed to be terminated at position 2 of a 4-5-thymine transcription termination site. Upon expression, shRNAs are thought to fold into a stem-loop structure with 3' UU-overhangs. Subsequently, the ends of these shRNAs are processed, converting the shRNAs into ~21 nt siRNA-like molecules. The siRNA-like molecules can, in turn, bring about gene-specific silencing in the transfected mammalian cells.

Interfering RNAs are therefore double stranded oligonucleotide agents that have complementarity to (i.e., are able to hybridize with) a portion of the target RNA (generally messenger RNA (mRNA)). Generally, such complementarity is 100%, but can be less if desired, such as about 20%, about 25%, about 30%, about 35%, about 40%, about 45%, about 50%, about 55%, about 60%, about 70%, about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% as long as conditions permit hybridization of the siRNA to the desired target. By way of sample and without limitation, 19 bases out of 21 bases may be base-paired. Thus, it will be understood that an oligonucleotide used in the methods need not be 100% complementary to a desired target nucleic acid in order for the siRNA to hybridize to the target. Moreover, oligonucleotides may hybridize to each other over one or more segments such that intervening or adjacent segments are not involved in the hybridization event (e.g., a loop structure or hairpin structure). Percent complementarity between any given oligonucleotide can be determined routinely using BLAST programs (Basic Local Alignment Search Tools) and PowerBLAST programs known in the art (Altschul et al., 1990, J. Mol. Biol., 215: 403-410; Zhang and Madden, 1997, Genome Res., 7: 649-656).

In some aspects, where selection of a target which differs from other non-target sequence variants by a small number of nucleotides is desired, 100% complementarity to the target sequence is required in order to effectively discern the target sequence from the other non-target sequences. When selecting between targets with little sequence difference, choice of length is also an important factor because it is the other factor involved in the percent complementary and the ability to differentiate between target and n on-target sequences.

"Hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

The term "RNA" includes duplexes of two separate strands, as well as single, triple, or quadruple stranded structures. An example of a single strand RNA is an RNA with a hairpin loop. An inhibitory RNA sequence needs to be of sufficient length to bring the small interfering RNA and target RNA together through complementary base-pairing interactions. The RNA useful in the methods disclosed herein may be of varying lengths. The RNA, as disclosed herein, comprises a domain in a single strand of the duplex sufficiently complementary to a sequence in a target polynucleotide to permit hybridization of the single strand to the target polynucleotide under appropriate conditions, and hybridization of the single stranded domain of the duplex to the sequence in the target polynucleotide creates a substrate site recognized by a polypeptide. The length of this single stranded domain is in some aspects greater than or equal to ten nucleotides and of sufficient length to hybridize with the target RNA; specifically 10-100 nucleotides; more specifically any integer between 10 and 80 nucleotides, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100. By "sufficient length" is meant an oligonucleotide of greater than or equal to 10 nucleotides that is of a length great enough to provide the intended function under the expected condition.

As used herein, the term "target" or "target polynucleotide" refers to a polynucleotide against which a given RNA can be directed.

As used herein, "duplex" refers to a region in two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotide units can base pair with another polynucleotide of 21 nucleotide units, yet only 19 bases on each strand are complementary or substantially complementary, such that the "duplex" has 19 base pairs. The remaining bases may, for example, exist as 5' and 3' overhangs. Further, within the duplex, 100% complementarity is not required; substantial complementarity is allowable within a duplex. Substantial complementarity refers to 75% or greater complementarity. For example, a mismatch in a duplex consisting of 19 base pairs results in 94.7% complementarity, rendering the duplex substantially complementary.

RNA may be polymerized in vitro, recombinant RNA, contain chimeric sequences, or derivatives of these groups.

The RNA contains, in various embodiments, ribonucleotides, deoxyribonucleotides, synthetic nucleotides, or any suitable combination such that expression of the target gene is inhibited.

A delivered RNA can stay within the cytoplasm or nucleus. The RNA can be delivered to a cell to inhibit expression of an endogenous or exogenous nucleotide sequence or protein or to affect a specific physiological characteristic not naturally associated with the cell.

A RNA can be delivered to a cell in order to produce a cellular change that is therapeutic. The delivery of RNA or other genetic material for therapeutic purposes (the art of improving health in an animal including treatment or prevention of disease) is called gene therapy. The RNA can be delivered either directly to the organism in situ or indirectly by transfer to a cell ex vivo that is then transplanted into the organism. Entry into the cell is required for the RNA to block the production of a protein or to decrease the amount of a RNA. Polynucleotide sequences contemplated by the present disclosure are further described below.

RNA Features and Modifications

The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Polynucleotides may also include modified nucleobases. A "modified base" is understood in the art to be one that can pair with a natural base (e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Modified polynucleotides are contemplated for functionalizing nanoparticles wherein both one or more sugar and/or one or more internucleotide linkage of the nucleotide units in the polynucleotide is replaced with "non-naturally occurring" groups. In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotide."

Modified polynucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be a basic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including —$CH_2$—NH—O—$CH_2$—, —$CH_2$—N($CH_3$)—O—$CH_2$, $CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the oligo consists of 2 to 4, desirably 3, groups/atoms selected from —$CH_2$, O, S, NRH—, >C=O, >C=NRH, >C=S, —Si(R")$_2$—, —S(O)$_2$—, —P(O)$_2$—, —PO(BH$_3$)—P(O,S)—P(S)$_2$—, —PO(R")—, —PO(OCH$_3$)—, and —PO(NHRH)—, where RH is selected from hydrogen and C1-4-alkyl, and R" is selected from C1-6-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—CH2-O—, —O—CH2-CH2-, —O—CH2-CH= (including R5 when used as a linkage to a succeeding monomer), —$CH_2$—$CH_2$—O—, —NRH—$CH_2$—$CH_2$—, —$CH_2$—$CH_2$—NRH—, —$CH_2$—NRH—$CH_2$—O—$CH_2$—$CH_2$—NRH—, —NRH—CO—O—, —NRH—CO—NRH—, —NRH—CS—NRH—, —NRH—C(=NRH)—NRH—, —NRH—CO—$CH_2$—NRH—O—CO—O—, —O—CO—$CH_2$—O—, —O—$CH_2$—CO—O—, —$CH_2$—CO—NRH—, —O—CO—NRH—, —O—$CH_2$—CO—NRH—, —O—$CH_2$—$CH_2$—NRH—, —CH=N—O—, —$CH_2$—NRH—O—, —$CH_2$—O—N= (including R5 when used as a linkage to a succeeding monomer), —$CH_2$—O—NRH—, —CO—NRH—$CH_2$—, —$CH_2$—NRH—O—, —$CH_2$—NRH—CO—, —O—NRH—$CH_2$—, —O—NRH, —O—$CH_2$—S—, —S—$CH_2$—O—, —$CH_2$—$CH_2$—S—, —O—$CH_2$—$CH_2$—S—, —S—$CH_2$—CH= (including R5 when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—SO$_2$—$CH_2$—, —O—SO—O—, —O—S(O)$_2$—O—, —O—S(O)$_2$—$CH_2$—, —O—S(O)$_2$—NRH—, —NRH—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHRN)—O—, —O—P(O)$_2$—NRHH—, —NRH—P(O)$_2$—O—, —O—P(O,NRH)—O—, —$CH_2$—P(O)$_2$—O—, —O—P(O)$_2$—$CH_2$—, and —O—Si(R")$_2$—O—; among which —$CH_2$—CO—NRH—, —$CH_2$—NRH—O—, —S—$CH_2$—O—, —O—P(O)$_2$—O—O—P(—O,S)—O—, —O—P(S)$_2$—O—, —NRHP(O)$_2$—O—, —O—P(O, NRH)—O—, —O—PO(R")—O—, —O—PO(CH$_3$)—O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$]$_2$, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH$_2$—)n group bridging the 2' oxygen atom and the 4' carbon atom wherein n is 1 or 2. LNAs and preparation thereof are described in WO 98/39352 and WO 99/14226, the disclosures of which are incorporated herein by reference.

Chimerics

It is not necessary for all positions in a given compound to be uniformly modified, and in fact more than one of the aforementioned modifications may be incorporated in a single compound or even at a single nucleoside within an oligonucleotide. These "chimeric" antisense compounds typically contain at least one region including a modification as described herein, while the remainder of the oligonucleotide remains "unmodified."

In certain aspects, the modification confers increased resistance to nuclease degradation, increased cellular uptake, increased stability and/or increased binding affinity for the target nucleic acid. In other aspects the modification serves as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric compounds may be formed as composite structures of two or more oligonucleotides, modified oligonucleotides, oligonucleosides and/or oligonucleotide mimetics as described above. Such compounds have also been referred to in the art as hybrids or gapmers. See, for example, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, the disclosures of which are incorporated herein by reference in their entireties.

RNA Sequences and Hybridization

In some aspects, the disclosure provides methods of targeting specific nucleic acids, e.g., specific RNAs coded by sirtuin genes as disclosed in Table 5. The target nucleic acid may be in cells, tissue samples, or biological fluids, as also known in the art. See, e.g., Sambrook et al., Molecular Cloning: A Laboratory Manual (2nd ed. 1989) and B. D. Hames and S. J. Higgins, Eds., Gene Probes 1 (IRL Press, New York, 1995).

The terms "start codon region" and "translation initiation codon region" refer to a portion of a mRNA or gene that encompasses contiguous nucleotides in either direction (i.e., 5' or 3') from a translation initiation codon. Similarly, the terms "stop codon region" and "translation termination codon region" refer to a portion of such a mRNA or gene that encompasses contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the oligonucleotides on the functionalized nanoparticles.

Other target regions include the 5' untranslated region (5'UTR), the portion of an mRNA in the 5' direction from the translation initiation codon, including nucleotides between the 5' cap site and the translation initiation codon of a mRNA (or corresponding nucleotides on the gene), and the 3' untranslated region (3'UTR), the portion of a mRNA in the 3' direction from the translation termination codon, including nucleotides between the translation termination codon and 3' end of a mRNA (or corresponding nucleotides on the gene). The 5' cap site of a mRNA comprises an N7-methylated guanosine residue joined to the 5'-most residue of the mRNA via a 5'-5' triphosphate linkage. The 5' cap region of a mRNA is considered to include the 5' cap structure itself as well as the first 50 nucleotides adjacent to the cap site. Other Methods of Blocking or Reducing Sirtuin Activity Also disclosed herein are methods of increasing virus yield by inhibiting sirtuin activity by additional methods. For example, dominant negative proteins can be used to inhibit sirtuin activity. Dominant negative proteins are proteins that interfere with the activity of their normal counterparts. Dominant negative proteins no longer mediate all aspects of a protein's normal function, and also inhibit the normal functioning of the corresponding wild-type protein or the function of other proteins with which they interact. Dominant negative proteins can be introduced into cells by a variety of methods well known in the art.

Also disclosed herein are methods of increasing virus yield by using cells or tissues (or in the case of chickens, eggs) isolated from transgenic animals in which one or more sirtuin genes have been deleted or otherwise partially or completely inactivated. Transgenic animals can be produced by methods well known in the art.

Also disclosed herein are methods of increasing virus yield by introducing mutations into cells that partially or completely inactivate the expression one or more sirtuins. Various methods for directing mutations to specific targets within cells are well known in the art, e.g., by using engineered zinc-finger endonucleases (Sander et al., Nat Methods 8, 67-9, 2011) or by using TALENS (Cermak et al., Nucl Acids Res 39, e82).

The references cited throughout this application, are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

Any single embodiment herein may be supplemented with one or more element from any one or more other embodiment herein.

It is understood, therefore, that this invention is not limited to the particular embodiments disclosed, but is intended to cover all modifications which are within the spirit and scope of the invention as defined by the appended claims; the above description; and/or shown in the attached drawings.

EXAMPLES OF THE EMBODIMENTS

Paragraph 1. A composition comprising a one or more sirtuin agonist.

Paragraph 2. The composition of paragraph 1, wherein the one or more sirtuin agonist increases the activity of any, a subset of, or all of SIRT1, SIRT2, SIRT3, SIRT4, SIRT5, SIRT6 or SIRT7.

Paragraph 3. The composition of paragraph 1 or 2, wherein the one or more sirtuin agonist is selected from the group consisting of small molecules, nucleic acids, proteins, peptide based activators, CAY10602, Resveratrol, Quercetin, Butein, Piceatannol, Isoiquiritigenin, Fisetin, Pyrroloquinoxaline, Oxazolopyridine, SRT1720, SRT1460, SRT2379 and SRT2104.

Paragraph 4. The composition of any of the preceding paragraphs, including any one or more of CAY10602, Resveratrol, Quercetin, Butein, Piceatannol, Isoiquiritigenin, Fisetin, Pyrroloquinoxaline, Oxazolopyridine, SRT1720, SRT1460, SRT2379 or SRT2104.

Paragraph 5. A composition comprising a sirtuin gene expression activator.

Paragraph 6. A composition comprising a sirtuin allosteric activator.

Paragraph 7. The composition of any of the preceding paragraphs, wherein the agonist includes at least one of a small molecule, a nucleic acid, a protein, or a peptide; the expression activator includes at least one of a small molecule, a nucleic acid, a protein, or a peptide; and the allosteric activator includes at least one of a small molecule, a nucleic acid, a protein, or a peptide.

Paragraph 8. A composition comprising at least one of a sirtuin agonist, a sirtuin gene expression activator, or a sirtuin activator of any of the preceding paragraphs.

Paragraph 9. A composition comprising one or more sirtuin antagonist.

Paragraph 10. The composition of paragraph 9 wherein the one or more sirtuin antagonists decreases the activity of both of SIRT1 and SIRT2.

Paragraph 11. The composition of paragraph 9 or 10 wherein the sirtuin antagonist is selected from the group consisting of small molecules, nucleic acids, proteins, peptide based activators alone or in combination with at least one of Cambinol, Tenovin 1, Tenovin 6, Salermide and Sirtinol.

Paragraph 12. A composition comprising one or more sirtuin gene expression inhibitors.

Paragraph 13. A composition comprising one or more sirtuin competitive inhibitors.

Paragraph 14. The composition of any of paragraphs 9-13, wherein the antagonist includes at least one of a small molecule, a nucleic acid, a protein, or a peptide; the expression inhibitor includes at least one of a small molecule, a nucleic acid, a protein, or a peptide; and the competitive inhibitor includes at least one of a small molecule, a nucleic acid, a protein, or a peptide.

Paragraph 15. A composition comprising at least one of a sirtuin antagonist, a sirtuin gene expression inhibitor, or a sirtuin competitive inhibitor of any of the preceding paragraphs.

Paragraph 16. A pharmaceutical composition comprising the composition of any of paragraphs 1-15 and a pharmaceutically acceptable carrier.

Paragraph 17. The pharmaceutical composition of paragraph 16, wherein the pharmaceutically acceptable carrier includes at least one substance selected from the group consisting of ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts, electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, waxes, polyethylene glycol, starch, lactose, dicalcium phosphate, microcrystalline cellulose, sucrose, talc, magnesium carbonate, kaolin, non-ionic surfactants, edible oils, physiological saline, bacteriostatic water, Cremophor EL™ (BASF, Parsippany, N.J.) and phosphate buffered saline (PBS).

Paragraph 18. A method of treating disease comprising administering the composition of any of paragraphs 1-15 or the pharmaceutical composition of any of paragraphs 16-17 to a patient.

Paragraph 19. A method of treating disease comprising administering the composition of any of paragraphs 1-15 or the pharmaceutical composition of any of paragraphs 16-17 to a patient, wherein the disease is caused by any one or more virus.

Paragraph 20. A method of treating disease comprising administering the composition of any of paragraphs 1-15 or the pharmaceutical composition of any of paragraphs 16-17 to a patient, wherein the disease is caused by a single virus.

Paragraph 21. A method of treating disease comprising providing the composition of any of paragraphs 1-15 or the pharmaceutical composition of any of paragraphs 16-17 to a patient, wherein the disease is caused by HCMV.

Paragraph 22. A method of treating disease comprising induction of sirtuin gene expression in a patient.

Paragraph 23. A method of treating disease comprising inhibition of sirtuin gene expression in a patient.

Paragraph 24. The method of paragraph 22 or 23, wherein the expression of any one or more of SIRT1, SIRT2, SIRT3, SIRT4, SIRT5, SIRT6 or SIRT7 is induced or inhibited, respectively.

Paragraph 25. A method of inhibiting virus production comprising contacting the virus with a sirtuin agonist.

Paragraph 26. The method of paragraph 25, wherein the sirtuin agonist is a polyhydroxy chalcone, polyhydroxy flavonoid, polyhydroxy stilbene, or a combination thereof.

Paragraph 27. The method of paragraph 25, wherein the agonist has a structure

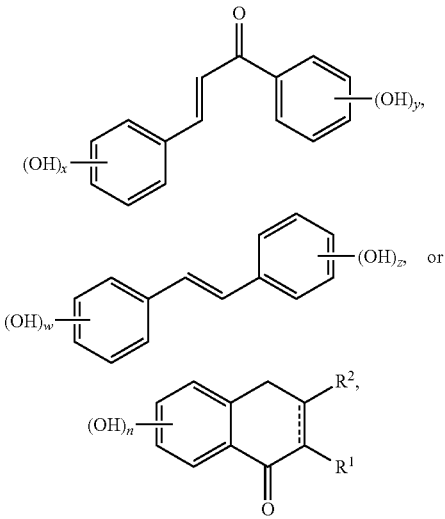

wherein
$R^1$ is H or OH and $R^2$ is

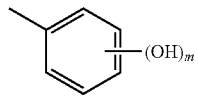

or $R^1$ is

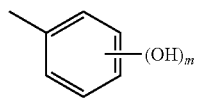

and $R^2$ is H or OH;

the dashed line indicates an optional double bond;
x and y are each 0, 1, 2, 3, 4, or 5, and x+y≥1;
w and z are each 0, 1, 2, 3, 4, or 5, and w+z≥1; and
n and m are each 0, 1, 2, 3, 4, or 5, n+m≥1,
or a salt or ester thereof.

Paragraph 28. The method of paragraph 27, wherein the dashed line is a double bond.

Paragraph 29. The method of paragraph 27 or 28, wherein $R^1$ is H or OH and $R^2$ is

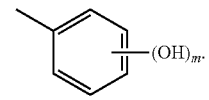

Paragraph 30. The method of paragraph 27 or 28, wherein $R^2$ is H or OH and $R^1$ is

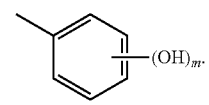

Paragraph 31. The method of paragraph 25, wherein the sirtuin agonist is resveratrol, quercetin, rutin, butein, piceatannol, isoliquiritigenin, fisetin, fustin, sulfuretin, genistein, daidzein, taxifolin, aromadedrin, a combination thereof, or a salt or ester thereof.

Paragraph 32. The method of paragraph 25, wherein the sirtuin agonist is CAY10602, pyrroloquinoxaline, oxazolopyridine, SRT1720, SRT1460, SRT2379, SRT2104, or GSK 184072.

Paragraph 33. The method of paragraph 25, wherein the sirtuin agonist is 3,5-dihydroxy-4'-chloro-trans-stilbene, dipyridamole, 3,5-dihydroxy-4'ethyl-trans-stilbene, 3,5-dihydroxy-4'-isopropyl-trans-stilbene, 3,5-dihydroxy-4'-methyl-trans-stilbene, resveratrol, 3,5-dihydroxy-4'thiomethyl-trans-stilbene, 3,5-dihydroxy-4'-carbomethoxy-trans-stilbene, isoliquiritgenin, 3,5-dihydro-4'nitro-trans-stilbene, 3,5-dihydroxy-4'azido-trans-stilbene, piceatannol, 3-methoxy-5-hydroxy-4'acetamido-trans-stilbene, 3,5-dihydroxy-4'acetoxy-trans-stilbene, pinosylvin, fisetin, (E)-1-(3, 5-dihydrophenyl)-2-(4-pyridyl)ethene, (E)-1-(3,5-dihydrophenyl)-2-(2-napthyl)ethene, 3,5-dihydroxy-4'-acetamide-trans-stilbene, butein, quercetin, 3,5-dihydroxy-4'-thioethyl-trans-stilbene), 3,5-dihydroxy-4'carboxy-trans-stilbene, 3,4'-dihydroxy-5-acetoxy-trans-stilbene, or a combination thereof.

Paragraph 34. The method of paragraph 25, wherein the sirtuin agonist is trans-stilbene, cis-stilbene, resveratrol, piceatannol, rhapontin, deoxyrhapontin, butein, chalcon; isoliquirtigen; butein; 4,2',4'-trihydroxychalcone; 3,4,2',4', 6'-pentahydroxychalcone; flavone, morin, fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein, genistein, naringenin; flavanone; 3,5,7,3',4'-pentahydroxyflavanone; pelargonidin chloride, cyanidin chloride, delphinidin chloride, (−)-epicatechin (Hydroxy Sites: 3,5,7,3',4'); (−)-catechin (Hydroxy Sites: 3,5,7,3',4'); (−)-gallocatechin (Hydroxy Sites: 3,5,7, 3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanam-inium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid.H2O); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperzainyl)m-ethyl)-3,4-dihydro-2,5,7,8-tetramethyl-2H-1-benzopyran-6-ol.2HCl); .beta.-1'-5-methyl-nicotinamide-2'-deoxyribose; .beta.-D-1'-5-methyl-nico-tinamide-2'-deoxyribofuranoside; .beta.-1'-4,5-dimethyl-nicotinamide-2'-de-oxyribose; or .beta.-D-1'-4,5-dimethyl-nicotinamide-2'-deoxyribofuranoside; dipyridamole, ZM 336372 (3-(dimethylamino)-N-[3-[(4-hydroxybenzoyl)-amino]-4-methylphenyl]benzamide), camptothecin, coumestrol, nordihydroguaiaretic acid, esculetin, SRT-1720 (Sirtris), SRT-1460 (Sirtris), SRT-2183 (Sirtris), analogs thereof, or combinations thereof.

Paragraph 35. The method of any one of paragraphs 25-34, wherein the sirtuin is SIRT1, SIRT2, SIRT3, SIRT4, SIRT5, SIRT6, SIRT7, or a combination thereof.

Paragraph 36. The method of any one of paragraphs 25-35, wherein the agonist activates only one sirtuin.

Paragraph 37. The method of any one of paragraphs 25-36, wherein the contacting comprising administering the agonist to a subject suffering from a viral infection.

Paragraph 38. The method of paragraph 37, wherein the subject is human.

Paragraph 39. The method of any one of paragraphs 25-38, wherein the virus is HCMV.

Paragraph 40. A method of inhibiting virus production comprising contacting the virus with a SIRT1/SIRT2 dual inhibitor.

Paragraph 41. The method of paragraph 40, wherein the SIRT1/SIRT2 dual inhibitor is cambinol, salermide, tenovin-6, tenovin-1, or a combination thereof.

Paragraph 42. The method of paragraph 40 or 41, wherein the virus inactivates p53 during viral replication.

Paragraph 43. The method of any one of paragraphs 40-42, wherein the virus is HCMV.

Paragraph 44. The method of any one of paragraphs 40-42, wherein the virus is human papilloma virus, HSV1, Ad5, FluA, human adenovirus, hepatitis B virus, hepatitis C virus, or HIV.

Paragraph 45. The method of any one of paragraphs 40-42, wherein the virus is Adenoviridae (Adenovirus, with E1B-55K as a p53 inactivating protein); Hepadnaviridae (HBV, with X protein as a p53 inactivating protein); Herpesviridae (EBV, with LMP1 as a p53 inactivating protein; HSV-1 with ICP0 as a p53 inactivating protein; HCMV, with 1E1 as a p53 inactivating protein; KSHV with LANA as a p53 inactivating protein); Flaviviridae (HCV with NS5A as a p53 inactivating protein); Orthomixoviridae (Influenza A with NS1 as a p53 inactivating protein); Papillomaviridae (HPV with E6 as a p53 inactivating protein); Polyomaviridae (SV40 with Large T-antigen as a p53 inactivating protein; JC virus with Large T-antigen as a p53 inactivating protein; BK virus with Large T antigen as a p53 inactivating protein); or Retroviridae (HIV with Tat as a p53 inactivating protein).

Paragraph 46. The method of any one of paragraphs 25-45, further comprising contacting the virus with a second agent.

Paragraph 47. The method of paragraph 46, wherein the second agent is a second SIRT1/SIRT2 dual inhibitor or a second sirtuin agonist.

Paragraph 48. The method of paragraph 46, wherein the second agent is an antiviral agent.

Paragraph 49. The method of paragraph 48, wherein the antiviral agent is acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, an assembly inhibitor (e.g., rifampicin), zidovudine, or a combination thereof.

What is claimed:

1. A method of inhibiting virus production comprising contacting a virus-infected cell with a SIRT1 inhibitor and a SIRT2 inhibitor, wherein the SIRT1 inhibitor and SIRT2 inhibitor are different inhibitors, and wherein the virus is an adenovirus, a herpes virus, or an influenza virus, wherein the contacting is in vivo.

2. The method of claim 1, wherein the virus is HCMV, HSV1, FluA, or adenovirus 5.

3. The method of claim 1, further comprising contacting the virus with another agent.

4. The method of claim 3, wherein the other agent is an antiviral agent.

5. The method of claim 1, wherein the cell is a tumor cell.

6. The method of claim 5, wherein the tumor cell is infected with HCMV.

7. The method of claim 1, wherein the SIRT1 and SIRT2 are inhibited by inhibiting gene expression of at least one of the SIRT1 and SIRT2.

8. A method of inhibiting virus production comprising contacting a virus-infected cell with a SIRT1 inhibitor and a SIRT2 inhibitor, wherein the SIRT1 inhibitor and SIRT2 inhibitor are different inhibitors, and wherein the virus is a herpes virus.

* * * * *